(12) United States Patent
Williams

(10) Patent No.: US 11,000,286 B2
(45) Date of Patent: May 11, 2021

(54) SURGICAL ANVIL ASSEMBLIES FOR SURGICAL STAPLING INSTRUMENTS

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 147 days.

(21) Appl. No.: 16/275,656

(22) Filed: Feb. 14, 2019

(65) Prior Publication Data

US 2019/0298370 A1  Oct. 3, 2019

Related U.S. Application Data

(60) Provisional application No. 62/649,176, filed on Mar. 28, 2018, provisional application No. 62/649,341, filed on Mar. 28, 2018, provisional application No. 62/649,325, filed on Mar. 28, 2018, provisional application No. 62/649,304, filed on Mar. 28, 2018, provisional application No. 62/649,278, filed on Mar. 28, 2018, provisional application No. 62/649,267, filed on Mar. 28, 2018, provisional application No. 62/649,241, filed on Mar. 28, 2018, provisional application No. 62/649,227, filed on Mar. 28, 2018, provisional application No. 62/649,217, filed on Mar. 28, 2018, provisional application No. 62/649,200, filed on Mar. 28, 2018.

(51) Int. Cl.
*A61B 17/115* (2006.01)
*A61B 17/00* (2006.01)
*A61B 17/072* (2006.01)

(52) U.S. Cl.
CPC .... *A61B 17/1155* (2013.01); *A61B 2017/0046* (2013.01); *A61B 2017/00314* (2013.01); *A61B 2017/00473* (2013.01); *A61B 2017/07257* (2013.01); *A61B 2017/07271* (2013.01); *A61B 2017/07285* (2013.01)

(58) Field of Classification Search
CPC .. A61B 17/1155; A61B 17/068; A61B 17/072
USPC ... 227/180.1, 177.1, 178.1, 176.1, 175.1, 19
See application file for complete search history.

(56) References Cited

U.S. PATENT DOCUMENTS

| 3,388,847 A | 6/1968 | Kasulin et al. |
| 3,552,626 A | 1/1971 | Astafiev et al. |
| 3,638,652 A | 2/1972 | Kelley |

(Continued)

FOREIGN PATENT DOCUMENTS

| AU | 708637 B2 | 8/1999 |
| CA | 908529 A | 8/1982 |

(Continued)

OTHER PUBLICATIONS

European Search Report dated Jul. 26, 2019, corresponding to counterpart European Application No. 19165495.3; 8 pages.

(Continued)

*Primary Examiner* — Nathaniel C Chukwurah

(57) ABSTRACT

A surgical anvil assembly for use with a circular stapling instrument includes an anvil center rod defining a longitudinal axis and an anvil head pivotally coupled to the anvil center rod and movable between a first operative condition and a second tilted condition. The anvil assembly further includes a locking assembly configured to selectively lock the anvil head in each of the first and second conditions.

7 Claims, 39 Drawing Sheets

(56) References Cited

U.S. PATENT DOCUMENTS

| | | | |
|---|---|---|---|
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,754,909 A | 7/1988 | Barker et al. |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,470,006 A | 11/1995 | Rodak |
| 5,474,223 A | 12/1995 | Viola et al. |
| 5,497,934 A | 3/1996 | Brady et al. |
| 5,522,534 A | 6/1996 | Viola et al. |
| 5,533,661 A | 7/1996 | Main et al. |
| 5,588,579 A * | 12/1996 | Schnut ............... A61B 17/115 |
| | | 227/175.1 |
| 5,609,285 A | 3/1997 | Grant et al. |
| 5,632,433 A | 5/1997 | Grant et al. |
| 5,639,008 A | 6/1997 | Gallagher et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,758,814 A | 6/1998 | Gallagher et al. |
| 5,799,857 A | 9/1998 | Robertson et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |

(56) References Cited

U.S. PATENT DOCUMENTS

| | | |
|---|---|---|
| 6,605,078 B2 | 8/2003 | Adams |
| 6,623,227 B2 | 9/2003 | Scott et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,716,222 B2 | 4/2004 | McAlister et al. |
| 6,716,233 B1 | 4/2004 | Whitman |
| 6,742,692 B2 | 6/2004 | Hartwick |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,827,246 B2 | 12/2004 | Sullivan et al. |
| 6,840,423 B2 | 1/2005 | Adams et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,981,941 B2 | 1/2006 | Whitman et al. |
| 7,032,798 B2 | 4/2006 | Whitman et al. |
| 7,059,331 B2 | 6/2006 | Adams et al. |
| 7,059,510 B2 | 6/2006 | Orban, III |
| 7,080,769 B2 | 7/2006 | Vresh et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,168,604 B2 | 1/2007 | Milliman et al. |
| 7,179,267 B2 | 2/2007 | Nolan et al. |
| 7,182,239 B1 | 2/2007 | Myers |
| 7,303,106 B2 | 12/2007 | Milliman et al. |
| 7,364,060 B2 | 4/2008 | Milliman |
| 8,360,295 B2 | 1/2013 | Milliman et al. |
| 8,424,535 B2 | 4/2013 | Hessler et al. |
| 8,540,132 B2 | 9/2013 | Marczyk et al. |
| 8,789,737 B2 | 7/2014 | Hodgkinson et al. |
| 8,806,973 B2 | 8/2014 | Ross et al. |
| 9,055,943 B2 | 6/2015 | Zemlok et al. |
| 9,247,940 B2 | 2/2016 | Whitman et al. |
| 9,532,781 B2 | 1/2017 | Milliman et al. |
| 2001/0000903 A1 | 5/2001 | Heck et al. |
| 2001/0010320 A1 | 8/2001 | Bolduc et al. |
| 2001/0054636 A1 | 12/2001 | Nicol |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0144675 A1 | 7/2003 | Nicolo |
| 2003/0178465 A1 | 9/2003 | Bilotti |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2005/0051597 A1 | 3/2005 | Toledano |
| 2005/0067454 A1 | 3/2005 | Vresh et al. |
| 2005/0087580 A1 | 4/2005 | Orban |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2005/0205639 A1 | 9/2005 | Milliman |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0047308 A1 | 3/2006 | Ortiz et al. |
| 2006/0085032 A1 | 4/2006 | Viola |
| 2006/0085033 A1 | 4/2006 | Criscuolo et al. |
| 2006/0085034 A1 | 4/2006 | Bettuchi |
| 2006/0085035 A1 | 4/2006 | Viola |
| 2006/0097025 A1 | 5/2006 | Milliman et al. |
| 2006/0108393 A1 | 5/2006 | Heinrich et al. |
| 2006/0144897 A1 | 7/2006 | Jankowski et al. |
| 2006/0151567 A1 | 7/2006 | Roy |
| 2006/0191975 A1 | 8/2006 | Adams et al. |
| 2006/0201989 A1 | 9/2006 | Ojeda |
| 2006/0201993 A1 | 9/2006 | Hur |
| 2006/0241692 A1 | 10/2006 | McGuckin et al. |
| 2006/0255090 A1 | 11/2006 | Milliman et al. |
| 2006/0289601 A1 | 12/2006 | Orban |
| 2007/0023475 A1 | 2/2007 | Csiky |
| 2007/0027473 A1 | 2/2007 | Vresh et al. |
| 2007/0029363 A1 | 2/2007 | Popov |
| 2007/0034666 A1 | 2/2007 | Holsten et al. |
| 2007/0034667 A1 | 2/2007 | Holsten et al. |
| 2007/0034668 A1 | 2/2007 | Holsten et al. |
| 2007/0038248 A1 | 2/2007 | Heinrch |
| 2007/0060952 A1 | 3/2007 | Roby et al. |
| 2008/0277448 A1 | 11/2008 | Roby et al. |
| 2010/0038401 A1* | 2/2010 | Milliman .............. A61B 17/068 227/175.1 |
| 2012/0325888 A1* | 12/2012 | Qiao ................... A61B 17/115 227/175.1 |
| 2015/0014392 A1 | 1/2015 | Williams et al. |
| 2015/0129635 A1* | 5/2015 | Williams ........... A61B 17/1155 227/177.1 |
| 2016/0007999 A1 | 1/2016 | Latimer et al. |

FOREIGN PATENT DOCUMENTS

| | | |
|---|---|---|
| EP | 012382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1949861 A2 | 7/2008 |
| EP | 2286731 A2 | 2/2011 |
| EP | 2583631 A1 | 4/2013 |
| EP | 2873378 A1 | 5/2015 |
| EP | 2959846 A1 | 12/2015 |
| EP | 3031408 A1 | 6/2016 |
| EP | 3087933 A1 | 11/2016 |
| EP | 3111857 A1 | 1/2017 |
| GB | 1185292 A | 3/1970 |
| GB | 2016991 A | 9/1979 |
| GB | 2070499 A | 9/1981 |
| WO | 8706448 A1 | 11/1987 |
| WO | 8900406 A1 | 1/1989 |
| WO | 9006085 A1 | 6/1990 |
| WO | 2004032766 A2 | 4/2004 |

(56) References Cited

FOREIGN PATENT DOCUMENTS

| | | |
|---|---|---|
| WO | 2014139442 A1 | 9/2014 |
| WO | 2015065484 A1 | 5/2015 |

OTHER PUBLICATIONS

European Search Report dated Jul. 30, 2019, corresponding to counterpart European Application No. 19165491.2; 10 pages.
European Search Report dated Jul. 30, 2019, corresponding to counterpart European Application No. 19165571.1; 8 pages.
European Search Report dated Jul. 24, 2019, corresponding to counterpart European Application No. 19165493.8; 6 pages.
European Search Report dated Jul. 31, 2019, corresponding to counterpart European Application No. 19165599.2; 7 pages.
European Search Report dated Jul. 31, 2019, corresponding to counterpart European Application No. 19165627.1; 8 pages.

\* cited by examiner

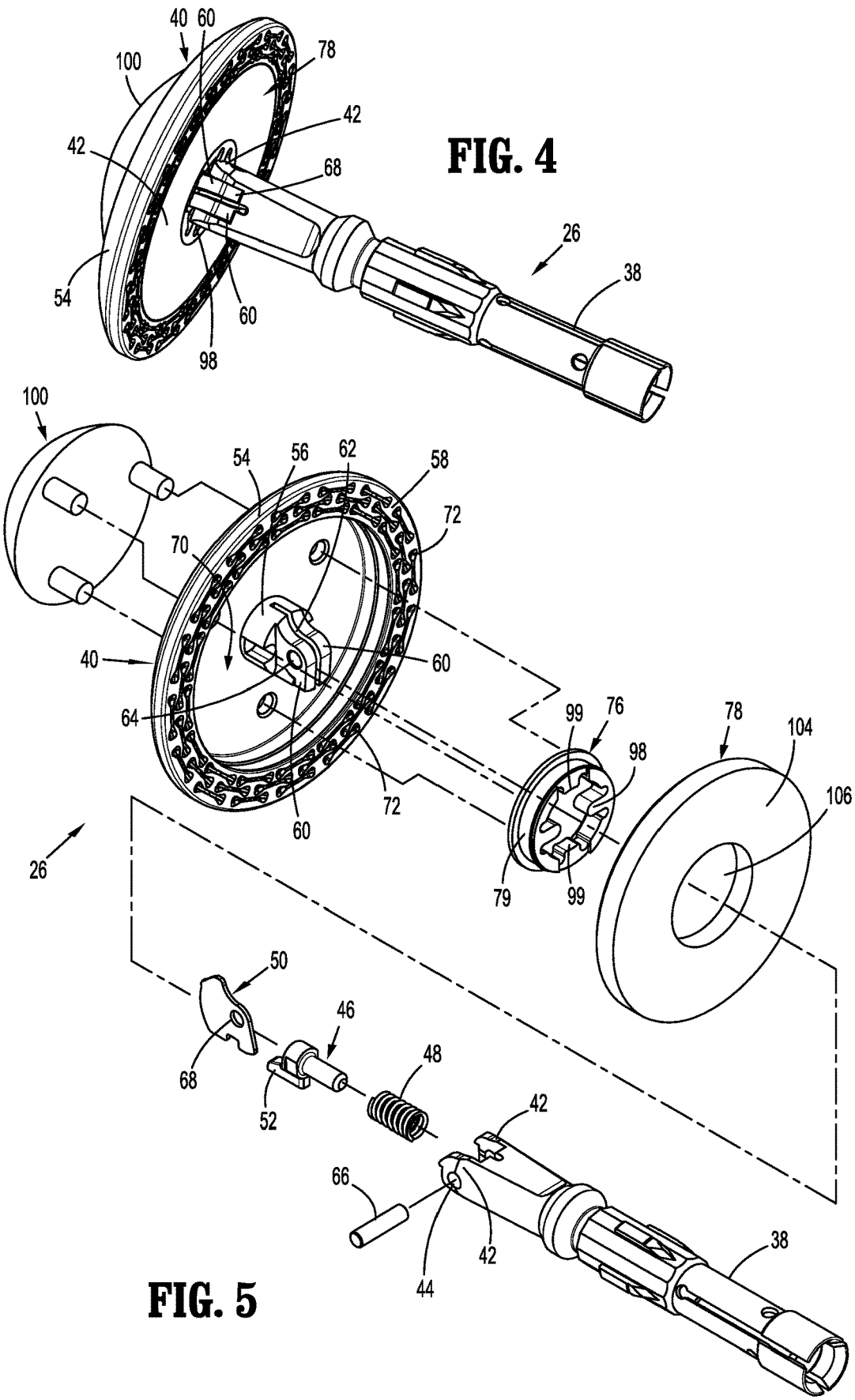

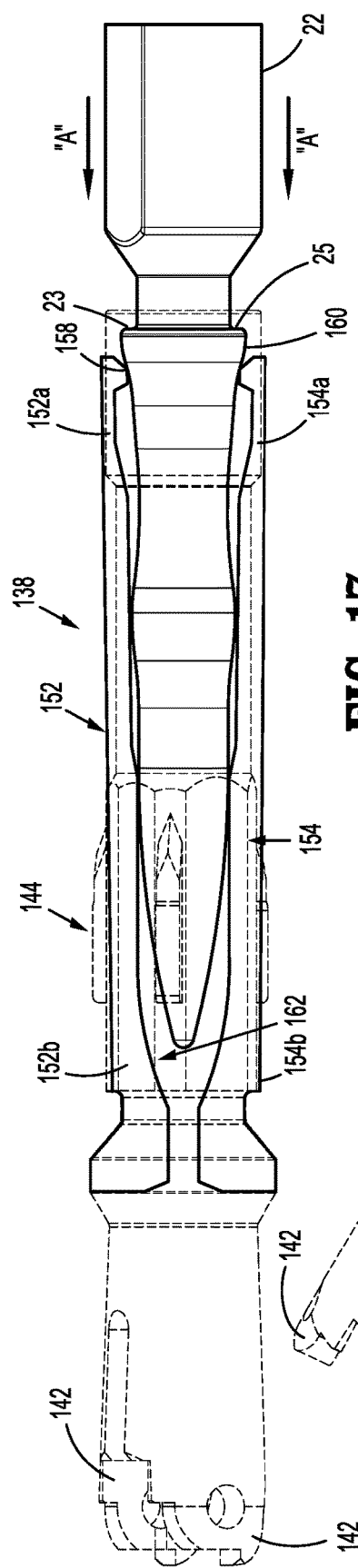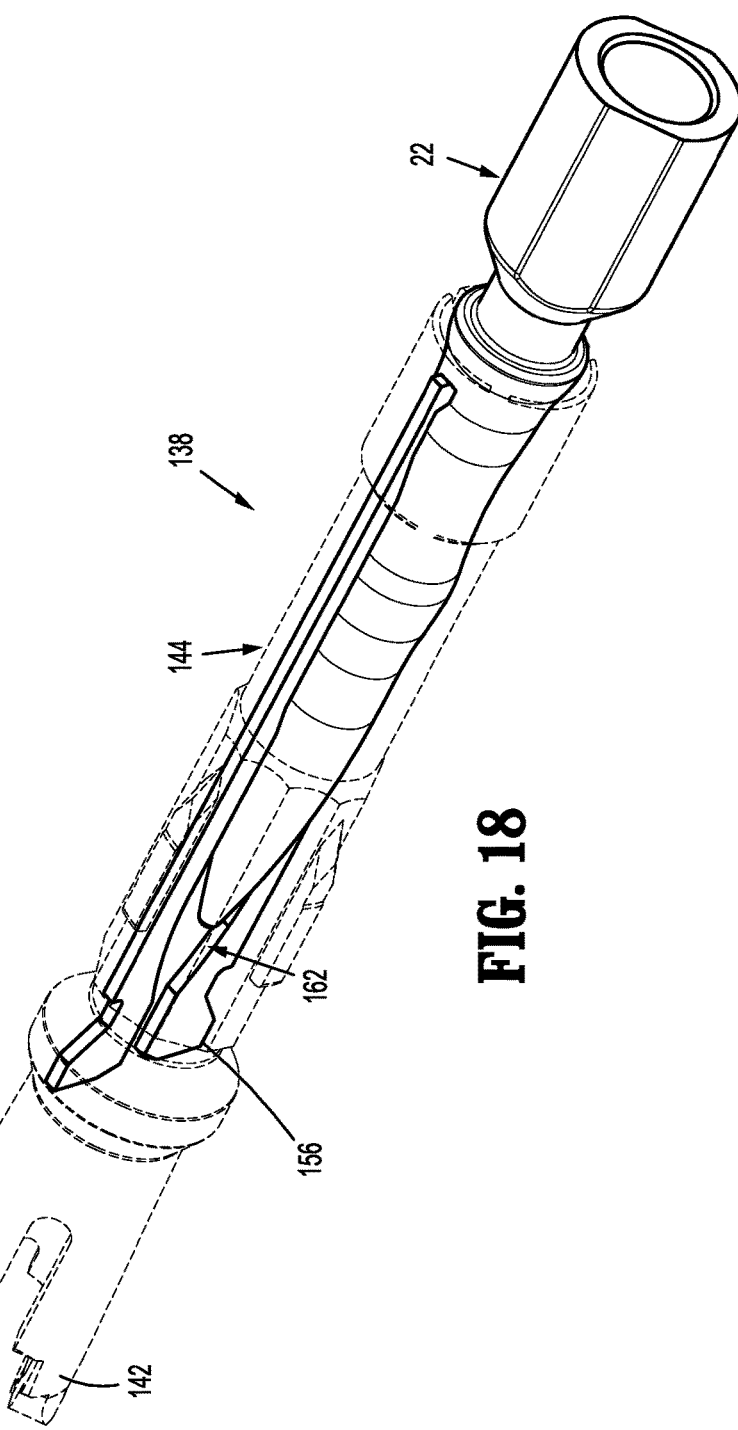

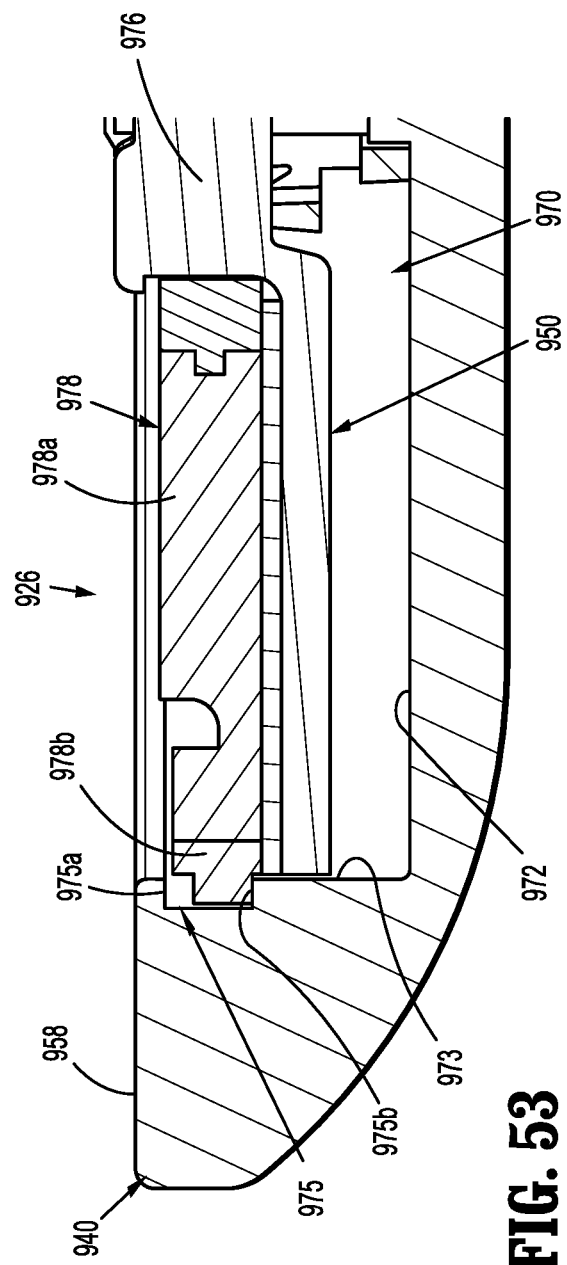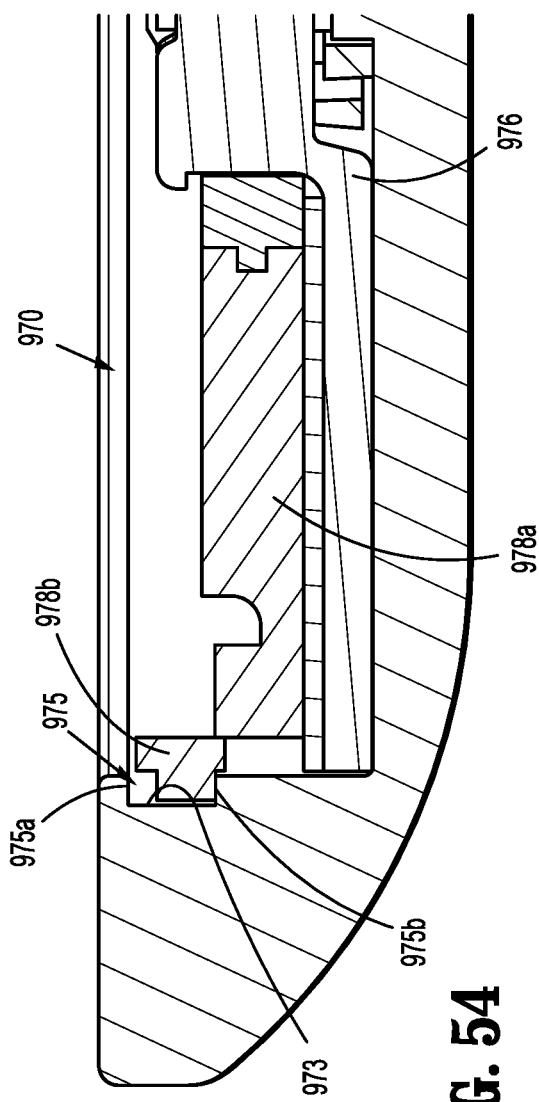
FIG. 53
FIG. 54

SURGICAL ANVIL ASSEMBLIES FOR SURGICAL STAPLING INSTRUMENTS

CROSS-REFERENCE TO RELATED APPLICATIONS

This application claims the benefit of, and priority to, U.S. Provisional Patent Application Nos. 62/649,176; 62/649,341; 62/649,325; 62/649,304; 62/649,278; 62/649,267; 62/649,241; 62/649,227; 62/649,217; and 62/649,200, each of which were filed on Mar. 28, 2018, the entire contents of each of which are incorporated herein by reference.

BACKGROUND

1. Technical Description

The present disclosure generally relates to a surgical stapling instrument and, more particularly, to a surgical anvil assembly for use with a circular stapling instrument and having an anvil head capable of pivoting or tilting to facilitate insertion and/or withdrawal of the anvil assembly relative to the operative site.

2. Background of Related Art

Circular stapling instruments for performing surgical procedures such as anastomoses, hemorrhoidectomies, and mucosectomies are well known. These devices include an anvil assembly having a center rod and an anvil head supported on the center rod. Typically, during a surgical procedure, the tool assembly of the circular stapling instrument is inserted into a tubular section or sections of tissue to join the tissue sections or remove diseased or damaged tissue from within the tissue section. In order to minimize trauma to the tissue section, the anvil head may be pivotally supported on the center rod to reduce the profile of the anvil assembly during insertion and/or removal of the tool assembly from the tissue section. In some circular stapling instruments, a component is fractured during firing to permit tilting of the anvil head relative to the center rod.

SUMMARY

In one aspect of the present disclosure, a surgical anvil assembly for use with a circular stapling instrument is provided and includes an anvil center rod, an anvil head pivotally coupled to the anvil center rod and movable between a first, operative condition and a second, tilted condition, a backup member slidably disposed within a recess of the anvil head and selectively engagable with the anvil center rod, and a locking assembly. The locking assembly includes an inner member supported on an outer surface of the anvil head, an outer member movably coupled to the inner member, and a post interconnecting the outer member and the backup member. The outer member is configured to move relative to the inner member between a first, proximal position, in which the locking assembly maintains the backup member engaged with the anvil center rod to resist movement of the anvil head relative to the anvil center rod, and a second, distal position, in which the locking assembly maintains the backup member disengaged from the anvil center rod to allow for movement of the anvil head relative to the anvil center rod.

In some aspects, the locking assembly may further include a locking member protruding outwardly from the inner member. The locking member may be configured to engage the outer member when the outer member is in the second, distal position to maintain the outer member in the second, distal position and, in turn, maintain the backup member disengaged from the anvil center rod.

The locking member may be configured to prevent movement of the backup member from the first, proximal position toward the second, distal position until a threshold, distally-oriented force has been applied to the backup member.

In some aspects, the locking member may overlap with an inner lip of the outer member to resist distal movement of the outer member relative to the inner member toward the second, distal position.

The locking member may include a first locking member extending radially outward from a first side of the inner member, and a second locking member extending radially outward from a second side of the inner member. The first and second locking members may be engagable with an inner periphery of the outer member.

In some aspects, the locking member may include a detent configured to engage an inner periphery of the outer member when the outer member is in the second, distal position.

The outer member may include a lip protruding radially inwardly from the inner periphery thereof. The lip may be disposed proximally of the detent when the outer member is in the first, proximal position, such that the detent resists movement of the outer member from the first, proximal position toward the second, distal position. The lip may be aligned with the detent when the outer member is in the second, distal position, such that the detent resists movement of the outer member from the second, distal position toward the first, proximal position.

In some aspects, the detent may be configured to move radially inward upon movement of the outer member toward the second, distal position. The detent may be configured to move radially outward upon movement of the outer member toward the first, proximal position.

The post may have a distal end disposed outside of the anvil head, an intermediary portion extending through the anvil head, and a proximal end disposed within the recess of the anvil head.

In some aspects, the anvil center rod may have a pair of arms supporting the backup member thereon when the backup member is in the first, proximal position, such that the pair of arms prevent the backup member from pivoting relative thereto.

The surgical anvil assembly may further include a cut ring positioned about the backup member and secured thereto.

In some aspects, the surgical anvil assembly may further include a cam latch mounted to a post of the anvil head. The cam latch may be configured to normally bias the anvil head to the second, tilted condition.

Other features of the present disclosure will be appreciated from the following description.

BRIEF DESCRIPTION OF THE DRAWINGS

Various embodiments of the presently disclosed surgical anvil assemblies for incorporation into surgical circular stapling instruments are described herein below with reference to the drawings, wherein:

FIG. 4 is a perspective view of the anvil assembly;

FIG. 5 is an exploded, perspective view of the anvil assembly;

FIG. 17 is a side view, with parts shown in phantom, of a trocar being inserted into the anvil center rod of FIG. 14;

FIG. 18 is a perspective view, with parts shown in phantom, of the trocar being inserted into the anvil center rod of FIG. 14;

FIG. 53 is a side cross-sectional view of another embodiment of a surgical anvil assembly for incorporation into the circular stapling instrument of FIG. 1 illustrating a ring assembly thereof in a proximal position;

FIG. 54 is a side cross-sectional view of the surgical anvil assembly of FIG. 53 illustrating the ring assembly thereof in a distal position.

DETAILED DESCRIPTION

Figure 1:
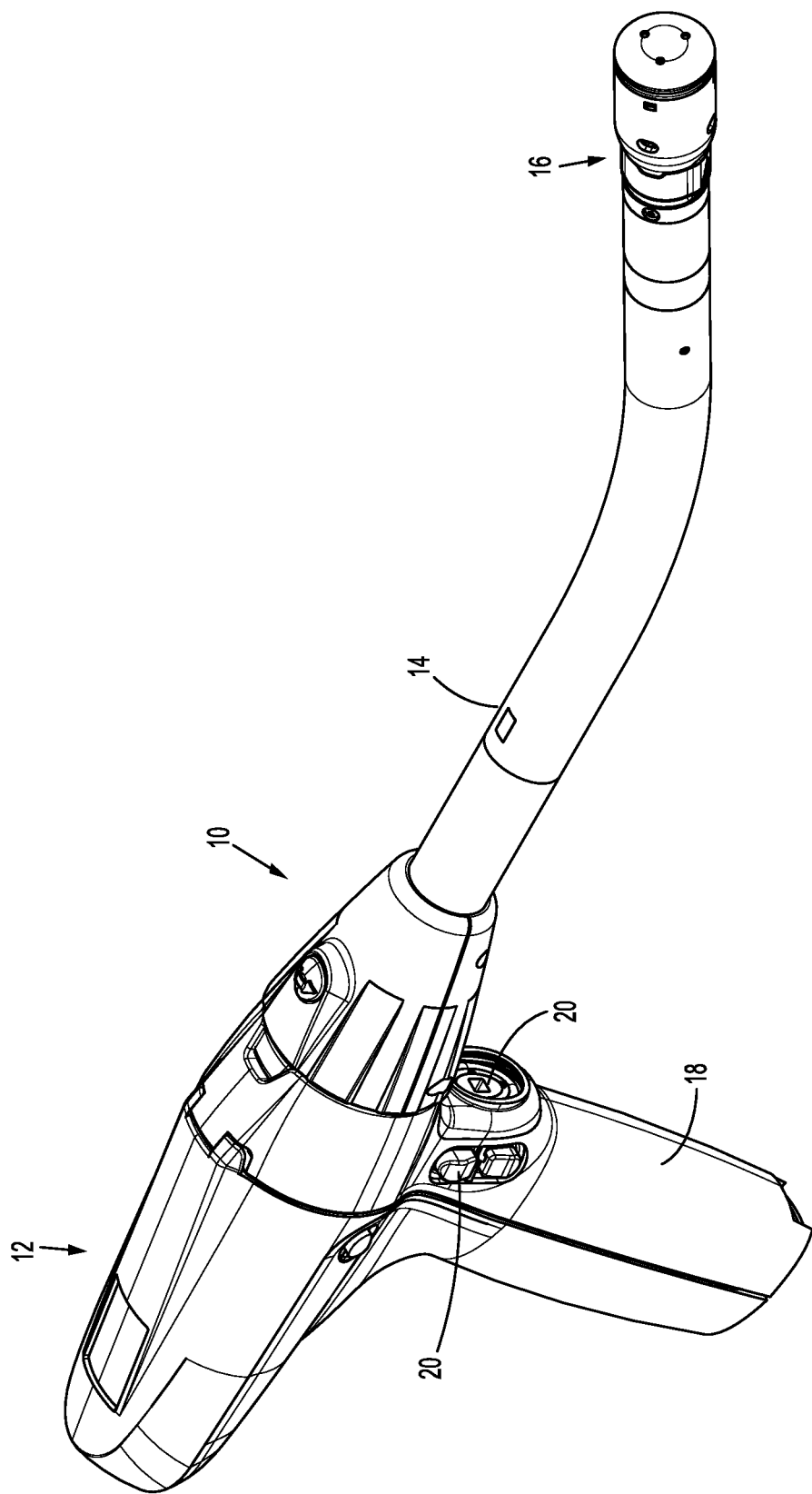
FIG. 1 is a perspective view of an exemplary embodiment of a surgical circular stapling instrument including an embodiment of a surgical anvil assembly of the present disclosure.

The presently disclosed anvil assemblies for use with various circular stapling instruments will now be described in detail with reference to the drawings in which like reference numerals designate identical or corresponding elements in each of the several views. In this description, the term "proximal" is used generally to refer to that portion of the instrument or surgical anvil assembly thereof that is closer to a clinician, while the term "distal" is used generally to refer to that portion of the instrument or surgical anvil assembly thereof that is farther from the clinician. In addition, the term clinician is used generally to refer to medical personnel including doctors, nurses, and support personnel.

The exemplary surgical stapling instrument includes a handle assembly, an elongate body or adapter, and a tool assembly coupled to the adapter. The tool assembly includes a shell assembly and an anvil assembly mounted with respect to the shell assembly. The anvil assembly includes a center rod releasably couplable to the elongate body and an anvil head which is pivotally coupled to the center rod. The anvil head is movable between a pre-fired, untilted or operative condition and a post-fired, tilted or pivoted condition. The anvil head is locked in the pre-fired position until an annular knife of the tool assembly is advanced, which frees the anvil head to pivot or rotate relative to the center rod towards the pivoted condition. The present disclosure provides, inter alia, various embodiments of mechanisms for unlocking the anvil head from the anvil center rod, and various embodiments of mechanisms that drive the rotation of the anvil head upon being unlocked from the center rod.

Figure 2:
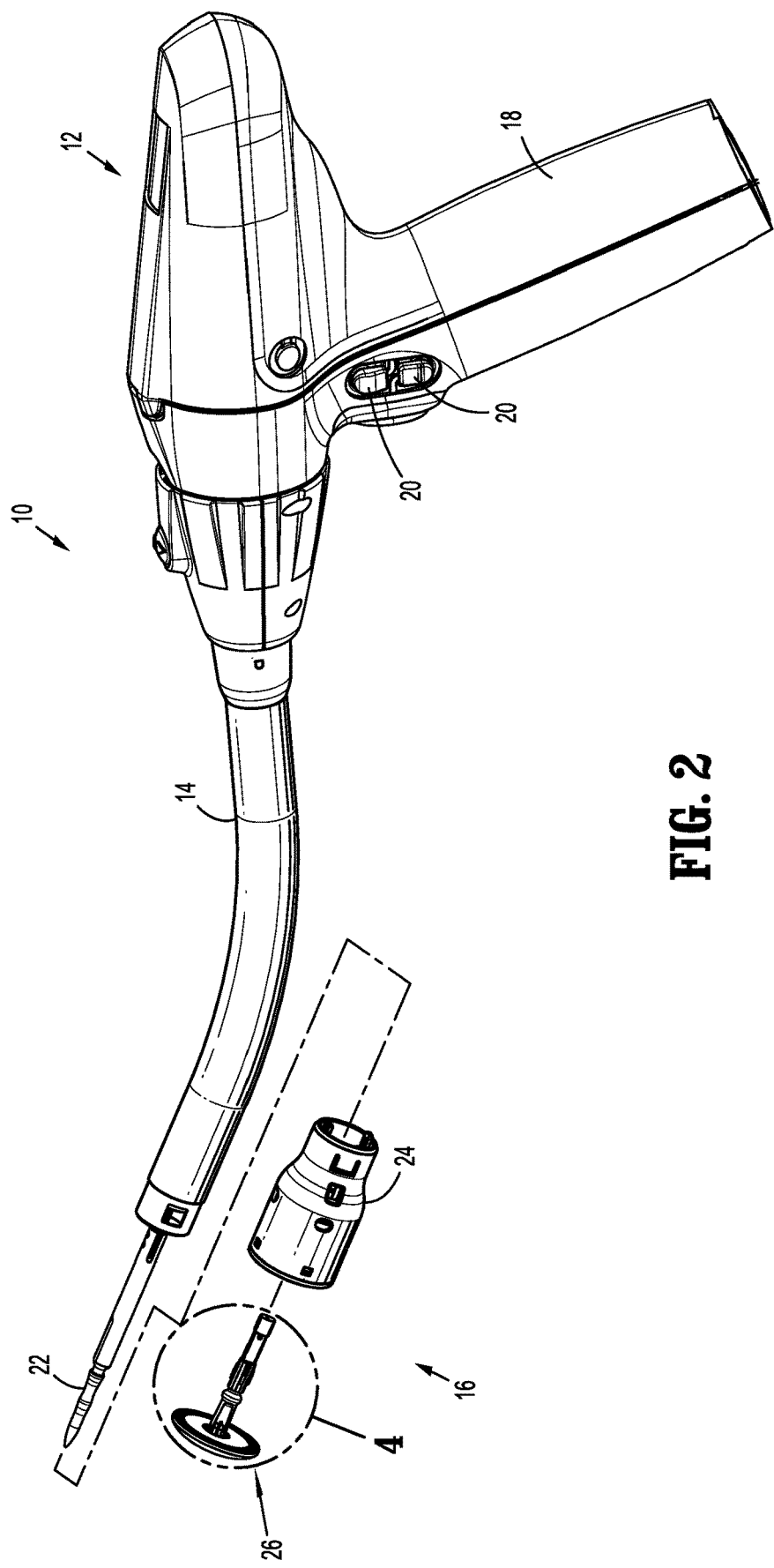
FIG. 2 is a perspective view of the circular stapling instrument illustrating a tool assembly including the anvil assembly separated from an elongate body of the circular stapling instrument.

Referring initially to FIGS. 1-2, an exemplary embodiment of a circular stapling instrument for incorporating the surgical anvil assemblies of the present disclosure is illustrated and shown generally as circular stapling instrument 10. The circular stapling instrument 10 includes a handle 12, an elongate body or adapter 14 extending from the handle 12, and a tool assembly 16 coupled to the adapter 14. The handle 12 may be electrically powered including a motor and associated gears and linkages to control operation of the stapling instrument 10. The handle 12 incorporates a grip 18 and a plurality of actuation buttons 20 which may be activated to control various functions of the stapling instrument 10 including, e.g., approximation of the tool assembly 16 and firing of staples. The grip 18 may support a battery pack (not shown) which powers the handle 12. In embodiments, the circular stapling instrument 10 may be powered via an external power source.

In embodiments, the adapter 14 is releasably coupled to the handle 12 and includes a plurality of drive mechanisms (not shown) that translate power from the handle 12 to the tool assembly 16 in response to actuation of the actuation buttons 20 to effect operation, e.g., approximation and firing, of the tool assembly 16. The adapter 14 also includes an anvil retainer 22 or trocar that extends from a distal portion of the adapter 14 and is movable between retracted and advanced positions. The anvil retainer 22 is couplable to the tool assembly 16. Commonly assigned U.S. Pat. Nos. 9,247,940; 9,055,943; and 8,806,973, and U.S. Publication No. 2015/0014392 disclose exemplary embodiments of powered handles and adapters suitable for use with the stapling instrument 10, and which are incorporated in their respective entireties by reference herein. Alternately, the elongate body or adapter 14 may be non-removably secured to the handle 12.

It is also envisioned that the handle 12 may be manually powered. Examples of manually powered handle assemblies are described in commonly assigned U.S. Pat. Nos. 8,789,737; 8,424,535; and 8,360,295 which are incorporated in their respective entireties by reference herein.

Figure 3:
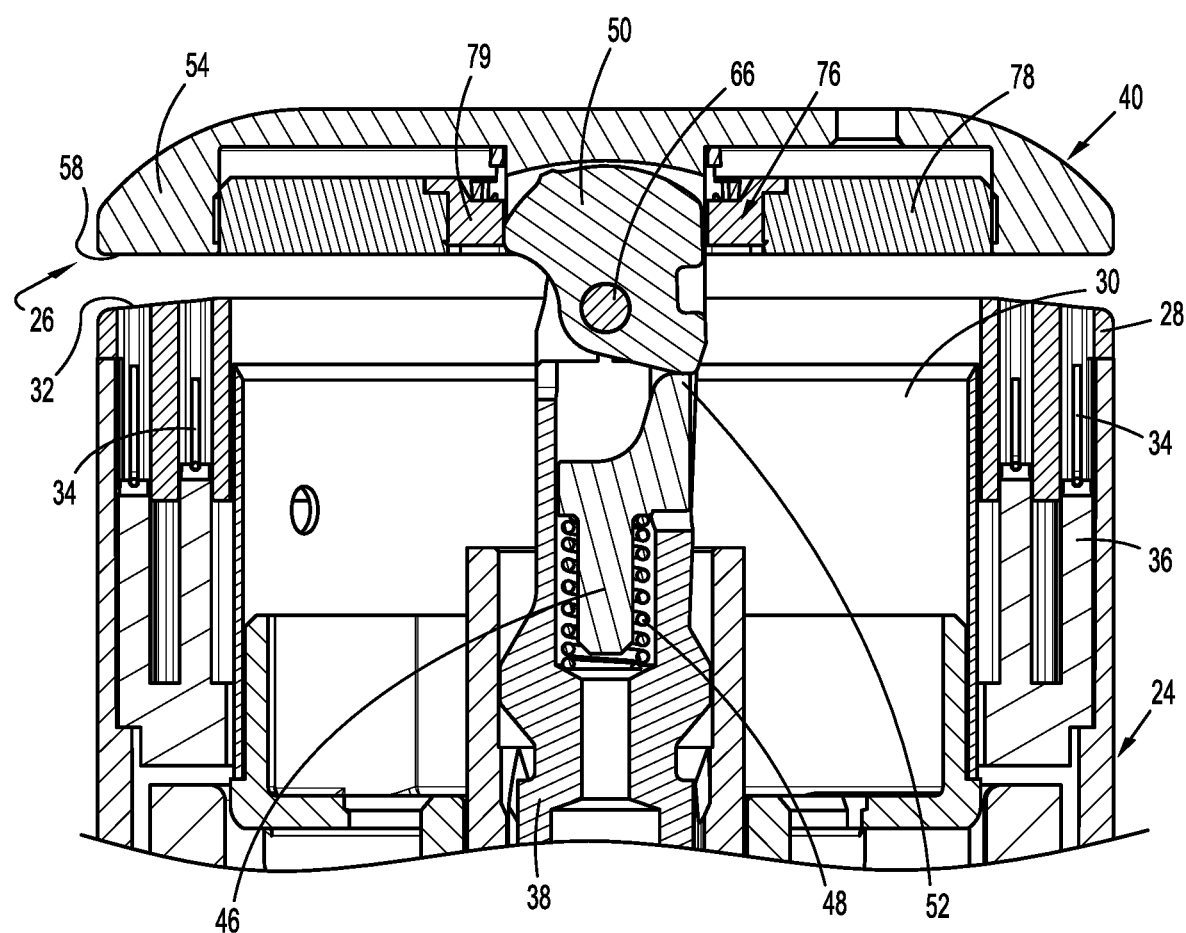
FIG. 3 is a side cross-sectional view of the tool assembly illustrating the anvil assembly mounted to the staple cartridge of a shell of the tool assembly.

Referring to FIGS. 3-5, in conjunction with FIG. 2, the tool assembly 16 includes a shell 24 and a surgical anvil assembly 26 releasably mounted to the shell 24. The shell 24 supports an annular staple cartridge 28 and an annular knife 30 internal of the staple cartridge 28. The staple cartridge 28 includes a plurality of staple receptacles 32 each accommodating an individual staple 34 and a staple pusher 36 for ejecting the staples 34 from the staple cartridge 28 upon firing of the instrument 10.

Figure 6:
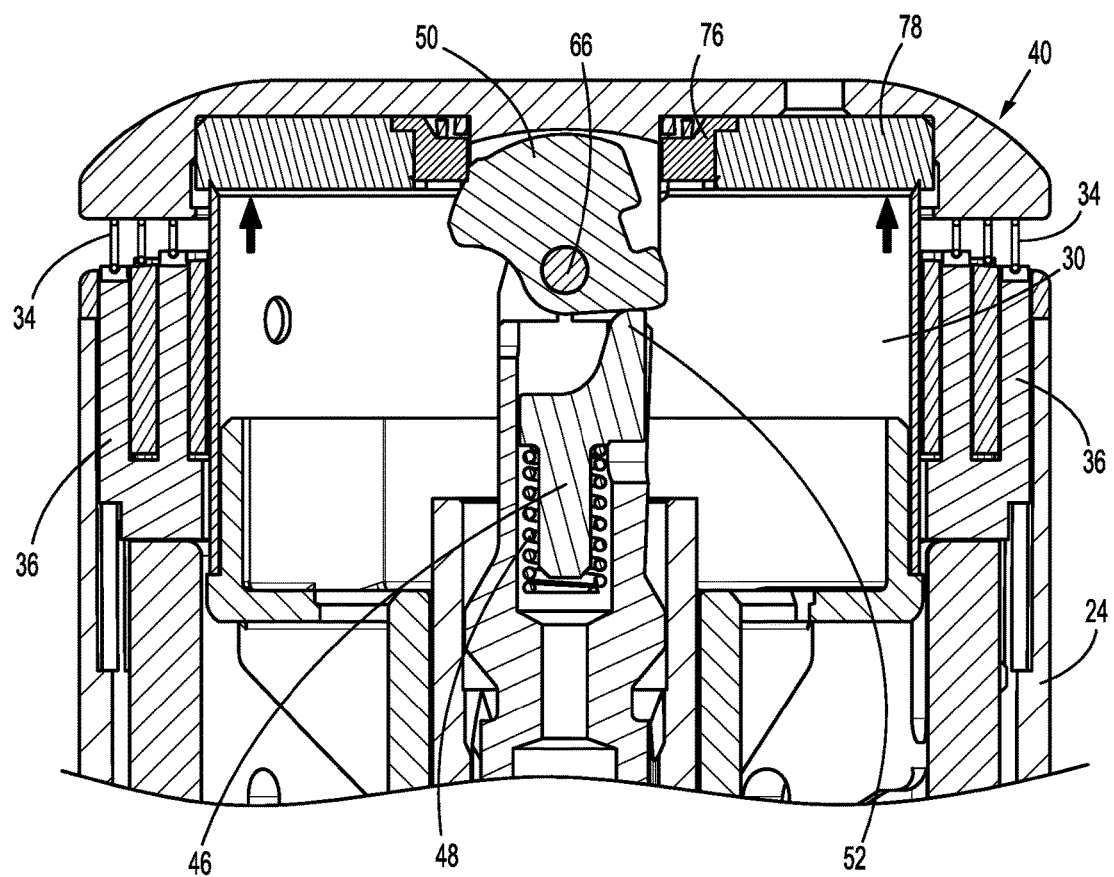
FIG. 6 is a side cross-sectional view of the tool assembly illustrating the anvil assembly mounted to the staple cartridge with an annular knife in an advanced position.
Figure 7:
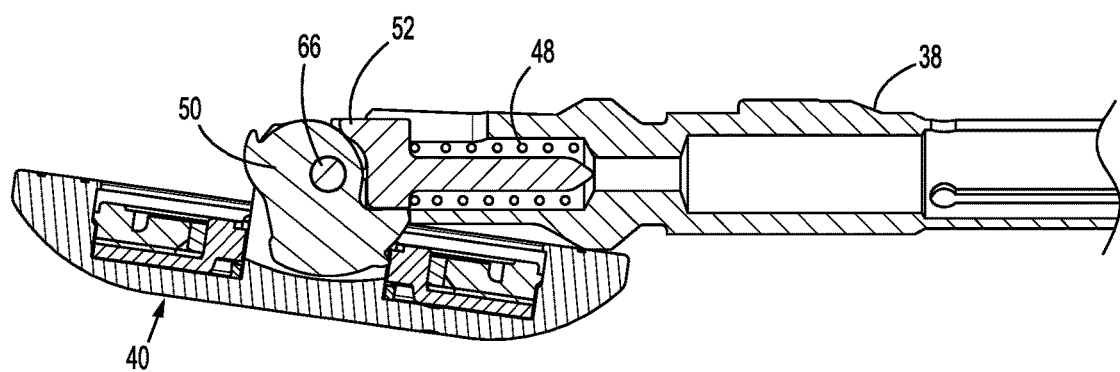
FIG. 7 is side cross-sectional view of the anvil assembly illustrating the anvil head in a pivoted or tilted condition.
Figure 8:
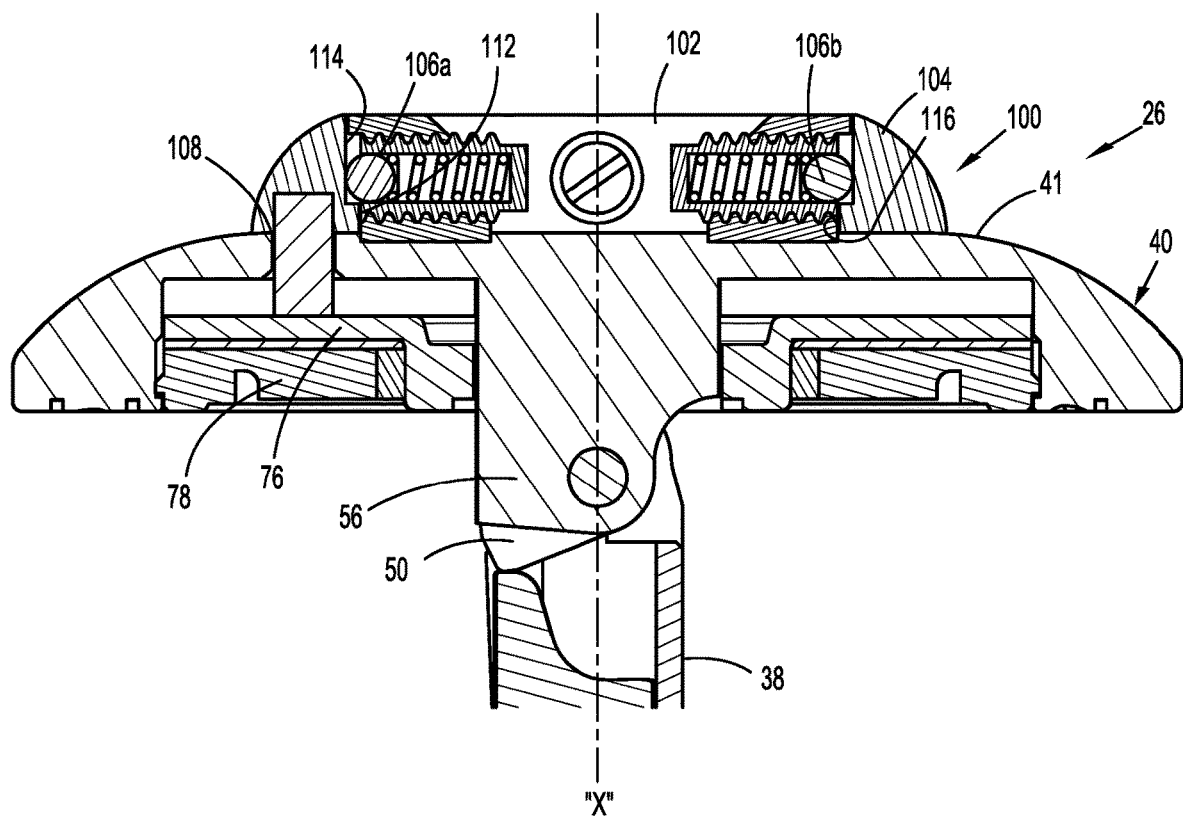
FIG. 8 is a side cross-sectional view of an embodiment of a surgical anvil assembly for incorporation into the circular stapling instrument of FIG. 1.
Figure 9A:
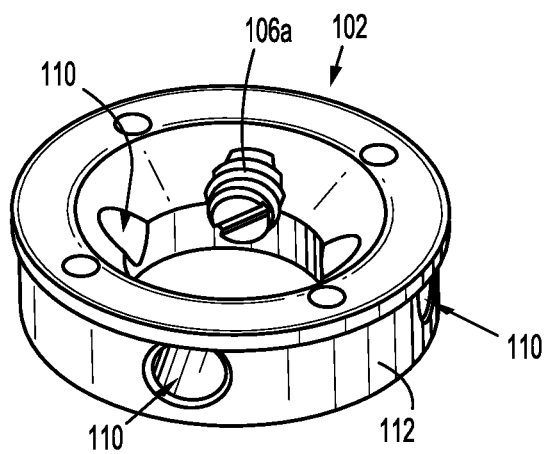
FIG. 9A is a first perspective view of an inner member of a locking assembly of the anvil assembly of FIG. 8.
Figure 9B:
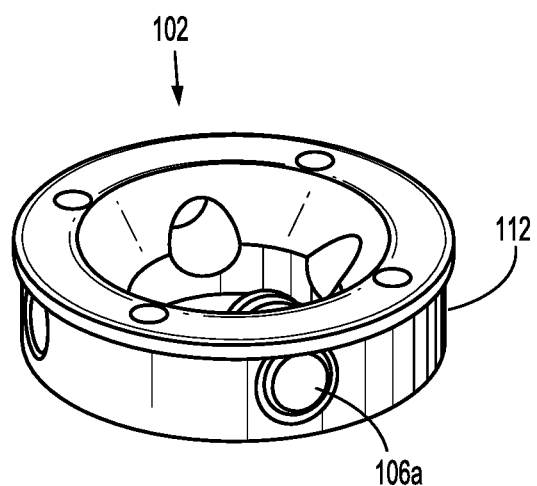
FIG. 9B is a second perspective view of the inner member of the locking assembly.
Figure 10:
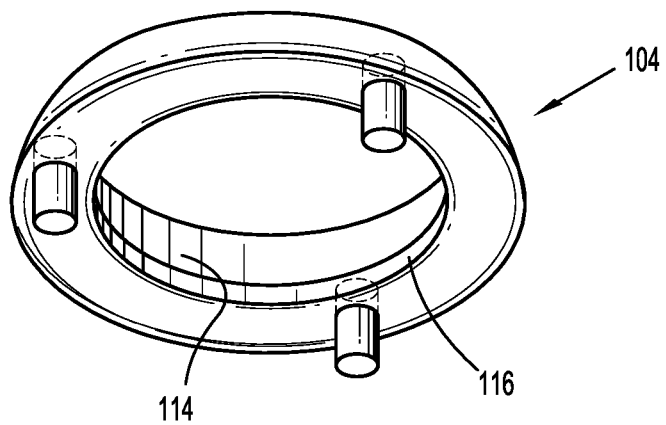
FIG. 10 is a perspective view of an outer member of the locking assembly of FIG. 8.

The anvil assembly 26 shares common features with the anvil assembly disclosed in commonly assigned U.S. Pat. No. 8,540,132, the entire contents of which are incorporated by reference herein. As best depicted in FIGS. 3-5, the anvil assembly 26 includes an anvil center rod 38 and an anvil head 40 pivotally mounted to the anvil center rod 38. The anvil head 40 is adapted to pivot between a first operative condition as depicted in FIGS. 4 and 6, and a second pivoted or tilted condition as depicted in FIG. 7. The anvil center rod 38 includes a pair of distal spaced arms 42 having transverse bores 44 that receive a pivot member, such as, for example, a pivot pin 66, therethrough. The anvil head 40 is pivotably coupled to the distal spaced arms 42 via the pivot pin 66.

The anvil assembly 26 further includes a plunger 46, a plunger spring 48, and a cam latch or cam plate 50. The plunger 46 is at least partially received within the anvil center rod 38, e.g., between the spaced arms 42, and is spring biased in a distal direction by the plunger spring 48. The plunger 46 includes a plunger finger 52, which engages the cam latch 50 to provide a distally-oriented force on the cam latch 50.

The anvil head 40 includes a housing 54 defining a recess 70 therein, and a post 56 extending proximally from a center of the housing 54. The housing 54 has an anvil tissue contact surface 58 defining a plurality of staple deforming pockets 72. The post 56 of the anvil head 40 includes a pair of spaced post arms 60 defining a slot 62 and transverse bores 64 extending through the spaced post arms 60. As briefly mentioned above, the anvil center rod 38 is at least partially positioned about the post 56 and coupled to the anvil head 40 through the pivot member 66 which extends through respective transverse bores 44, 64 of the distal spaced arms 42 of the anvil center rod 38 and the post 56 to pivotally couple the anvil head 40 to the anvil center rod 38. In addition, the cam latch 50 is received within the slot 62 of the post 56 and coupled to the anvil center rod 38 and the post 56 via the pivot member 66 which extends through a pin opening 68 of the cam latch 50.

Referring now to FIGS. 4-6, the anvil assembly 26 further includes a backup member 76 and a cut ring 78 attached thereto. The backup member 76 and the cut ring 78 are moved together within the recess 70 of the anvil head 40 upon application of a force thereto, e.g., during advancement of the annular knife 30 of the tool assembly 16 during firing of the instrument 10. The backup member 76 includes an annular body 79 and a pair of diametrically opposed fingers 98 extending radially inward from the annular body 79. The annular body 79 of the backup member 76 is axially movable, but pivotally fixed within the recess 70 of the anvil head 40.

The fingers 98 are engaged by the spaced arms 42 of the anvil center rod 38 to prevent the backup member 76 from moving in a proximal direction and to maintain the anvil head 40 in the operative condition (e.g., untilted) until the annular knife 30 is actuated. More specifically, when the backup member 76 is in the proximal position, as shown in FIG. 3, the fingers 98 of the backup member 76 sit on or abut a distal surface of the spaced arms 42 of the anvil center rod 38, whereby rocking or pivotal movement of the anvil head 40 relative to the anvil assembly 26 is prevented. Pivotal movement of the anvil head 40 relative to the anvil center rod 38 is permitted only after the fingers 98 are distally spaced from the arms 42 of the anvil center rod 38.

The backup member 76 further includes a pair of diametrically opposed cam shelves 99 extending radially inward from the annular body 79. The cam shelves 99 capture the cam latch 50 therebetween to rotationally fix the cam latch 50 to the backup member 76. In this way, as the cam latch 50 rotates or pivots, so does the backup member 76 and the anvil head 40 as a whole. The backup member 76 may be formed from a hard material such as metal, although other materials of construction are envisioned.

The cut ring 78 of the anvil assembly 26 includes a disc-shaped annular body 104 defining a central aperture 106 for reception of the backup member 76. Thus, movement of the backup member 76 between the untilted and tilted conditions causes corresponding movement of the cut ring 78. In embodiments, the cut ring 78 may be formed through a molding process, e.g., an injection molding process, and may be fabricated from a material having a durometer which permits the annular knife 30 to pierce through the annular body 104 and bottom out against the backup member 76. Suitable materials of the cut ring 78 include polypropylene or polyester. Other materials are contemplated.

Prior to firing of the stapling instrument 10, the backup member 76 is in its retracted or proximal position with the cut ring 78 secured to the backup member 76 in the aforedescribed manner. With the backup member 76 in the proximal position, the inwardly extending fingers 98 of the backup member 76 are engaged by the spaced arms 42 (FIG. 4) of the anvil center rod 38, such that the anvil head 40 is retained in the operative condition. As described above, the plunger finger 52 of the plunger 46 of the anvil center rod 38 is positioned to urge the cam latch 50 and the anvil head 40 about the pivot member 66 towards the tilted condition (FIG. 7). However, the anvil head 40 is prevented from pivoting until the annular knife 30 is advanced to unlock a locking assembly 100 (FIGS. 4, 5, and 8-12) of the surgical anvil assembly 26, as will be described.

With reference to FIGS. 8-12, the surgical anvil assembly 26 may further include a locking assembly 100 for selectively locking the anvil head 40 in each of the first, operative condition, and the second, tilted condition. The locking assembly 100 replaces the deformable retainer members of the prior art, such as the retainer member 127 described in U.S. Pat. No. 9,532,781, the entire contents of which being incorporated by reference herein. The deformable retainer members typically support the backup member 76 in the proximal position and deform upon advancement of the backup member 76 to allow for tilting of the anvil head 40. Due to the absence of the deformable retainer in the present embodiment, the anvil head 40 is capable of repeated movement between the untilted and tilted conditions.

The locking assembly 100 generally includes an annular inner member or housing 102, an annular outer member 104 surrounding the inner member 102, and a pair of locking elements 106a, 106b movably coupled to the inner member 102. In embodiments, the inner and outer members 102, 104 may assume any suitable shape, such as, for example, ring-shaped, squared, triangular, or the like. The inner member 102 is fixedly supported on a distally-facing outer surface 41 of the anvil head 40. The anvil head 40 may have a plurality of holes 108 (FIG. 8) defined therethrough for receipt of fasteners (not explicitly shown) that fixedly attach the inner member 102 of the locking assembly 100 to the anvil head 40. The inner member 102 defines a plurality of passageways 110 defined transversely therethrough for housing a respective locking element 106a or 106b. While four passageways 110 are illustrated, it is contemplated that the inner member 102 may have more or less than four passageways 110 for accommodating a respective number of locking elements 106a, 106b.

The locking elements 106a, 106b are received in the passageways 110 of the inner member 102 and are arranged in diametrical opposition to one another. The locking elements 106a, 106b may be ball detents that protrude radially outward from an outer periphery 112 of the inner member 102. In embodiments, the locking elements 106a, 106b may be any suitable biasing member that is resiliently, radially-outwardly biased. In embodiments, the locking elements 106a, 106b may remain fixed relative to the inner member 102 whereas the outer member 104 may be flexible, such that the outer member 102 flexes outwardly upon contacting the locking element 106a, 106b as the outer member 104 slides along the inner member 102, as will be described.

The outer member 104 of the locking assembly 100 surrounds the inner member 102 and is slidable relative thereto along a longitudinal axis "X" between a first, proximal position (FIG. 11), in which the outer member 104 abuts the outer surface 41 of the anvil head 40, and a second, distal position (FIG. 12), in which the outer member 104 is distally spaced from the outer surface 41 of the anvil head 40. The outer member 104 has an inner surface or inner periphery 114 that is adjacent to and surrounds the outer periphery 112 of the inner member 102. The inner periphery 114 of the outer member 104 has a lip or ledge 116 protruding radially inward therefrom for selective interaction with the locking elements 106a, 106b.

More particularly, in the first, proximal position (FIG. 11), the lip 116 of the outer member 104 is disposed proximally of an outer surface of the locking elements 106a, 106b while also overlapping therewith. Due to the lip 116 of the outer member 104 overlapping the locking elements 106a, 106b, the locking elements 106a, 106b resist distal movement of the outer member 104 relative to the inner member 102. To distally move the outer member 104 of the locking assembly 100, a threshold force oriented in the distal direction must be applied to the outer member 104 to overcome the spring force of the locking elements 106a, 106b. Upon application of the threshold force, the locking elements 106a, 106b are moved radially inward relative to the inner member 102, allowing the lip 116 of the outer member 104 to pass over the locking elements 106a, 106b.

When the outer member 104 is in the second, distal position (FIG. 12), the locking elements 106a, 106b and the lip 116 of the outer member 104 are engaged and aligned along a transverse axis. Since the locking elements 106a, 106b exhibit an outwardly-oriented spring bias, the lip 116 of the outer member 104 and the locking elements 106a, 106b are frictionally engaged with one another, thereby resisting movement of the outer member 104 from the second, distal position until the threshold force is applied in the proximal direction.

The locking assembly 100 further includes a plurality of posts or rods 118 interconnecting the inner member 102 of the locking assembly 100 and the backup member 76. The posts 118 are circumferentially spaced from one another and extend downwardly (e.g., proximally) from the outer member 104. The posts 118 have a distal end 118b attached to or formed with the outer member 104, an intermediary portion 118c extending through a respective hole 108 defined through the anvil head 40, and a proximal end 118a disposed within the recess 70 of the anvil head 40. The proximal end 118a of each of the posts 118 is fixed to the backup member 76, such that the backup member 76 moves with the outer member 104 as the outer member 104 moves relative to the inner member 102. Accordingly, as the outer member 104 moves from the first, proximal position (FIG. 11) toward the second, distal position (FIG. 12), the backup member 76 moves deeper into the recess 70 of the anvil head 40 and out of engagement with the distal spaced arms 42 of the anvil center rod 38.

In operation, the backup member 76 with the cut ring 78 is maintained in the recess 70 in the proximal position by the locking assembly 100. In particular, the locking elements 106a, 106b resist distal movement of the outer member 104 of the locking assembly 100 relative to the inner member 102 of the locking assembly 100. Since the backup member 76 is fixed to the outer member 104 via the posts 118 of the locking assembly 100, distal movement of the backup member 76 toward the distal position is also resisted.

Figure 11:
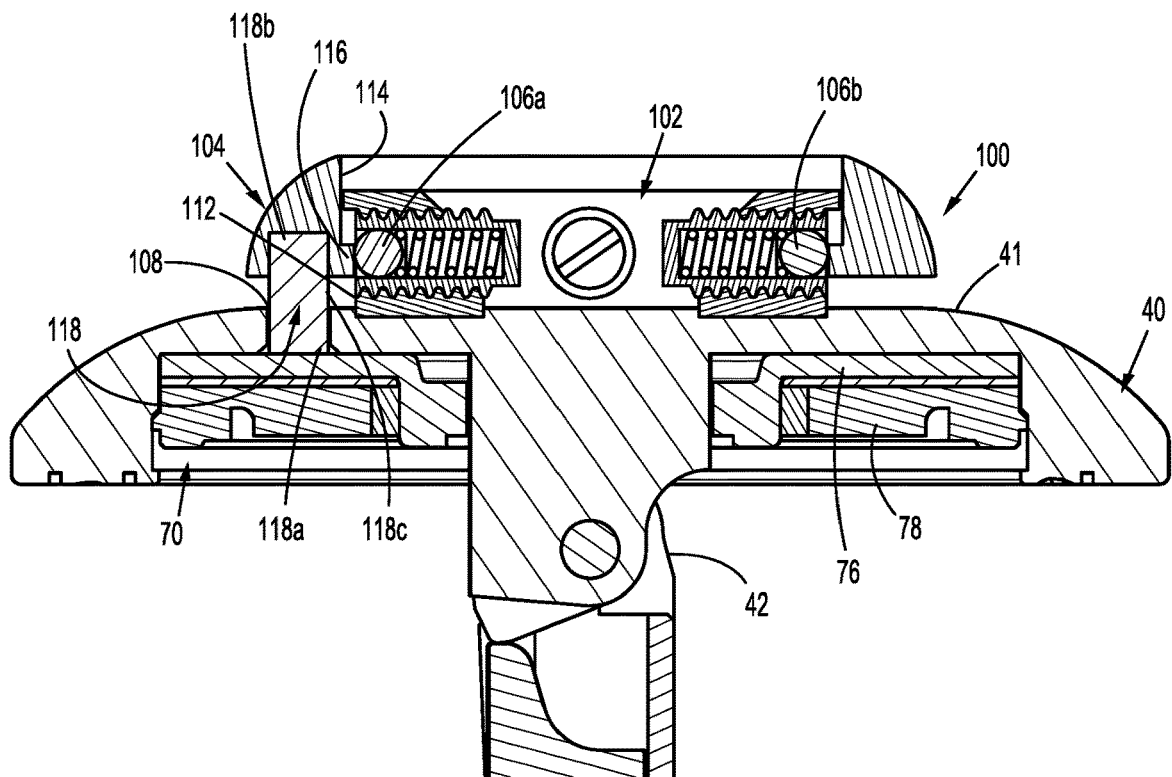
FIG. 11 is a side cross-sectional view of the anvil assembly of FIG. 8 illustrating the locking assembly in a distal position.
Figure 12:
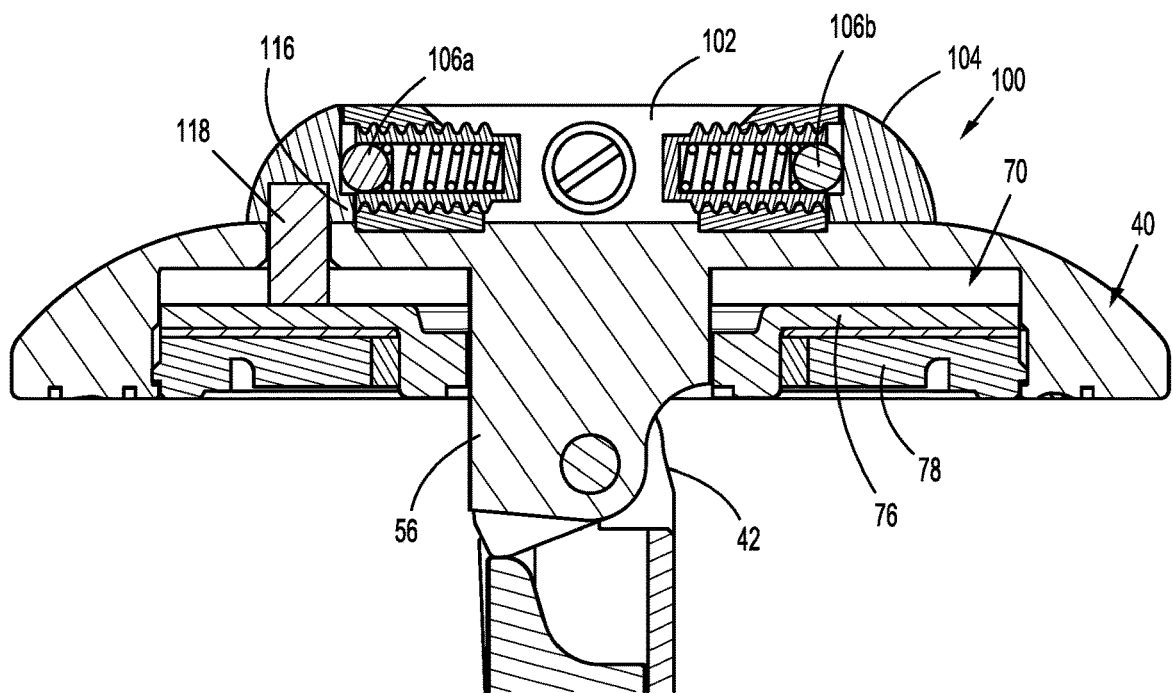
FIG. 12 is a side cross-sectional view of the anvil assembly of FIG. 8 illustrating the locking assembly in a proximal position.

When the anvil head 40 and the staple cartridge 28 (FIG. 3) of the shell 24 are approximated, the stapling instrument 10 may be fired to advance the annular knife 30 within the shell 24 from a retracted position recessed within the shell 24 to an advanced position extending into the cut ring 78 of the anvil assembly 26. As the annular knife 30 engages the cut ring 78, the cut ring 78 and the backup member 76 exert a distally-oriented force on the outer member 104 of the locking assembly 100 via the posts 118 of the locking assembly 118. Upon applying the threshold force on the outer member 104, the locking element(s) 106a, 106b are forced radially-inward into the respective passageways 110 of the inner member 102, allowing the lip 116 of the outer member 104 to pass over the locking elements 106a, 106b as the backup member 76 is advanced to the second, distal position within the recess 70 of the anvil head 40, as shown in FIG. 11. Once the backup member 76 moves towards its second position, the lip 116 of the outer member 104 and the locking elements 106a, 106b frictionally engage one another to selectively fix the outer member 104 and, in turn, the backup member 76 in the second, distal position.

As the backup member 76 is moved toward its distal position, the fingers 98 (FIGS. 4 and 5) of the backup member 76 disengage the distal spaced arms 42 of the anvil center rod 38, freeing the anvil head 40 to pivot relative to the anvil center rod 38. With the anvil head 40 free to rotate, the plunger spring 48 (FIG. 6) urges the plunger 46 in a distal direction whereby the plunger finger 52 engages the cam latch 50 to rotate the cam latch 50 and the anvil head 40 about the pivot member 66 to permit the anvil head 40 to assume the second tilted condition depicted in FIG. 7.

After the anvil head 40 is moved to the tilted condition, the anvil head 40 may be manually moved back towards the first, operative condition. After moving the anvil head 40 back to the first, operative condition (e.g., untilted), the backup member 76 may also be reset to its proximal position. To move the backup member 76 to the proximal position, a proximally-oriented threshold force may be manually applied to the outer member 104 of the locking assembly 100, which overcomes the static friction between the lip 116 of the outer member 104 and the locking elements 106a, 106b, whereby the outer member 104 moves proximally relative to the inner member 102. Due to the interconnection between the outer member 104 and the backup member 76 via the posts 118, the backup member 76 moves proximally with the outer member 104 back toward the proximal position.

Upon re-entering the proximal position, the fingers 98 (FIGS. 4 and 5) of the backup member 76 re-engage the distal spaced arms 42 of the anvil center rod 38, thereby stabilizing the anvil head 40 in the first, operative condition. It is contemplated that this process of selectively moving the anvil head 40 relative to the anvil center rod 38 may be repeated indefinitely.

With reference to FIGS. 13-19, another embodiment of a surgical anvil assembly 126 is illustrated, similar to the anvil assembly 26 described above. Due to the similarities between the anvil assembly 126 of the present embodiment and the anvil assembly 26 described above, only those elements of the anvil assembly 126 deemed necessary to elucidate the differences from anvil assembly 26 will be described in detail.

Figure 13:
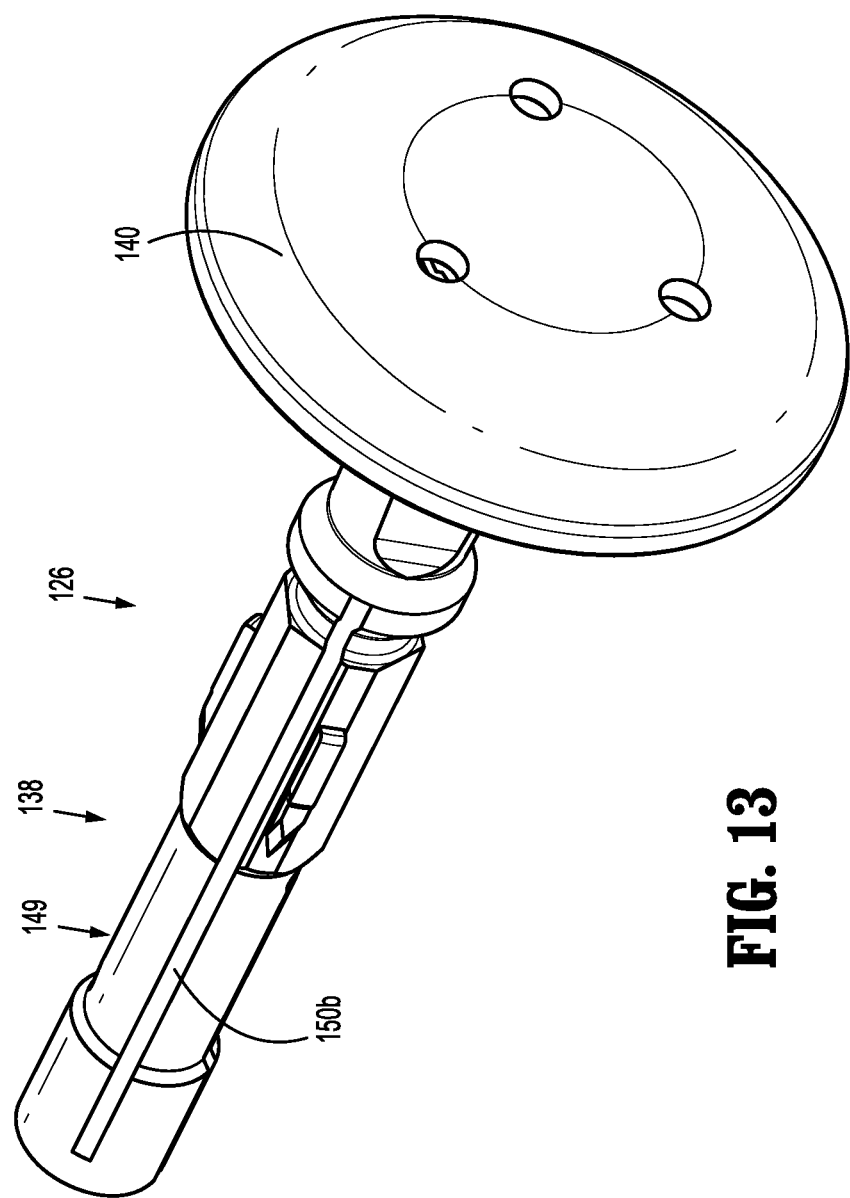
FIG. 13 is a perspective view of another embodiment of a surgical anvil assembly for incorporation into the circular stapling instrument of FIG. 1.
Figure 14:
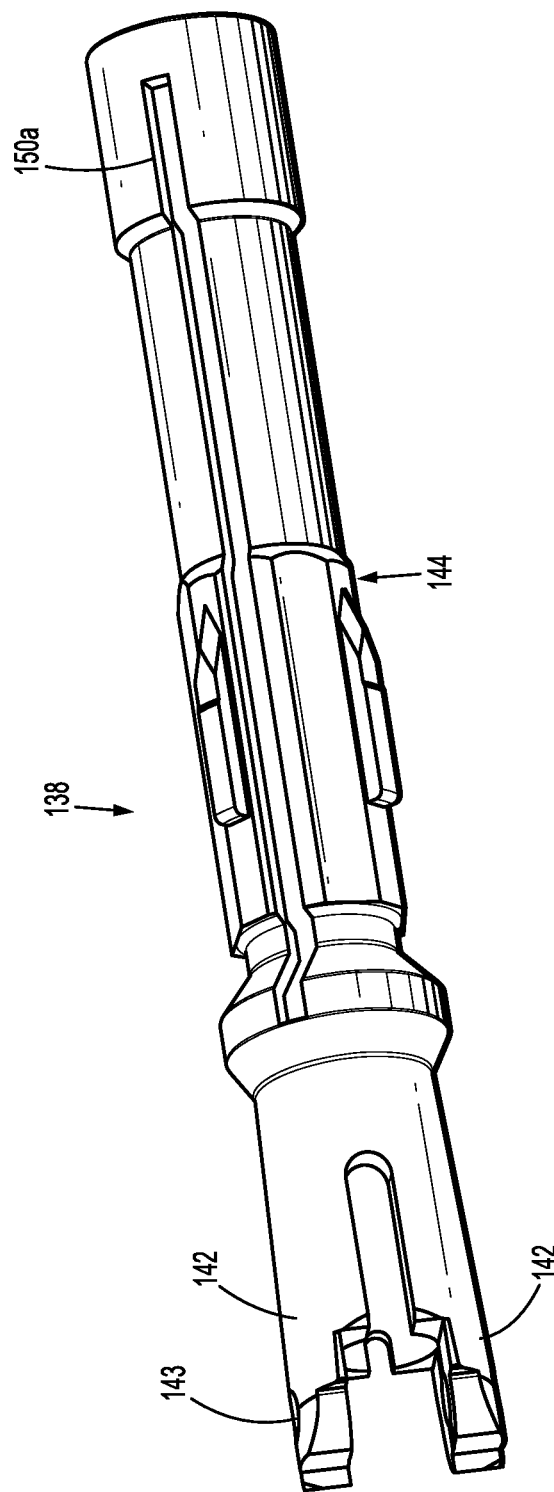
FIG. 14 is a side, perspective view of an anvil center rod of the anvil assembly of FIG. 13.
Figure 15:
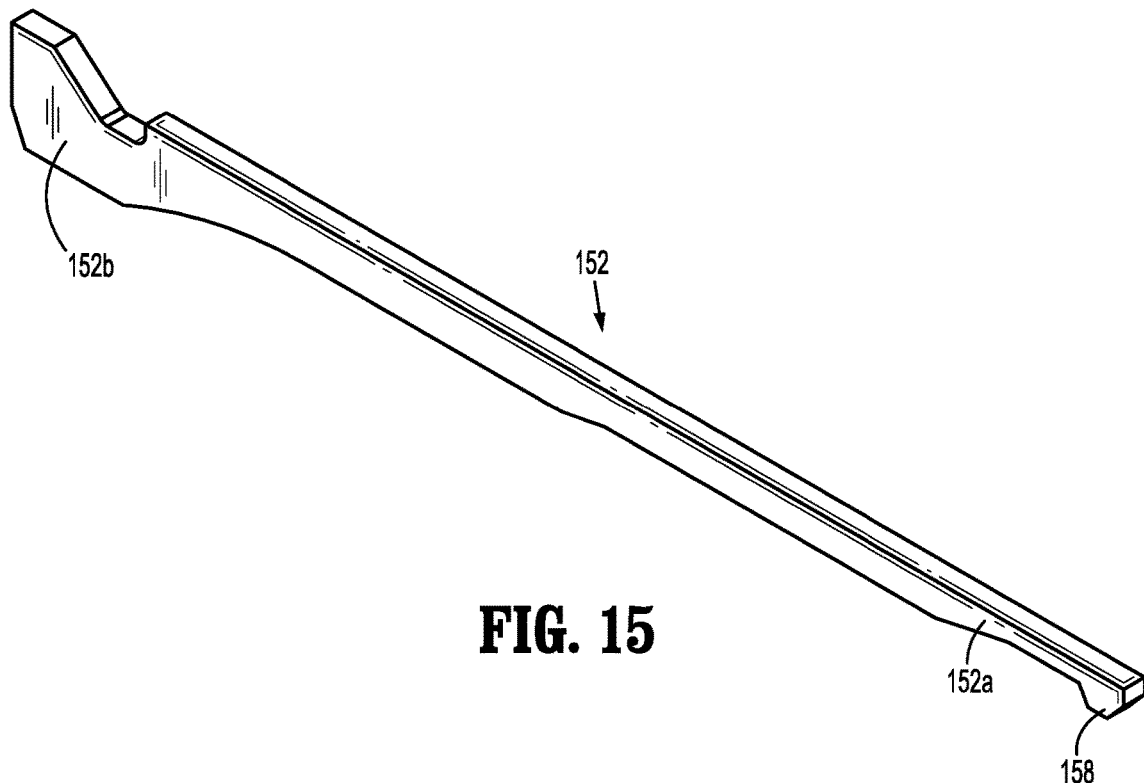
FIG. 15 is a perspective view of a resilient leg of the anvil assembly of FIG. 13.
Figure 16:
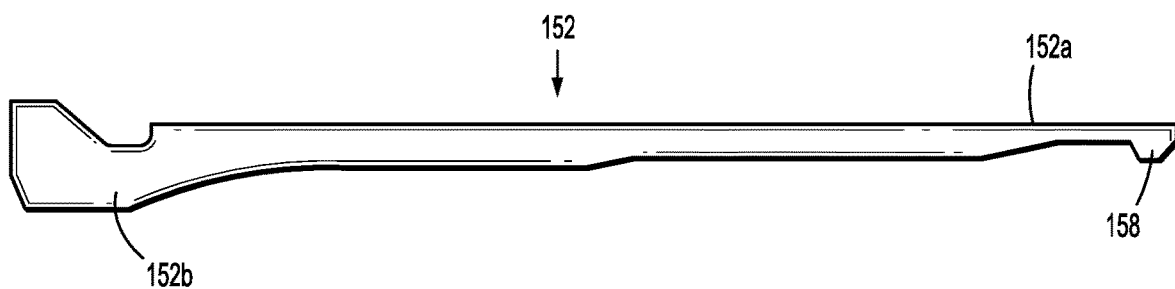
FIG. 16 is a side view of the resilient leg of FIG. 15.

With specific reference to FIGS. 13 and 14, the anvil assembly 126 includes an anvil center rod 138 and an anvil head 140, similar to the anvil head 40 described above. The anvil head 140 is pivotally mounted to the anvil center rod 138. The anvil center rod 138 may include a pair of distal spaced arms 142 and an elongated proximal body portion 144 extending proximally from the pair of distal spaced arms 142. The distal spaced arms 142 define transverse bores 143 through a distal end thereof for receiving a pivoting member (not explicitly shown), similar to the pivot member 66 described above. The proximal body portion 144 of the anvil center rod 138 is configured to releasably couple to an anvil retainer or trocar, such as, for example, the anvil retainer 22 shown in FIG. 2. A detailed description of an anvil retainer may be found in U.S. Pat. No. 7,364,060, the entire contents of which being incorporated by reference herein.

The proximal body portion 144 of the anvil center rod 138 defines a pair of diametrically opposed slots 150a, 150b. The slots 150a, 150b extend proximally from a location adjacent a proximal end of the distal spaced arms 142 and terminate distally of a proximal end of the proximal body portion 144. The slots 150a, 150b are dimensioned for receipt of a pair of legs 152, 154 configured to releasably capture the anvil retainer 22 therebetween, as will be described below.

With reference to FIGS. 15-19, the legs 152, 154 of the anvil center rod 138 are received within a respective slot 150a, 150b in the proximal body portion 144 of the anvil center rod 138. Each of the legs 152, 154 is fabricated from a material that allows the legs 152, 154 to flex about proximal ends 152a, 154a thereof in a spring-like manner. It is contemplated that the thickness of the legs 152, 154 may be increased or decreased to adjust the flexibility thereof. Distal ends 152b, 154b of the legs 152, 154 are attached to an inner periphery 156 of the proximal body portion 144 via, for example, laser welding, whereas proximal ends 152a, 154a of the legs 152, 154 are free to pivot relative to the respective distal end 152b, 154b.

In embodiments, the legs 152, 154 may be attached to the proximal body portion 144 along any suitable location of the legs 152, 154 using any suitable fastening method. As can be appreciated, adjusting the location at which the legs 152, 154 are attached to the proximal body portion 144 changes the force required to flex the legs 152, 154. The proximal ends 152a, 154a of the legs 152, 154 include a tab or detent 158, 160 that extends radially inward. The detents 158, 160 are configured for snap fit engagement with a lip 23 defined by a proximal end of the trocar 22, as will be described in further detail below.

Each of the legs 152, 154 has an outer profile that matches the outer profile of the proximal body portion 144 so that the legs 152, 154 do not protrude outwardly from the proximal body portion 144. Each of the legs 152, 154 has an inner profile that substantially matches an outer profile of the trocar 22. As such, when the legs 152, 154 are disposed within the respective slots 150a, 150b of the proximal body portion 144, the legs 152, 154 cooperatively define a cavity 162 therebetween dimensioned for receipt of the trocar 22.

Figure 19:
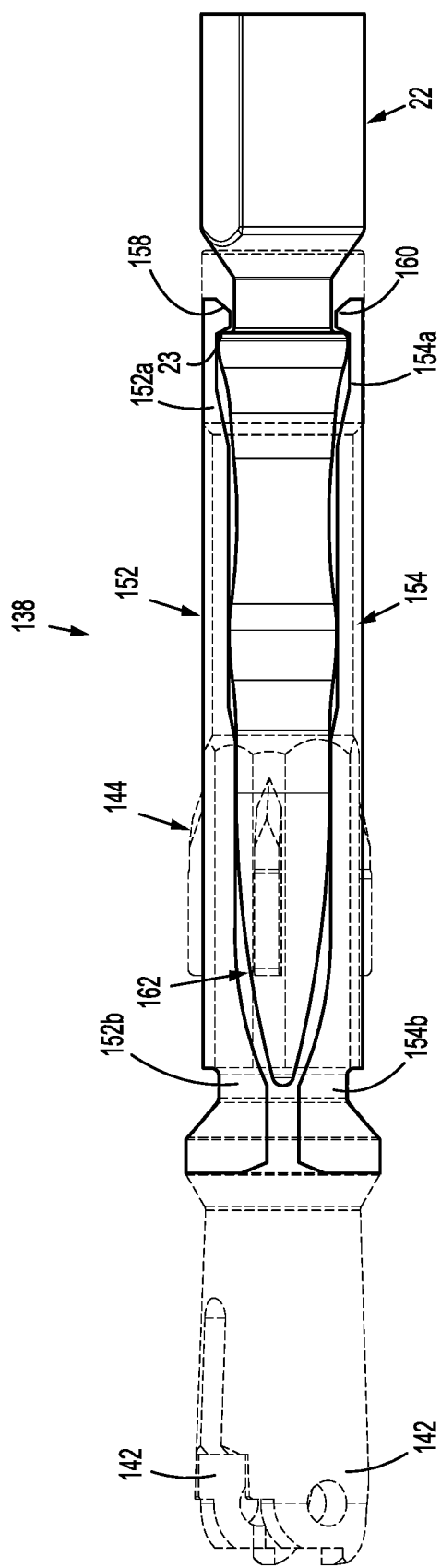
FIG. 19 is a perspective view, with parts shown in phantom, of the trocar fully inserted into the anvil center rod of FIG. 14.

During manufacture, the legs 152, 154 are received within a respective slot 150a, 150b of the proximal body portion 144, and the distal end 152b, 154b of each of the legs 152, 154 is welded (e.g., laser welded) to the inner periphery 156 (FIG. 18) of the proximal body portion 144. As shown in FIGS. 17 and 18, the trocar 22 is distally advanced, in the direction indicated by arrows "A" in FIG. 18, through the proximal body portion 144, whereby a tapered outer surface 25 of the base of the trocar 22 engages the detents 158, 160 at the proximal end 152a, 154a of the legs 152, 154, causing the legs 152, 154 to flex outwardly. As shown in FIG. 19, distal advancement of the trocar 22 is continued until the lip 23 defined at the base of the trocar 22 passes over the detents 158, 160 of the legs 152, 154, such that the detents 158, 160 snap into place proximally of the lip 23 of the trocar 22, capturing the trocar 22 in the cavity 162 defined between the legs 152, 154. The inwardly-oriented resilient bias of the legs 152, 154 axially fixes the trocar 22 within the proximal body portion 144.

With reference to FIGS. 20-23, another embodiment of a surgical anvil assembly 226 is illustrated, similar to the anvil assemblies described above. Due to the similarities between the anvil assembly 226 of the present embodiment and the anvil assemblies described above, only those elements of the anvil assembly 226 deemed necessary to elucidate the differences from the other anvil assemblies will be described in detail.

The anvil assembly 226 includes an anvil center rod 238, an anvil head 240 pivotally mounted to the anvil center rod 238, and a ring assembly 250 for selectively unlocking the anvil head 240 from the anvil center rod 238. The anvil head 240 is configured to pivot relative to the anvil center rod 238 between a first operative condition and a second pivoted or tilted condition. The anvil head 240 defines a recess 270 therein having a post 256 of the anvil head 240 extending proximally therefrom. The post 256 of the anvil head 240 is pivotally coupled to a distal end of the anvil center rod 238.

The ring assembly 250 is received within the recess 270 defined in the anvil head 240 and generally includes a backup member 276 and a cut ring 278 disposed about and secured to the backup member 276. The ring assembly 240 is movable within the recess 270 of the anvil head 240 upon application of a force thereto, e.g., during advancement of an annular knife, such as, for example, the annular knife 30 shown in FIGS. 3 and 6. The backup member 276 of the ring assembly 250 has a ring body 279 and an annular lip 252 extending radially outward from a distal end of the ring body 279 to support the cut ring 278 thereon. The ring body 279 defines a central opening 294 for reception of the post 256 of the anvil head 240. The central opening 294 is dimensioned to allow movement of the backup member 276 about the post 256 from a pre-fired, retracted or proximal position (FIG. 20) to a post-fired, advanced or distal position (FIG. 23) within the recess 70 of the anvil head 40.

The backup member 276 further includes a pair of diametrically opposed fingers 298 extending inwardly from the ring body 279 into the central opening 294. The fingers 298 are engaged by a distal end of the anvil center rod 238 to prevent the backup member 276 from moving in a proximal direction and to maintain the anvil head 40 in the operative condition (e.g., untilted), in a similar manner described above. Pivotal movement of the anvil head 240 relative to the anvil center rod 238 is permitted only after the fingers 298 are distally spaced from the distal end of the anvil center rod 238. The backup member 276 is restricted from moving distally out of the proximal position by a frangible portion 254 of the cut ring 278, as will be described below. The backup member 276 may be formed from a hard material such as metal, although other materials of construction are envisioned.

The cut ring 278 of the ring assembly 250 includes a disc-shaped annular body 257 defining a central aperture 258 for reception of the backup member 276. The annular body 257 may be press fit onto the backup member 276. Thus, movement of the backup member 276 between proximal and distal positions causes corresponding movement of the cut ring 278. In embodiments, the cut ring 278 may be formed through a molding process, e.g., an injection molding process, and may be fabricated from a material having a durometer which permits the annular knife 30 to pierce through the annular body 257 and bottom out against the annular lip 252 of the backup member 276. In embodiments, the cut ring 278 may be fabricated from a material that prevents advancement of the annular knife 30 therethrough and is instead coated with a material that permits advancement of the annular knife 30 therethrough. Suitable materials for the cut ring 278 include polytetrafluoroethylene, polypropylene or polyester. Other materials are contemplated.

Figure 20:
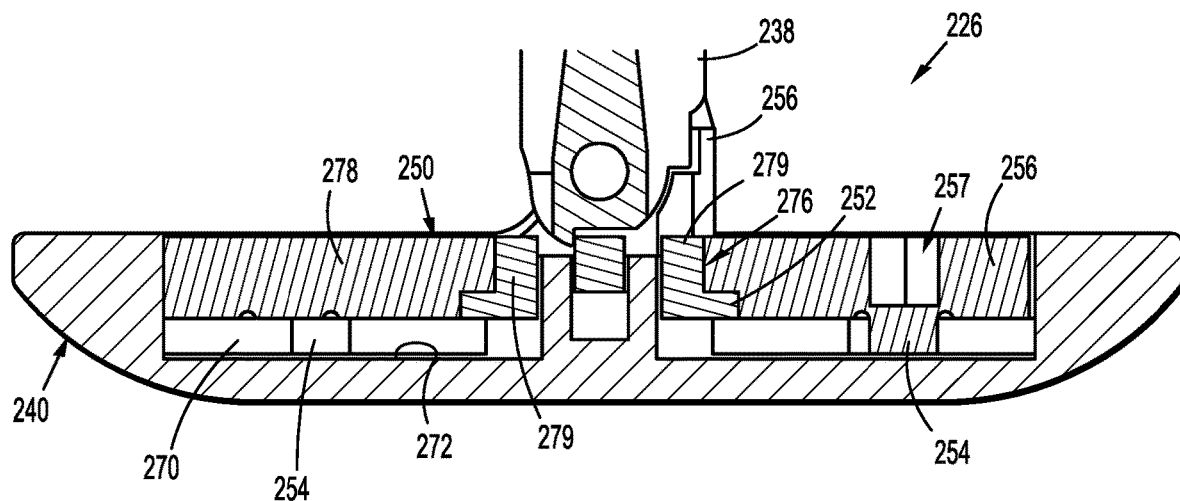
FIG. 20 is a side cross-sectional view of another embodiment of a surgical anvil assembly for incorporation into the circular stapling instrument of FIG. 1.
Figure 21:
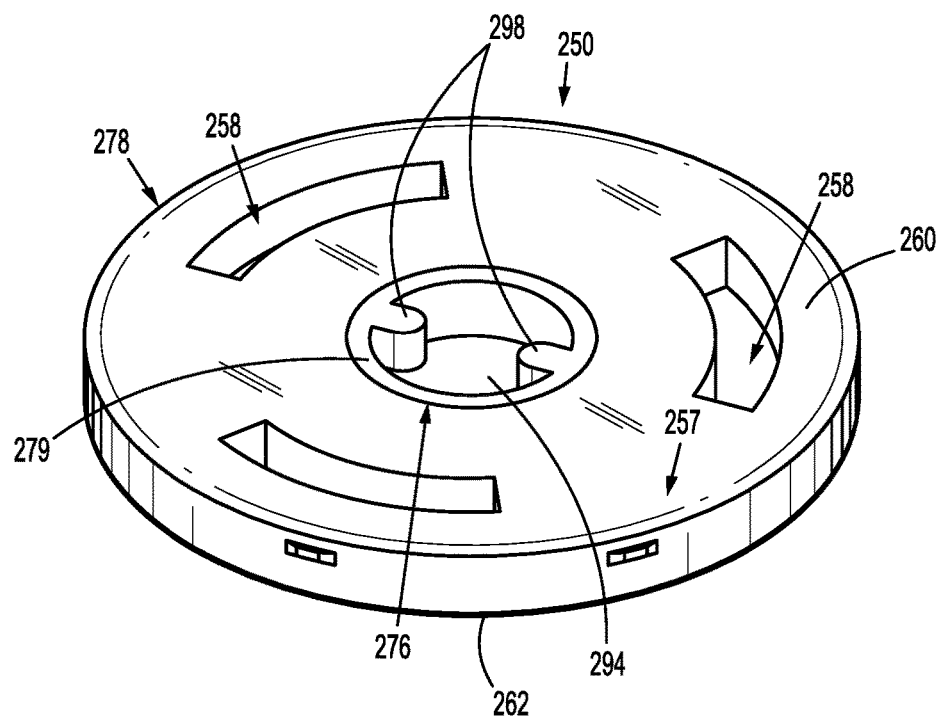
FIG. 21 is a perspective view of a proximal side of a ring assembly of the anvil assembly of FIG. 20.
Figure 22:
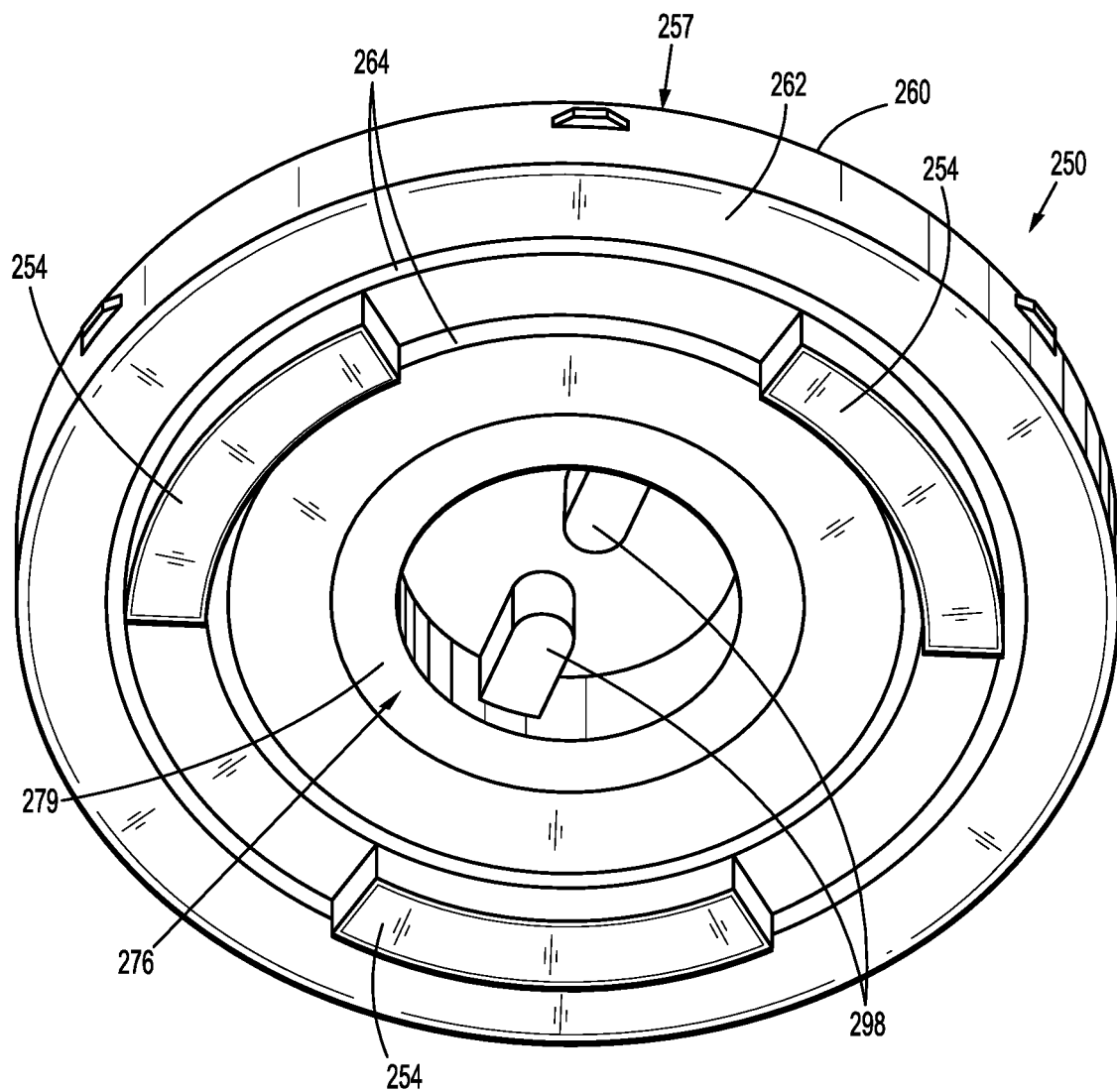
FIG. 22 is a perspective view of a distal side of the ring assembly of FIG. 21.

As best shown in FIG. 21, the cut ring 278 includes a plurality of pockets 258 formed in a bottom or proximal surface 260 thereof. The pockets 258 are illustrated as having a curved shape, but it is contemplated that the pockets 258 may assume any suitable shape. The cut ring 278 further includes a plurality of frangible portions or legs 254 extending distally from a top or distal surface 262 of the annular body 257 of the cut ring 278. As shown in FIG. 20, the frangible legs 254 suspend the annular body 257 of the cut ring 278 in the recess 270 of the anvil head 240 to maintain the ring assembly 250 in the proximal position. The frangible legs 254 may have a curved shape and are positioned directly over a respective pocket 258. The frangible legs 254 are configured to deform (e.g., collapse) into the respective pocket 258 upon application of a distally-oriented threshold force on the ring assembly 250.

To facilitate deformation of the frangible legs 254, the distal surface 262 of the annular body 257 of the cut ring 278 defines a pair of annular indentations 264 disposed on opposite sides of the frangible legs 254. The indentations 264 may have an arcuate, V-shaped, or any suitable cross-sectional configuration. The frangible legs 254 of the cut ring 278 may be fabricated from the same or a different material as the annular body 257 of the cut ring 278. For example, the frangible legs 254 may be fabricated from polytetrafluoroethylene, polypropylene or polyester.

In operation, prior to firing of the annular knife 30 (FIGS. 3 and 6), the ring assembly 250 (including the backup member 276 and the cut ring 278) is in its retracted or proximal position. In the proximal position, the frangible legs 254 of the cut ring 278 are in engagement with an inner surface 272 of the anvil head 240, thereby maintaining the ring assembly 250 in the proximal position, as shown in FIG. 20. With the ring assembly 250 in the proximal position, the inwardly extending fingers 298 of the backup member 276 are engaged by the anvil center rod 238, such that the anvil head 240 is retained in the first, operative condition and prevented from pivoting relative to the anvil center rod 238.

When the annular knife 30 (FIGS. 3 and 6) is advanced, the annular knife 30 engages the annular body 257 of the cut ring 278 of the ring assembly 250. The annular knife 30 pierces the annular body 257 of the cut ring 278 and ultimately engages the annular lip 252 of the backup member 276. The force applied by the annular knife 30 on the ring assembly 250 is transferred to the frangible legs 254 of the cut ring 278, which are compressed between the annular body 257 of the cut ring 278 and the inner surface 272 of the anvil head 240. Upon the annular knife 30 applying a distally-oriented threshold force on the ring assembly 250, the frangible legs 254 of the cut ring 278 detach or break from the annular body 257 of the cut ring 278 along the annular indentations 264.

Figure 23:
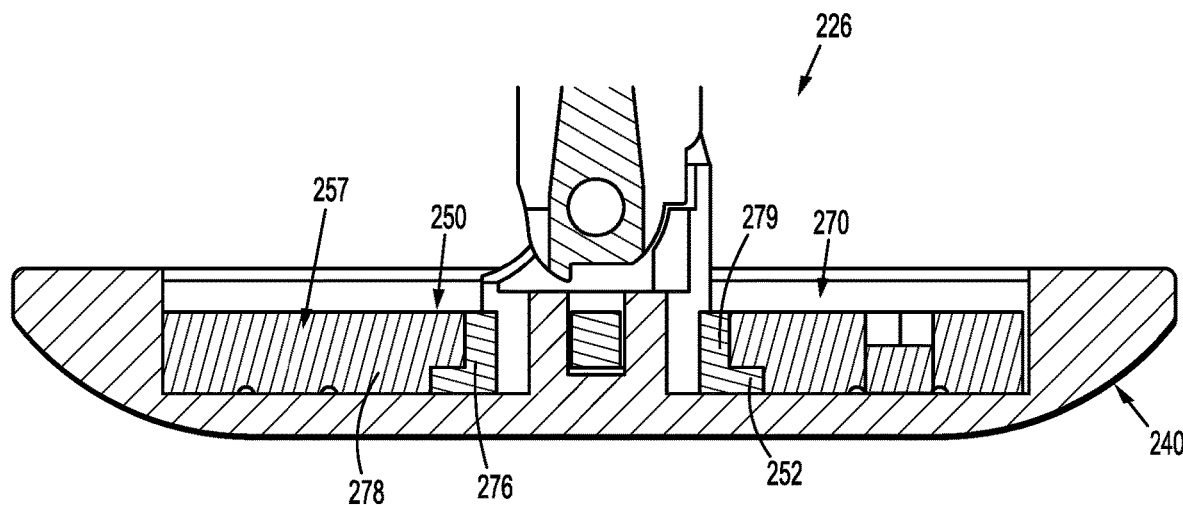
FIG. 23 is a side cross-sectional view of the anvil assembly of FIG. 20 illustrating the ring assembly in a distal position.
Figure 24:
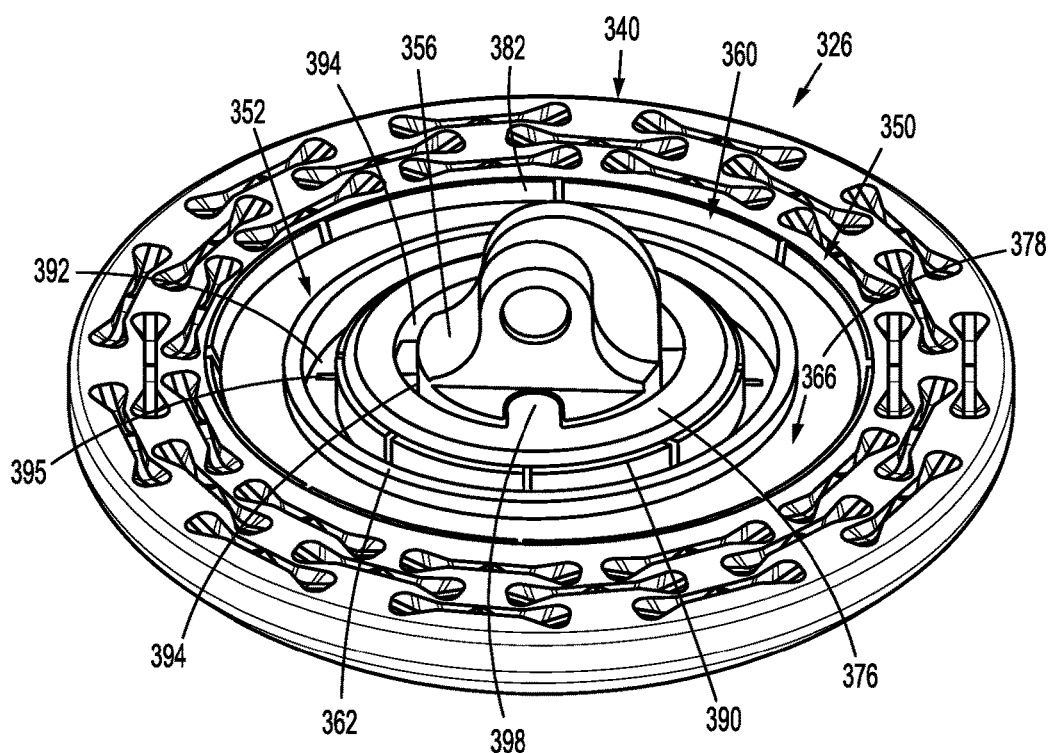
FIG. 24 is a perspective view of components of another embodiment of a surgical anvil assembly for incorporation into the circular stapling instrument of FIG. 1.
Figure 25:
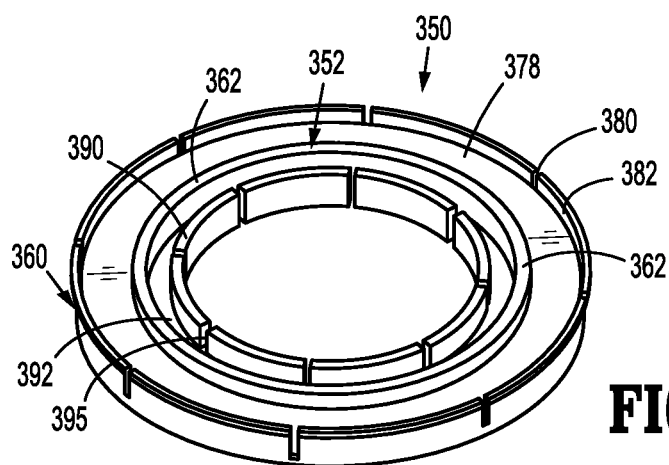
FIG. 25 is a perspective view of a proximal side of a ring assembly of the anvil assembly of FIG. 24.
Figure 26:
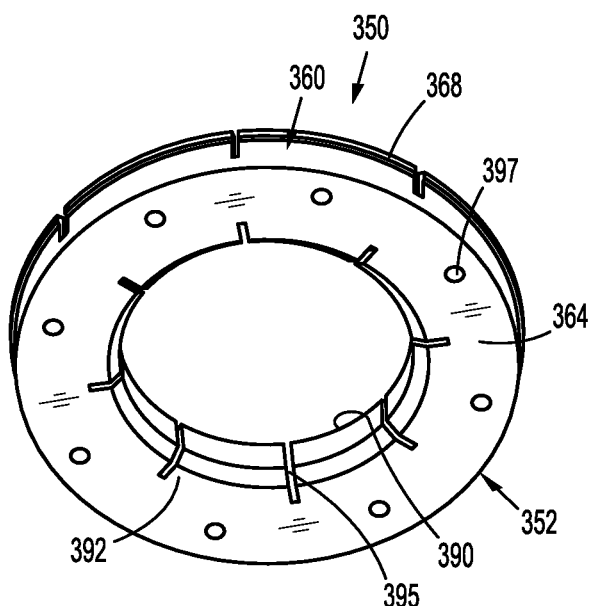
FIG. 26 is a perspective view of a distal side of the ring assembly of FIG. 25.
Figure 27:
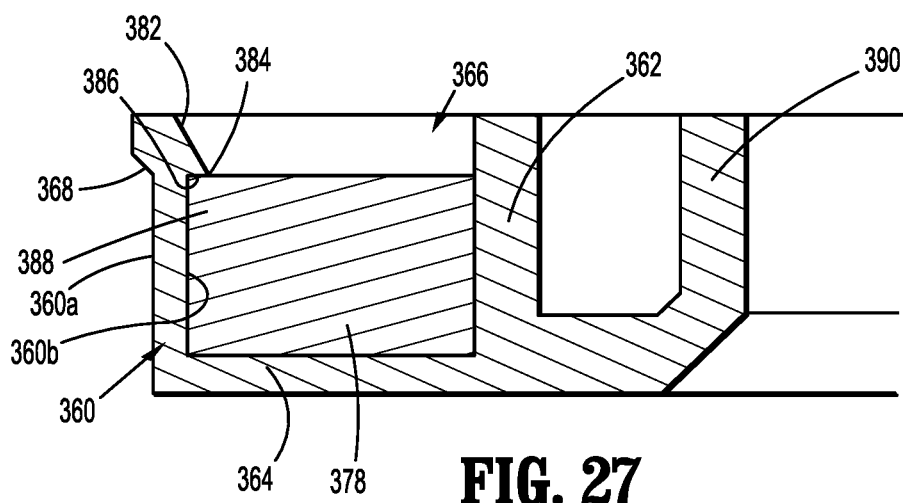
FIG. 27 is a partial, side cross-sectional view of the ring assembly of FIG. 25.

With the frangible legs 254 of the cut ring 278 detached from the annular body 257 of the cut ring 278, a continued distally-oriented force on the ring assembly 250, applied via the annular knife 30, drives the annular body 257 of the cut ring 278 and the backup member 276 distally, whereby the frangible legs 254 of the cut ring 278 collapse or fall into the respective pockets 258 in the annular body 257 of the cut ring 278, as shown in FIG. 23. As the ring assembly 250 is advanced toward the distal position, the inwardly extending fingers 298 of the backup member 276 disengage from the arms of the anvil center rod 238, allowing for the anvil head 240 to pivot relative to the anvil center rod 238. It is contemplated that the anvil head 240 may pivot automatically relative to the anvil center rod 238 in the same manner described above. In embodiments, the anvil head 240 may be pivoted automatically or manually via any suitable mechanism, such as those mechanisms described in the patents incorporated by reference herein.

With reference to FIGS. 24-29, another embodiment of a surgical anvil assembly 326 is illustrated, similar to the surgical anvil assemblies described above. Due to the similarities between the anvil assembly 326 of the present embodiment and the anvil assemblies described above, only those elements of the anvil assembly 326 deemed necessary to elucidate the differences from the previously described anvil assemblies will be described in detail.

The anvil assembly 326 generally includes an anvil center rod (not shown), similar to the anvil center rods described above, an anvil head 340 configured to be pivotally mounted to the anvil center rod, and a ring assembly 350 configured to selectively unlock the anvil head 340 from the anvil center rod. The anvil head 340 is configured to pivot relative to the anvil center rod between a first operative condition and a second pivoted or tilted condition.

The anvil head 340 defines a recess 370 (FIG. 28) therein having a post 356 of the anvil head 340 extending proximally therefrom. The post 356 of the anvil head 340 is configured to be pivotally coupled to a distal end of the anvil center rod. The recess 370 of the anvil head 340 is dimensioned for slidable receipt of the ring assembly 350. The anvil head 340 includes an annular, inner peripheral surface 372 that partially defines the recess 370, and an inner race or catch 374 that extends radially inward from the inner peripheral surface 372. The inner race 374 resists, without preventing, distal movement of the ring assembly 350 through the recess 370 of the anvil head 340.

Figure 28:
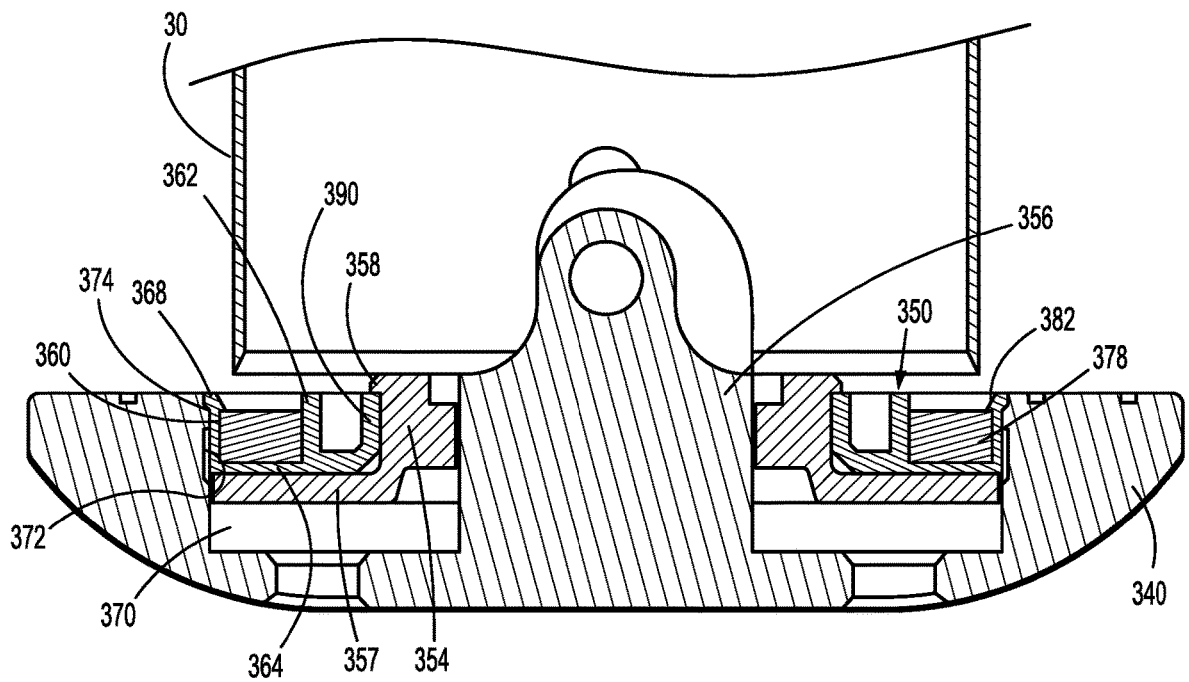
FIG. 28 is a side cross-sectional view of the anvil assembly of FIG. 24 illustrating the ring assembly in a proximal position.
Figure 29:
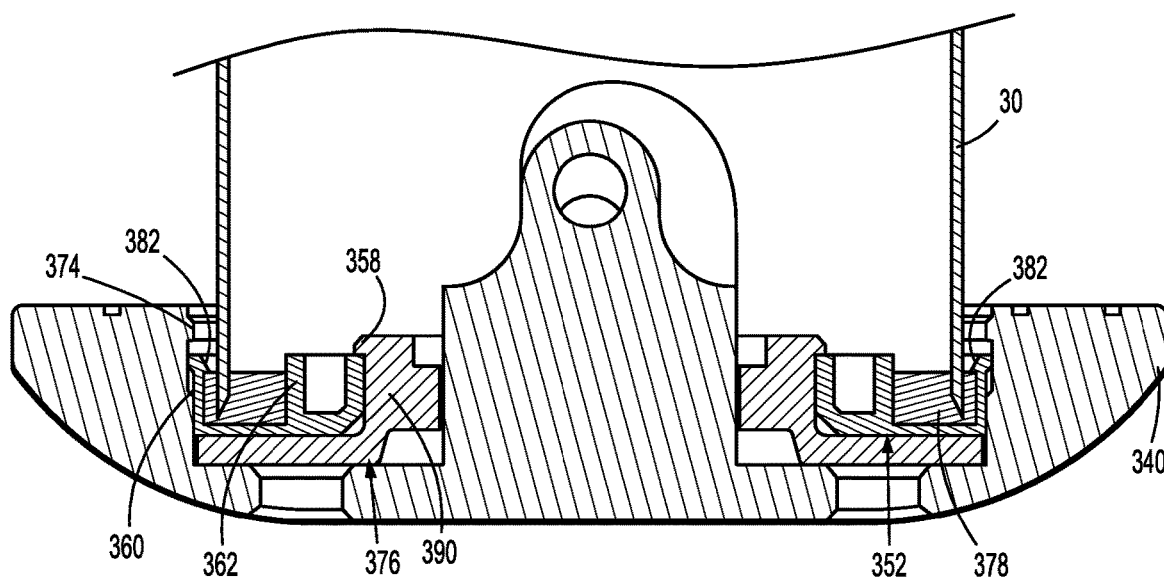
FIG. 29 is a side cross-sectional view of the anvil assembly of FIG. 24 illustrating the ring assembly in a distal position.

The ring assembly 350 generally includes a backup member 376, similar to the backup members described above, a ring cup 352 nested in the backup member 376, and a cut ring 378 nested in the ring cup 352. The ring assembly 350 is moved within the recess 370 of the anvil head 340 upon application of a force thereto, e.g., during advancement of an annular knife 30 (FIGS. 28 and 29). The backup member 376 defines a central opening 394 for reception of the post 356 of the anvil head 340. The central opening 394 is dimensioned to facilitate movement of the backup member 376 about the post 356 from a pre-fired, retracted or first position to a post-fired, advanced or second position within the recess 370 of the anvil head 340. The backup member 376 is retained in the proximal position by the inner race 374 of the anvil head 340, which supports the ring cup 352 in the proximal position (FIG. 28), as will be described.

The backup member 376 includes a pair of diametrically opposed fingers 398 extending inwardly into the central opening 394. The fingers 398 are engaged by the anvil center rod to prevent the backup member 376 from moving in a proximal direction and to maintain the anvil head 340 in the operative condition (e.g., untilted). Pivotal movement of the anvil head 340 relative to the anvil center rod is permitted only after the fingers 398 are distally spaced from the anvil center rod.

The backup member 376 of the ring assembly 350 further includes an annular wall or ring 354, and a disc-shaped platform 357 extending radially outward from a distal portion of the annular wall 354. The annular wall 354 has a lip 358 extending radially inward from a proximal portion thereof. The lip 358 is configured to engage (e.g., via snap-fit engagement) the ring cup 352 to retain the ring cup 352 with the backup member 376. The backup member 376 may be formed from a hard material such as metal, although other materials of construction are envisioned.

The ring cup 352 of the ring assembly 350 supports the cut ring 378 therein and guides the annular knife 30 into the cut ring 378 to prevent partial or offset cutting of the cut ring 378. The ring cup 352 is nested with the backup member 376 by being captured between an inner peripheral surface 372 of the anvil head 340 and the backup member 376. The ring cup 352 generally includes an annular outer wall 360, an annular, first inner wall 362, and a disc-shaped base 364 interconnecting the outer wall 360 and the first inner wall 362. The outer wall 360, the base 364, and the first inner wall 362 cooperatively define a cavity or annular chamber 366 dimensioned for receipt of the cut ring 352.

As best shown in FIGS. 24-27, the outer wall 360 of the ring cup 352 has an annular, outer peripheral surface 360a and an annular, inner peripheral surface 360b, wherein a thickness of the annular wall 360 is defined therebetween. An outer lip 368 extends radially outward from the outer peripheral surface 360a of the outer wall 360. The outer lip 368 of the outer wall 360 overlaps the inner race 374 of the anvil head 340 to support the ring assembly 350 in the proximal position and resist movement of the ring assembly 350 toward the distal position.

The outer wall 360 may have a plurality of slits 380 defined therein. The slits are arranged circumferentially about the outer wall 360. The slits 380 render the outer wall 360 flexible, such that upon distal advancement of the ring assembly 350 through the recess 370 of the anvil head 340, the outer wall 360 may flex or bend radially inward to snap into place under the inner race 374 of the anvil head 340. In embodiments, instead of or in addition to having the slits 380, the outer wall 360 may be fabricated from a flexible material to facilitate radial contraction of the outer wall 360 during assembly into the anvil head 340.

The outer wall 360 of the ring cup 352 further includes a chamfered surface 382 that slopes downwardly (e.g., distally) from a proximal-most surface of the outer wall 360. An annular inner edge 384 of the chamfered surface 382 (FIG. 27) is disposed radially inward of the inner peripheral surface 360b of the outer wall 360, such that the chamfered surface 382 defines an undercut or overhang 386. The undercut 386 overlays an outer edge 388 of the cut ring 378 to capture the cut ring 378 in the annular chamber 366 of the ring cup 352. As such, as the annular knife 30 advances, the chamfered surface 382 guides or redirects the knife 30 inwardly and into contact with the cut ring 378 at a location radially inward of the outer edge 388 of the cut ring 378. This eliminates the possibility of a line-to-line stapling condition.

It is contemplated that the location at which the knife 30 contacts the cut ring 378 may be adjusted by adjusting the depth of the undercut 386. For example, to ensure that the knife 30 contacts the cut ring 378 at a more radially inward location, the depth of the undercut 386 in the outer wall 360 may be increased. In addition or in the alternative to increasing the depth of the undercut 386, the annular inner edge 384 of the chamfered surface 382 may extend a greater distance radially inward relative to the inner peripheral surface 360b of the outer wall 360 to cause the knife 30 to contact the cut ring 378 at a more radially inward location.

The ring cup 352 further includes an annular, second inner wall 390 disposed radially inward of the first inner wall 362. The second inner wall 390 may be coupled to the first inner wall 362 via a plurality of bridge members 392 that permit the second inner wall 390 to flex relative to the first inner wall 362. The second inner wall 390 may also include a plurality of slits 395 defined therein. The slits 395 are arranged circumferentially about the second inner wall 390 to further facilitate flexing of the second inner wall 390. To assemble the ring cup 352 to the backup member 376, the second inner wall 390 of the ring cup 352 is flexed radially inward and captured under the lip 358 of the backup member 376.

The cut ring 378 of the ring assembly 350 is received in the annular chamber 366 of the ring cup 352 between the outer wall 360 of the ring cup 352 and the first inner wall 362 of the ring cup 352. The outer edge 388 of the cut ring 378 is disposed under the undercut 386 of the chamfered surface 382 of the ring cup 352. It is contemplated that the cut ring 378 may be press fit onto the ring cup 352. Thus, movement of the ring cup 352 between proximal and distal positions causes corresponding movement of the cut ring 378. In embodiments, the cut ring 378 may be formed through a molding process, e.g., an injection molding process, and extend through a plurality of holes 397 (FIG. 26) defined through the base portion 364 of the ring cup 352.

The cut ring 378 may be fabricated from a material having a durometer which permits the annular knife 30 to pierce through the cut ring 378 and bottom out against the base portion 364 of the ring cup 352. As such, all of the ring cup 352 or select portions thereof (e.g., the chamfered surface 382 and the base portion 364) is fabricated from a harder material than the cut ring 378. Suitable materials for the cut ring 378 include polytetrafluoroethylene, polypropylene or polyester. Other materials are contemplated.

In operation, prior to firing a circular stapling instrument having the surgical anvil assembly 326 of the presently described embodiment, the ring assembly 350 including the backup member 376, the ring cup 352, and the cut ring 378, is in its retracted or proximal position, as shown in FIG. 28. The outer lip 368 of the outer wall 360 of the ring cup 352 overlaps the inner race 374 of the anvil head 340 to support the ring assembly 350 in the proximal position. With the ring assembly 350 in the proximal position, the inwardly extending fingers 398 of the backup member 376 are engaged by the anvil center rod to maintain the anvil head 340 in the first, operative condition, as described above.

Upon actuation of the stapling instrument, the annular knife 30 is advanced into engagement with the cut ring 378 of the ring assembly 350. In some instances, a section of the annular knife 30 may be out of vertical registration with the cut ring 378 (e.g., disposed radially outward). In these instances, as the knife 30 is advanced, the knife 30 engages the chamfered surface 382 of the ring cup 352, which directs the knife 30 radially inward into vertical registration with the cut ring 378. Due to the chamfered surface 382 of the ring cup 352 hanging over the cut ring 378, the knife 30 makes contact with the cut ring 378 radially inward of the outer edge 388 of the cut ring 378.

As advancement of the knife 30 is continued, the knife 30 pierces the cut ring 378 and ultimately engages the base portion 364 of the ring cup 352, as shown in FIG. 29. The force applied by the knife 30 flexes or bends the outer wall 360 of the ring cup 352 inwardly to pass over the inner race 374 of the anvil head 340. The ring cup 352, along with the cut ring 378 and the backup member 376, is then driven distally toward the distal position.

As the ring assembly 350 is advanced toward the distal position, the inwardly extending fingers 398 of the backup member 378 disengage the anvil center rod, allowing for the anvil head 340 to pivot relative to the anvil center rod. It is contemplated that the anvil head 340 may be configured to pivot automatically relative to the anvil center rod in any manner described herein. In embodiments, the anvil head 340 may be pivoted via any suitable pivoting mechanism, whether it is automatic or manual.

Figure 30:
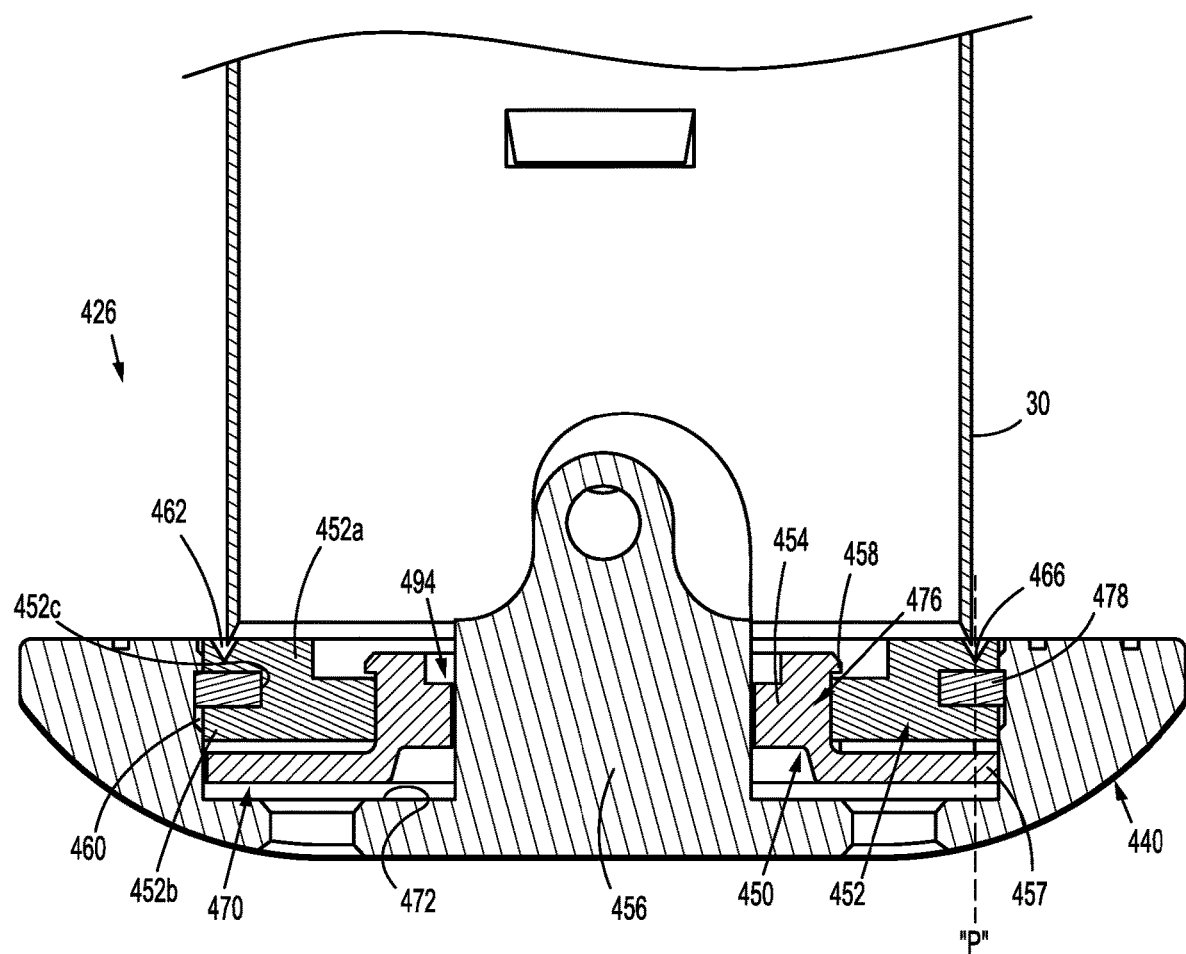
FIG. 30 is a side cross-sectional view of another embodiment of a surgical anvil assembly for incorporation into the circular stapling instrument of FIG. 1.
Figure 31:
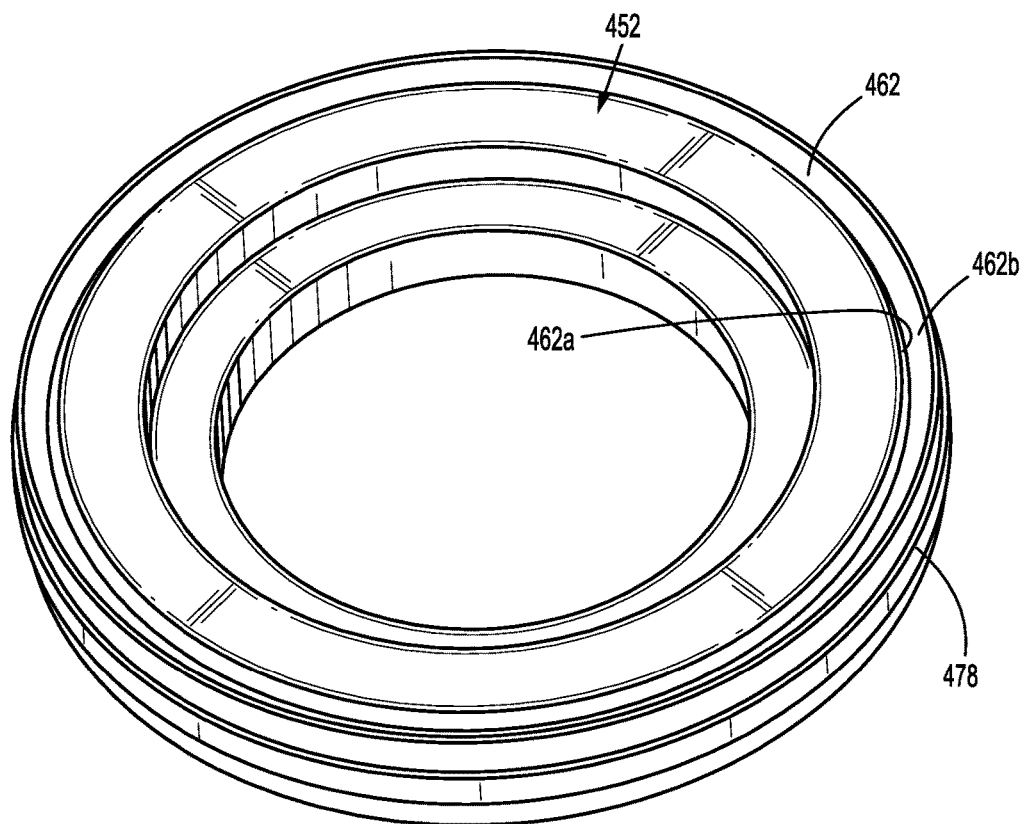
FIG. 31 is a perspective view of a ring assembly of the anvil assembly of FIG. 30.
Figure 32:
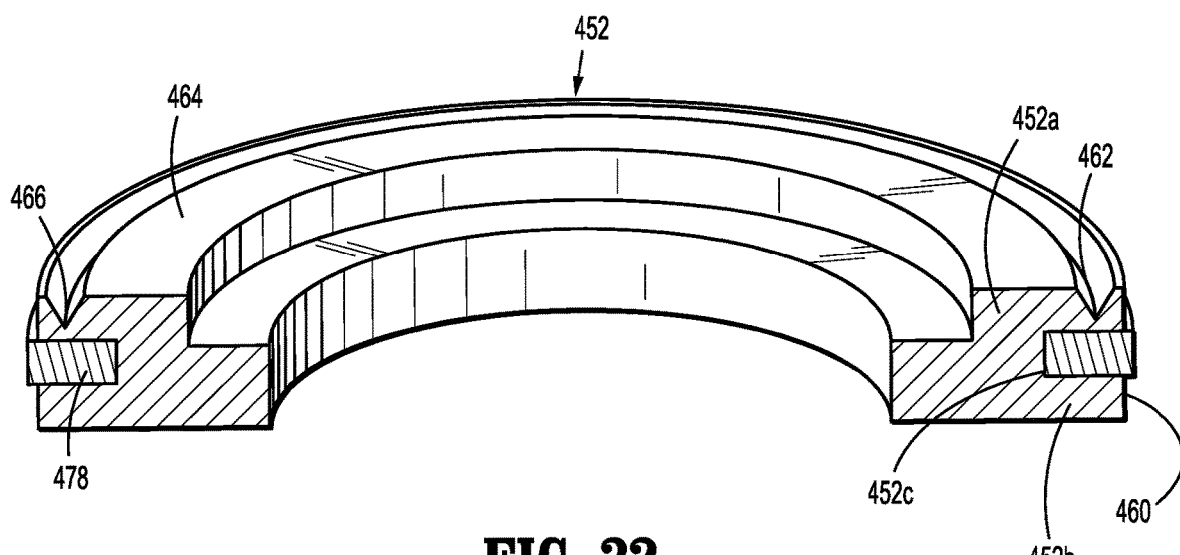
FIG. 32 is a perspective, cross-sectional view of the ring assembly of FIG. 31.

With reference to FIGS. 30-32, another embodiment of a surgical anvil assembly 426 is illustrated, similar to the anvil assemblies described above. Due to the similarities between the anvil assembly 426 of the present embodiment and the anvil assemblies described above, only those elements of the anvil assembly 426 deemed necessary to elucidate the differences from anvil assemblies described above will be described in detail.

The anvil assembly 426 generally includes an anvil center rod (not shown), similar to the anvil center rods described above, an anvil head 440 pivotally mounted to the anvil center rod, and a ring assembly 450 configured to selectively unlock the anvil head 440 from the anvil center rod. The anvil head 440 is configured to pivot relative to the anvil center rod between a first operative condition and a second pivoted or tilted condition. The anvil head 440 defines a recess 470 therein for receipt of the ring assembly 450. The anvil head 440 includes an annular, inner peripheral surface 472 that partially defines the recess 470.

The anvil head 440 may include a frangible retainer member (not shown), similar to the retainer member 127 described in U.S. Pat. No. 9,532,781, the entire contents of which having been incorporated by reference above. The frangible retainer member may be disposed in the recess 470 of the anvil head 440 between the inner peripheral surface 472 of the anvil head 440 and the ring assembly 450 so that upon application of a threshold distal force on the ring assembly 450, the frangible retainer collapses, allowing distal advancement of the ring assembly 450 and the annular knife 30.

The ring assembly 440 is received within the recess 470 defined in the anvil head 440 and generally includes a backup member 476, a first cut ring 452 nested in the backup member 476, and a second cut ring 478 nested in the first cut ring 452. The ring assembly 450 is moved within the recess 470 of the anvil head 440 upon application of a force thereto, e.g., during advancement of the annular knife 30.

The backup member 476 defines a central opening 494 for reception of a post 456 of the anvil head 440. The central opening 494 is dimensioned to facilitate movement of the backup member 476 about the post 456 from a pre-fired, retracted or first position to a post-fired, advanced or second position within the recess 470 of the anvil head 440. The backup member 476, similar to the backup members described above, includes a pair of diametrically opposed fingers (not explicitly shown) extending inwardly into the central opening 494. The fingers are engaged by the anvil center rod to prevent the backup member 476 from moving in a proximal direction and to maintain the anvil head 440 in the operative condition (e.g., untilted). Pivotal movement of the anvil head 440 relative to the anvil center rod is permitted only after the fingers of the backup member 476 are distally spaced from the anvil center rod, as already described above.

The backup member 476 further includes an annular wall or ring 454 and a disc-shaped platform 457 extending radially outward from a distal portion of the annular wall 454. The annular wall 454 has a lip 458 extending radially inward from a proximal portion thereof. The lip 458 is configured to engage (e.g., via snap-fit engagement) the first cut ring 452 to retain the first cut ring 452 with the backup member 476. The backup member 476 may be formed from a hard material such as metal, although other materials of construction are envisioned.

The first cut ring 452 of the ring assembly 450 supports the second cut ring 476 therein and provides a surface on which staples are to be cut. The first cut ring 452 is fabricated from a first material, such as, for example, a hard plastic, that resists being pierced by the annular knife 30. The first cut ring 452 is nested with the backup member 476 by being captured between the inner peripheral surface 472 of the anvil head 440 and the backup member 476. The first cut ring 452 includes a proximal portion 452a, a distal portion 452b, and an annular cutout or recess 452c disposed therebetween. The annular recess 452c is defined in an outer peripheral surface 460 of the first cut ring 452 and captures the second cut ring 478 therein.

The first cut ring 452 further defines an annular groove 462 in the proximal portion 452a thereof that extends circumferentially along a proximal surface 464 of the first cut ring 452. While the groove 462 is illustrated as having a V-shaped configuration, it is contemplated that the groove 462 may assume any suitable configuration, such as, for example, U-shaped or squared. The groove 462 is in vertical registration with the annular recess 452c of the first cut ring 452 and is configured to guide the annular knife 30 (FIG. 32) radially inward toward an apex 466 of the groove 462.

The proximal portion 452a of the first cut ring 452 has a reduced thickness defined between the apex 466 of the groove 462 and the annular recess 452c. As such, when the annular knife 30 is advanced distally into the proximal portion 452a of the first cut ring 452, the annular knife 30 cuts through the proximal portion 452a of the first cut ring 452 along a vertical pathway "P" running through the groove 462 of the first cut ring 452. The depth of the groove 462 may be increased to increase the force necessary for the annular knife 30 to cut therethrough, or decreased to decrease the force necessary for the annular knife 30 to cut therethrough.

The second cut ring 478 of the ring assembly 450 is received in the annular recess 452c of the first cut ring 452. As mentioned above, the second cut ring 478 is in vertical registration with the groove 462 of the first cut ring 452, such that the groove 462 of the first cut ring 452 guides the annular knife 30 into the second cut ring 478 at a location radially inward of an outer peripheral surface of the second cut ring 478. It is contemplated that the second cut ring 478 may be press fit into the annular recess 452c of the first cut ring 452. Thus, movement of the first cut ring 452 between proximal and distal positions causes corresponding movement of the second cut ring 478. The relatively harder first cut ring 452 provides a surface on which the annular knife 30 can cut through staples without being dragged into the relatively softer second cut ring 478, which is used to cut tissue cleanly.

In embodiments, the second cut ring 478 may be formed through a molding process, e.g., an injection molding process. The second cut ring 478 may be fabricated from a material having a durometer which permits the annular knife 30 to pierce through the second cut ring 478 and bottom out against the distal portion 452b of the first cut ring 452b. As such, the second cut ring 478 is fabricated from a softer material than the first cut ring 452. Suitable materials for the second cut ring 478 include polytetrafluoroethylene, polypropylene or polyester. Other materials are contemplated.

In operation, prior to firing a circular stapling instrument having the surgical anvil assembly 426 of the presently described embodiment, the ring assembly 450, including the backup member 476, the first cut ring 452, and the second cut ring 478, is in its retracted or proximal position. The frangible retainer member (not explicitly shown) is interposed between the backup member 476 and the inner surface 472 of the anvil head 440 to support the ring assembly 450 in the proximal position. With the ring assembly 450 in the proximal position, the inwardly extending fingers of the backup member 476 are engaged by the anvil center rod, such that the anvil head 440 is retained in the first, operative condition.

Upon actuation of the stapling instrument, the annular knife 30 is advanced into engagement with ramped surfaces 462a, 462b (FIG. 31) that define the groove 462 of the first cut ring 452. The ramped surfaces 462a, 462b direct the knife 30 radially inward into vertical registration with a central portion of the second cut ring 478. The annular knife 30 moves through the groove 462 and contacts the apex 466 of the groove 462, transferring the distally-oriented force to the frangible retainer member. Upon applying a threshold force on the frangible retainer member, the frangible retainer member collapses, allowing for distal movement of the ring assembly 450 through the recess 470 of the anvil head 440.

As the ring assembly 450 is advanced toward the distal position, the inwardly extending fingers of the backup member 476 disengage from the anvil center rod, allowing for the anvil head 440 to pivot relative to the anvil center rod. It is contemplated that the anvil head 440 may be configured to pivot automatically relative to the anvil center rod in any manner described herein. In embodiments, the anvil head 440 may be pivoted via any suitable pivoting mechanism, whether it is automatic or manual.

As advancement of the annular knife 30 is continued, the annular knife 30 cuts through the proximal portion 452a of the first cut ring 452, slicing through any tissue and staples along its pathway and dissevering an outer circumferential section of the proximal portion 452a of the first cut ring 452 from the remainder of the proximal portion 452a of the first cut ring 452. It is contemplated that the outer circumferential section of the first cut ring 452 remains adhered, via friction, to an outer surface of the annular knife 30. As advancement of the annular knife 30 is continued, the annular knife 30 cuts through the second cut ring 478 and ultimately bottoms out on the distal portion 452b of the first cut ring 452. In embodiments, the frangible retainer member may be configured to collapse after the annular knife 30 cuts through the proximal portion 452a of the first cut ring 452 rather than before.

With reference to FIGS. 33-40, another embodiment of a surgical anvil assembly 526 is illustrated, similar to the anvil assemblies described above. Due to the similarities between the anvil assembly 526 of the present embodiment and the anvil assemblies described above, only those elements of the anvil assembly 526 deemed necessary to elucidate the differences from the above anvil assemblies will be described in detail.

Figure 33:
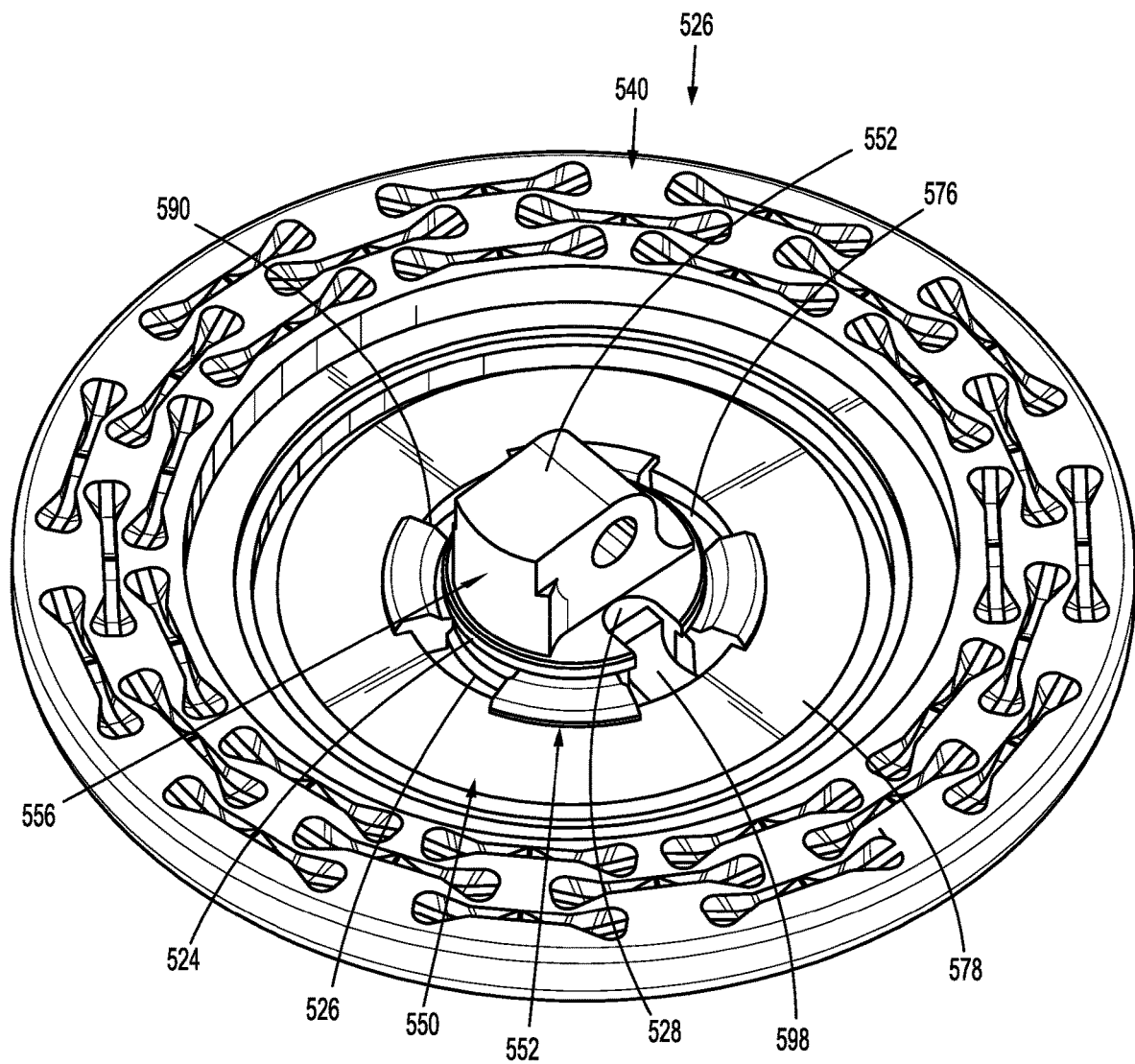
FIG. 33 is a perspective view of components of another embodiment of a surgical anvil assembly for incorporation into the circular stapling instrument of FIG. 1.
Figure 34:
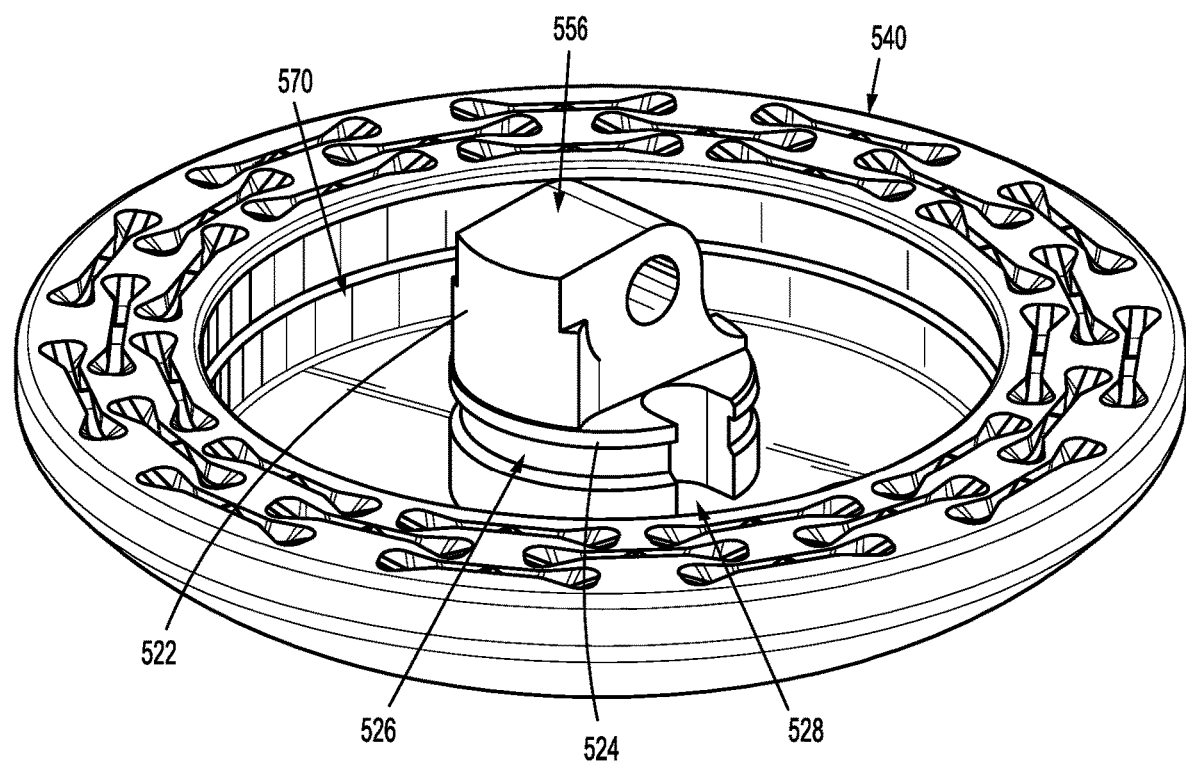
FIG. 34 is a perspective view of an anvil head of the anvil assembly of FIG. 33.

With reference to FIGS. 33 and 34, the anvil assembly 526 generally includes an anvil center rod (not shown), similar to the anvil center rods described above, an anvil head 540 pivotally mounted to the anvil center rod, and a ring assembly 550 configured to selectively unlock the anvil head 540 from the anvil center rod. The anvil head 540 is configured to pivot relative to the anvil center rod between a first operative condition and a second pivoted or tilted condition.

The anvil head 540 defines a recess 570 therein dimensioned for receipt of the ring assembly 550. The anvil head 540 includes a post 556 centrally located within the recess 570 and projects proximally from a floor of the recess 570. The post 556 pivotally couples the anvil head 540 to the anvil center rod. For example, the post 556 of the anvil head 540 may be pivotally coupled to a pair of distal spaced arms of the anvil center rod. The post 556 has a body 522 having an annular ledge 524 projecting radially outward therefrom. The annular ledge 524 is configured to selectively maintain the ring assembly 550 in a pre-fired, proximal position. The body 522 of the post 556 defines an annular depression 526 disposed underneath or distally of the annular ledge 524.

The ring assembly 550 is received within the recess 570 defined in the anvil head 540 and generally includes a snap collar 552 engaged to the body 522 of the post 556, a backup member 576 supported on the snap collar 552, and a cut ring 578 captured between the snap collar 552 and the backup member 576. The ring assembly 550 is moved within the recess 570 upon application of a force thereto, e.g., during advancement of an annular knife, such as, for example, annular knife 30 (FIGS. 3 and 6).

Figure 35:
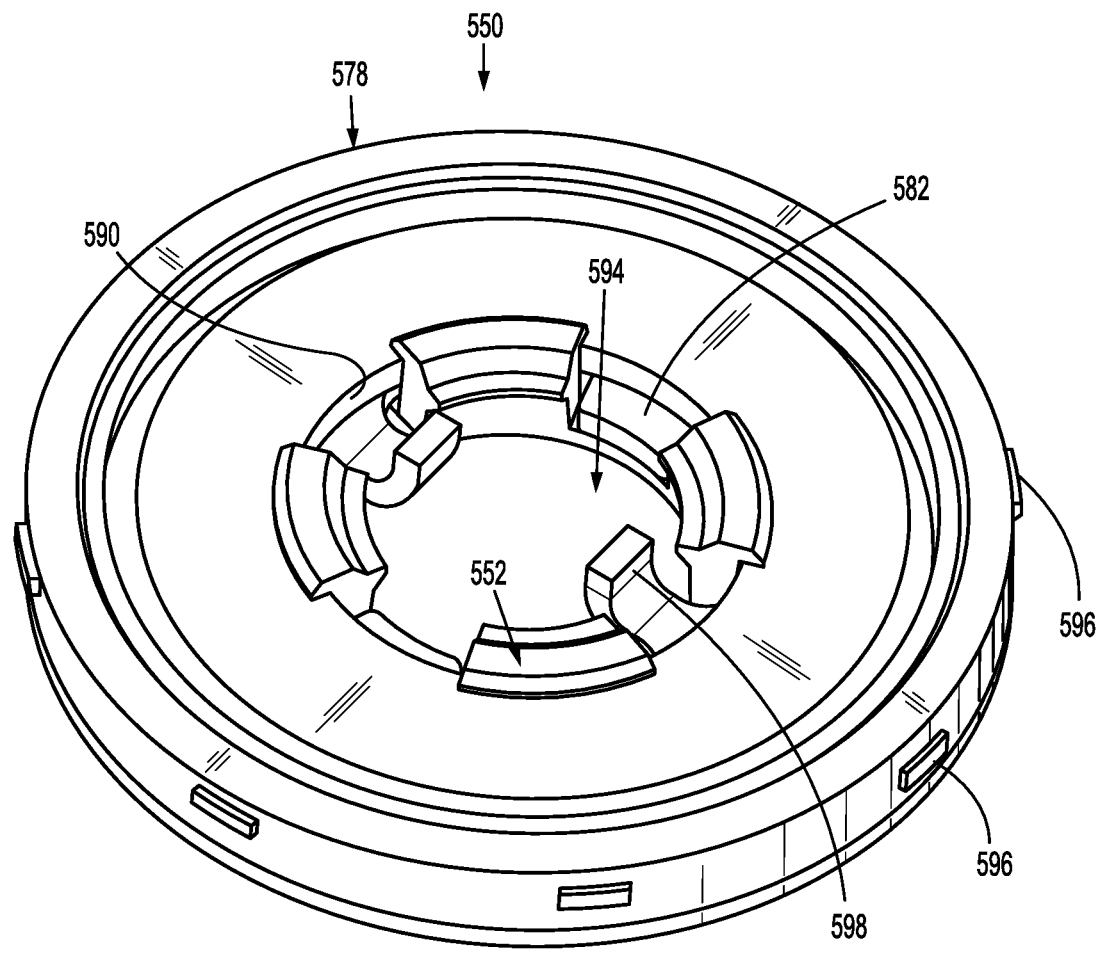
FIG. 35 is a perspective view of a ring assembly of the anvil assembly of FIG. 33.
Figure 36:
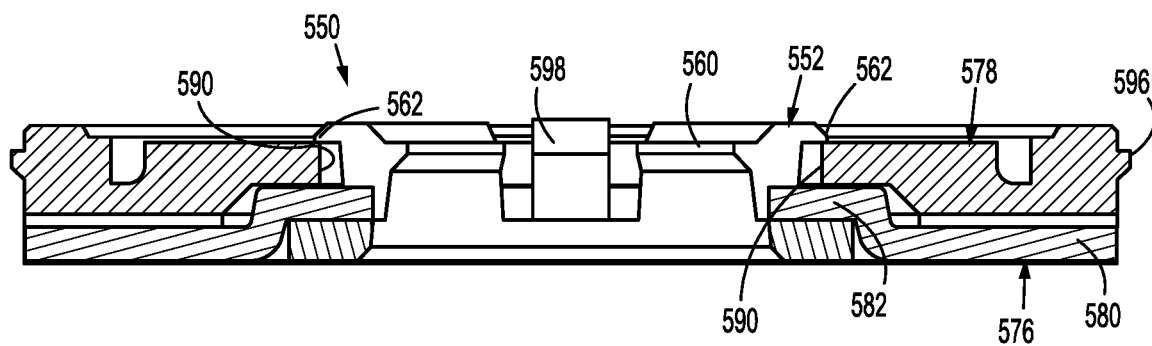
FIG. 36 is a side cross-sectional view of the ring assembly of FIG. 35.
Figure 37:
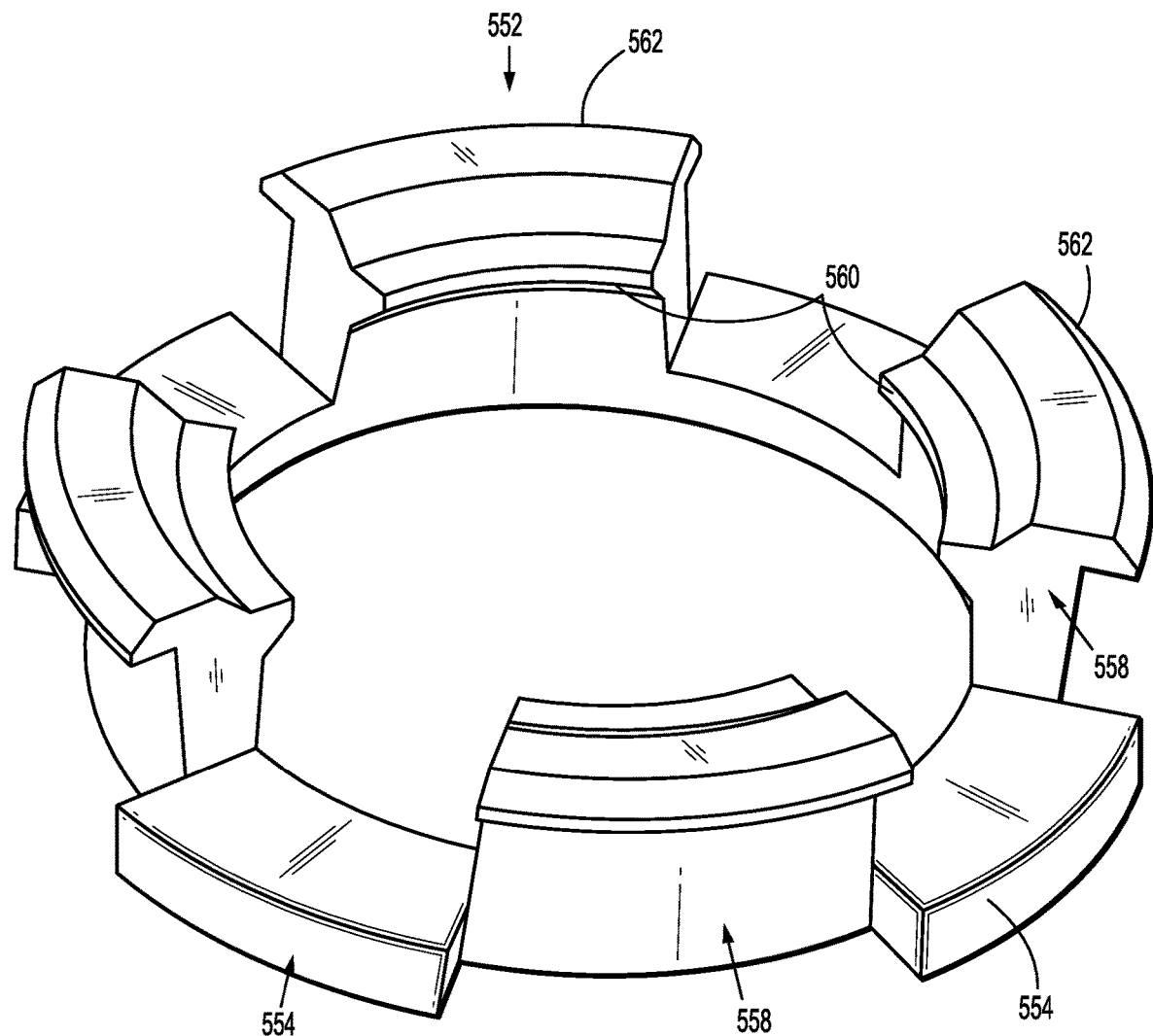
FIG. 37 is a perspective view of a snap collar of the ring assembly of FIG. 35.
Figure 38A:
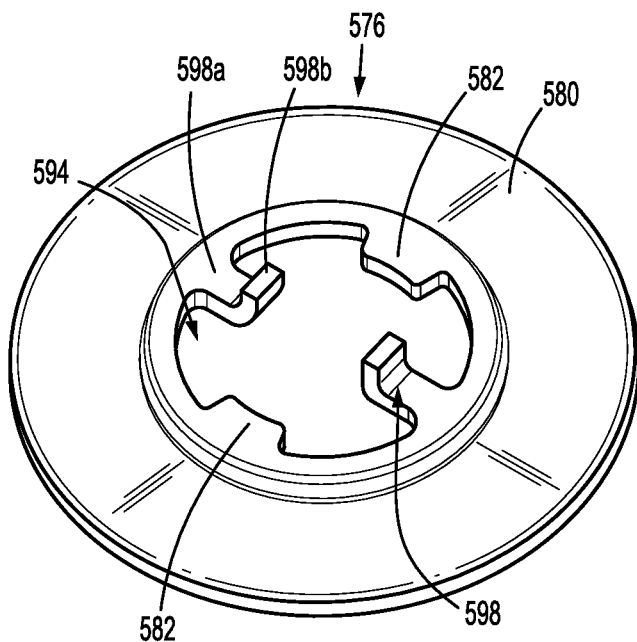
FIG. 38A is perspective view of a proximal side of a backup member of the ring assembly of FIG. 35.
Figure 38B:
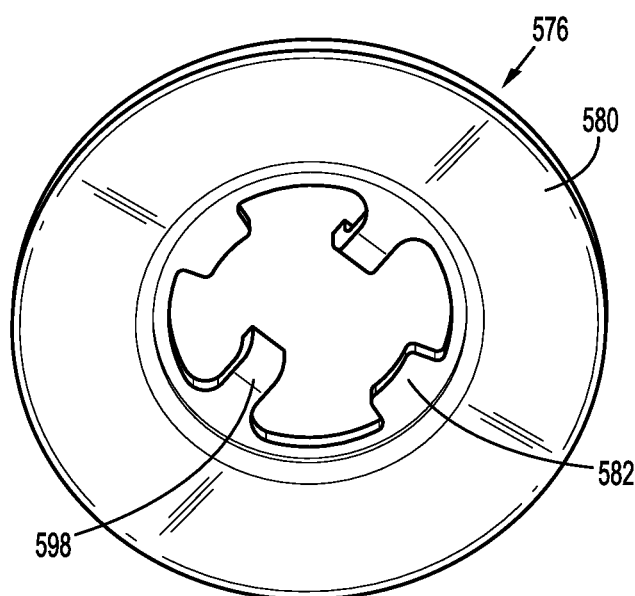
FIG. 38B is a perspective view of a distal side of the backup member of FIG. 38A.

With specific reference to FIGS. 35-37, the snap collar 552 of the ring assembly 550 is configured to selectively maintain the ring assembly 550 in the proximal position, but allow for movement of the ring assembly 550 toward the distal position upon the application of a distally-oriented threshold force thereon. The snap collar 552 may be a monolithically formed piece of plastic or may be constructed from a plurality of connected components. The snap collar 552 includes a plurality of horizontally-extending support surfaces or flanges 554, and a plurality of vertical extensions 558 interposed between respective adjacent pairs of the flanges 554. As such, the flanges 554 and vertical extensions 558 are alternately arranged around the circumference of the snap collar 552. The snap collar 552 may include four flanges 554 arranged circumferentially about the snap collar 552 in 90° spaced relation to one another. Similarly, the snap collar 552 may include four vertical extensions 558 arranged circumferentially about the snap collar 552 in 90° spaced relation to one another. It is contemplated that the snap collar 552 may have more or less than four flanges 554 and vertical extensions 558.

The flanges 554 of the snap collar 552 may be planar and support the backup member 576 thereon (FIG. 36), such that distal movement of the backup member 576 causes distal movement of the snap collar 552. The vertical extensions 558 of the snap collar 552 may extend proximally, at a perpendicular angle, relative to the flanges 554. The vertical extensions 558 each include an annular inner lip 560 extending radially inward therefrom, and an annular outer lip 562 extending radially outward therefrom. The annular inner lips 560 are supported on the annular ledge 524 of the post 556 of the anvil head 540 when the ring assembly 550 is in the proximal position. The annular inner lips 560 of the snap collar 552 resist movement of the ring assembly 550 toward the distal position until the distally-oriented threshold force causes outward flexure of the vertical extensions 558, which disengages the annular inner lips 560 of the snap collar 552 from the annular ledge 524 of the post 556 of the anvil head 540. The annular outer lips 562 of the snap collar 552 overlay a proximal surface of the cut ring 578 to prevent the cut ring 578 from moving relative to the snap collar 552.

With reference to FIGS. 35, 36, 38A, and 38B, the backup member 576 includes a ring body 580 defining a central opening 594, a pair of diametrically opposed tabs 582 extending radially inward from the annular body 594 into the central opening 594, and a pair of diametrically opposed fingers 598 extending inwardly into the central opening 594. The central opening 594 receives the post 556 of the anvil head 540 and is dimensioned to facilitate movement of the backup member 576 about the post 556 from a pre-fired, retracted or first position to a post-fired, advanced or second position within the recess 570 of the anvil head 540. The backup member 576 is retained in the proximal position via the snap collar's 552 engagement with the annular ledge 524 of the post 556.

The tabs 582 of the backup member 576 are supported on a first pair of diametrically opposed flanges 554 of the snap collar 552. The tabs 582 of the backup member 576 are configured to transfer a distally-oriented force, applied by an advancement of the annular knife 30, to the snap collar 552. The fingers 598 of the backup member 576 extend radially inward from the ring body 580 a further extent than do the tabs 582 of the backup member 576 and are received in cutouts 528 in the body 522 of the post 556. The fingers 598 of the backup member 576 have a first portion 598a extending horizontally from the ring body 580 of the backup member 576, and a second portion 598b extending vertically upward or proximal from the first portion 598a. The first portion 598a of each of the fingers 598 is supported on a second pair of diametrically opposed flanges 554 of the snap collar 552.

The second portion 598b of the fingers 598 are engaged by the anvil center rod to prevent the backup member 576 from moving in a proximal direction and to maintain the anvil head 540 in the operative condition (e.g., untilted). Pivotal movement of the anvil head 540 relative to the anvil center rod is permitted only after the fingers 598 of the backup member 576 are distally spaced from the anvil center rod. The backup member 576 may be stamped from a hard material such as metal, although other materials of construction are envisioned.

With reference to FIGS. 33, 35, 36, 39, and 40, the cut ring 578 of the ring assembly 550 is supported on the backup member 576 and has an inner peripheral surface 590 that is captured between the annular outer lip 562 of the snap collar 552 and the tabs 582 and fingers 598 of the backup member 576. Accordingly, proximal or distal movement of the backup member 576 results in a corresponding proximal or distal movement of the snap collar 552 and the cut ring 578. The cut ring 578 has a plurality of surface features 596 protruding from an outer peripheral surface thereof. The surface features 596 are press fit under an inner race 574 of the anvil head 540 to retain the ring assembly 550 in the recess 570.

The cut ring 578 may be fabricated from a material having a durometer which permits the annular knife 30 to pierce through the cut ring 578 and bottom out against the ring body 580 of the backup member 576. As such, the backup member 576 may be fabricated from a harder material than the cut ring 578. Suitable materials for the cut ring 578 include polytetrafluoroethylene, polypropylene or polyester. Other materials are contemplated.

Figure 39:
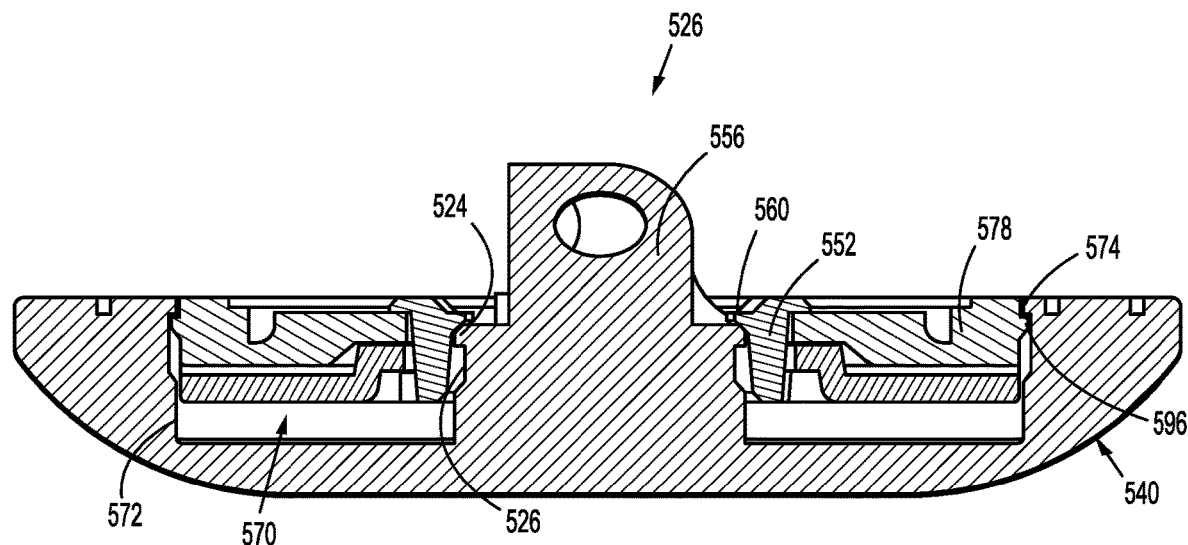
FIG. 39 is a side cross-sectional view of the anvil assembly of FIG. 33 illustrating the ring assembly in a proximal position.

In operation, prior to firing of a circular stapling instrument having the surgical anvil assembly 526 of the presently described embodiment, the ring assembly 550, including the backup member 576, the snap collar 552, and the cut ring 578, is in its retracted or proximal position in the recess 570 of the anvil head 540, as shown in FIG. 39. The annular inner lips 560 of the snap collar 552 are supported on the annular ledge 524 of the post 556 of the anvil head 540, and the surface features 596 of the cut ring 578 are supported on the inner race 574 of the anvil head 540. With the ring assembly 550 in the proximal position, the inwardly extending fingers 598 of the backup member 576 are engaged by the anvil center rod, such that the anvil head 540 is retained in the first, operative condition.

Upon actuation of the stapling instrument, the annular knife is advanced into engagement with the cut ring 578 of the ring assembly 550, which transfers the distally-oriented force to the backup member 576, which in turn transfers the distally-oriented force to the snap collar 552. Upon achieving a threshold force, the vertical extensions 558 of the snap collar 552 flex outwardly to separate the annular inner lips 560 of the snap collar 552 from the annular ledge 524 of the post 556 of the anvil head 540.

Figure 40:
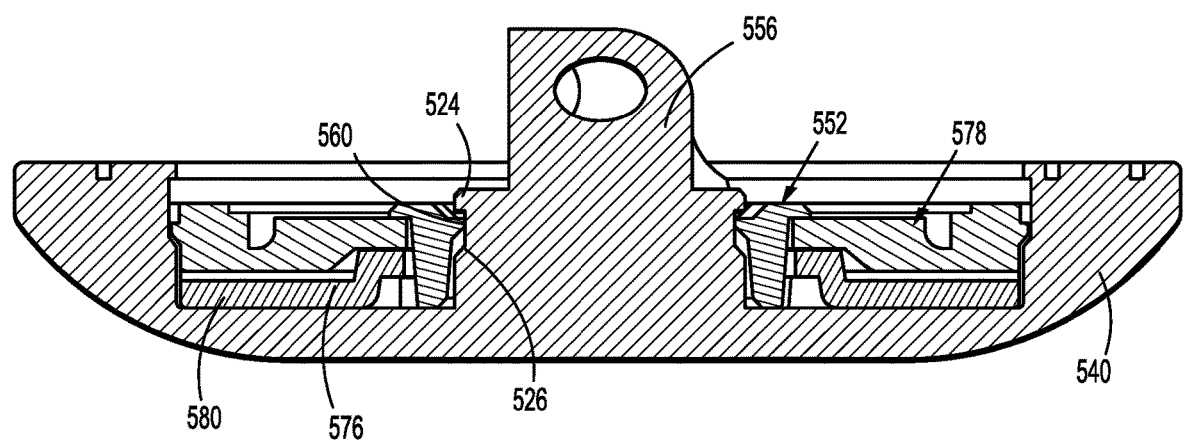
FIG. 40 is a side cross-sectional view of the anvil assembly of FIG. 33 illustrating the ring assembly in a distal position.
Figure 41:
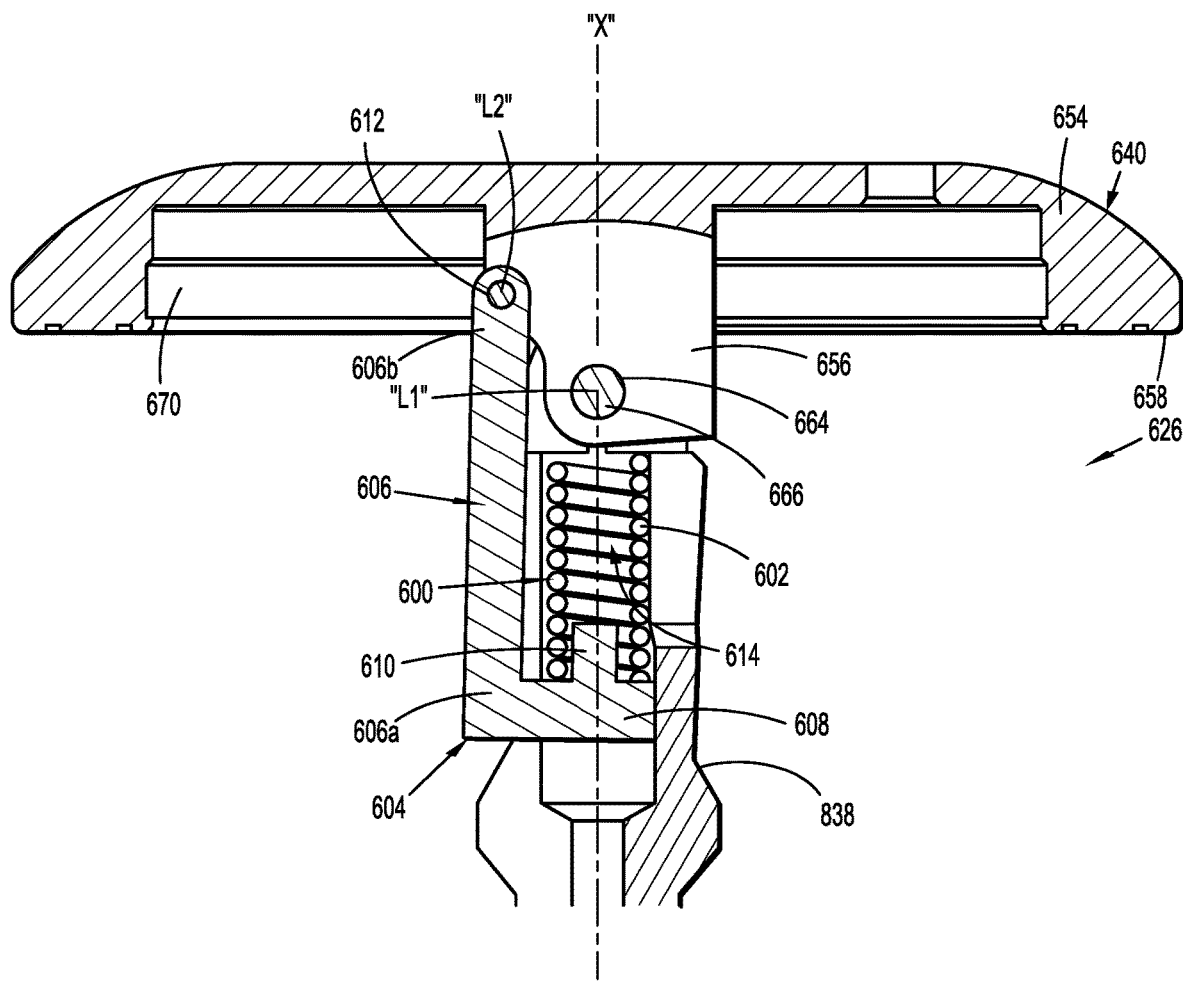
FIG. 41 is a side cross-sectional view of another embodiment of a surgical anvil assembly for incorporation into the circular stapling instrument of FIG. 1.
Figure 42:
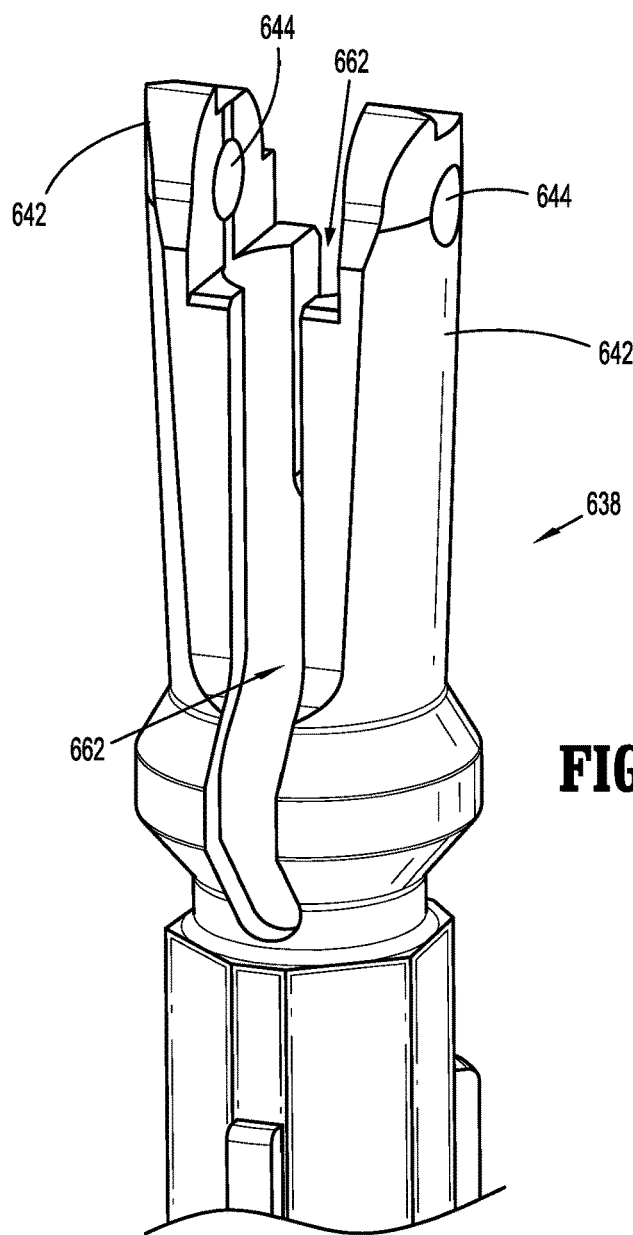
FIG. 42 is a perspective view of a distal portion of an anvil center rod of the anvil assembly of FIG. 41.
Figure 43:
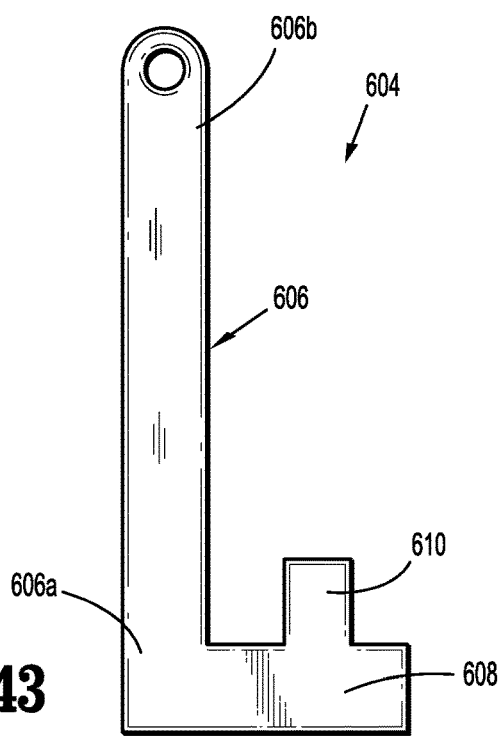
FIG. 43 is a side view of a linkage arm of a pivoting assembly of the anvil assembly of FIG. 41.
Figure 44:
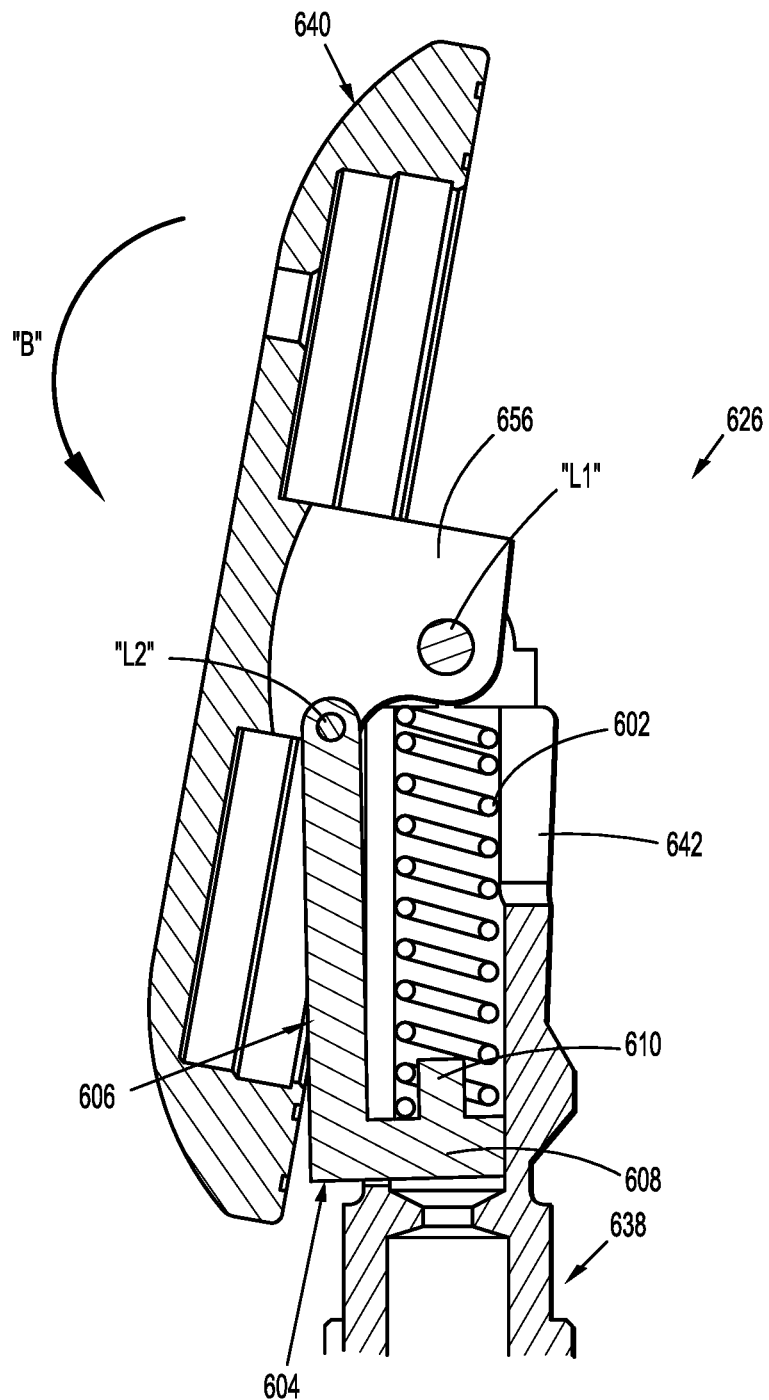
FIG. 44 a side cross-sectional view of the anvil assembly of FIG. 41 illustrating the anvil assembly in a tilted condition.

With the annular inner lips 560 of the snap collar 552 out of overlapping engagement with the annular ledge 524 of the post 556 of the anvil head 540, the distally-oriented force imparted by the annular knife drives the ring assembly 550 distally, whereby the backup member 576 contacts the inner surface 572 of the anvil head 540, and the annular inner lips 560 of the snap ring 552 are received in the depression 526 of the post 556 of the anvil head 540, as shown in FIG. 40. Continued advancement of the annular knife causes the annular knife to pierce the cut ring 578 and ultimately bottom out against the ring body 580 of the backup member 576.

In embodiments, the cut ring 578 and the snap collar 552 may be configured such that the annular knife cuts through the cut ring 578 prior to moving the snap collar 552 out of engagement with the annular ledge 524 of the post 556 of the anvil head 554.

As the ring assembly 550 is advanced toward the distal position, the inwardly extending fingers 598 of the backup member 576 disengage from the arms of the anvil center rod, allowing for the anvil head 540 to pivot relative to the anvil center rod. It is contemplated that the anvil head 540 may be configured to pivot automatically relative to the anvil center rod in any manner described herein. In embodiments, the anvil head 540 may be pivoted via any suitable pivoting mechanism, whether it is automatic or manual.

With reference to FIGS. 41-44, another embodiment of a surgical anvil assembly 626 is illustrated, similar to the anvil assemblies described above. Due to the similarities between the anvil assembly 626 of the present embodiment and the anvil assemblies described above, only those elements of the anvil assembly 626 deemed necessary to elucidate the differences from the above anvil assemblies will be described in detail.

The anvil assembly 626 includes an anvil center rod 638 and an anvil head 640 pivotally mounted to the anvil center rod 638. The anvil head 640 is adapted to pivot between a first operative condition depicted in FIG. 41 and a second pivoted or tilted condition depicted in FIG. 44. The anvil head 640 includes a housing 654 having a post 656 and an anvil tissue contact surface 658. The post 656 may include a pair of spaced post arms defining transverse bores 664 extending through the spaced post arms. The anvil center rod 638 is at least partially positioned about the post 656 and coupled to the anvil head 640 through a pivot member 666.

The anvil center rod 638 may include a pair of distal spaced arms 642 defining a pair of diametrically opposed, longitudinally-extending slots 662. The distal spaced arms 642 includes a distal end through which transverse bores 644 are defined for receiving the pivot member 666 that pivotally couples the post 656 of the anvil head 640 to the distal spaced arms 642 of the anvil center rod 638. The pivot member 666 is coupled to a first location "L1" of the post 656 of the anvil head 640 and which is aligned with a central longitudinal axis "X" defined by the anvil center rod 638.

The anvil assembly 626 further includes a pivoting assembly 600, which replaces the conventional plunger and cam latch assembly for driving the tilting of the anvil head 640. The pivoting assembly 600 is at least partially received within the anvil center rod 638, e.g., between the spaced arms 642, and is spring biased in a proximal direction by a biasing member 602, such as, for example, a coil spring. The pivoting assembly 600 includes a linkage arm 604 received in one of the slots 662 of the distal spaced arms 642 of the anvil center rod 638. The linkage arm 604 has an L-shaped configuration and includes an elongated shaft 606 and a foot or flange 608 extending perpendicularly from a proximal end 606a of the shaft 606. In embodiments, the linkage arm 604 may assume any suitable shape, such as, for example, linear, curved, or the like. The foot 608 of the linkage arm 604 has a detent or post 610 extending distally therefrom for supporting the biasing member 602 of the pivoting assembly 600.

The shaft 606 of the linkage arm 604 is disposed off-center from the central longitudinal axis "X" of the anvil center rod 638. The shaft 606 has a distal end 606b pivotally coupled to a second location "L2" of the post 656 of the anvil head 640 via a pivot member 612, such as, for example, a pin. The second location "L2" of the post 656 of the anvil head 640 at which the shaft 606 is pivotally coupled is both distal and laterally offset from the first location "L1" at which the anvil center rod 638 is pivotally coupled to the post 656 of the anvil head 640. As such, a longitudinal translation of the shaft 606 in the proximal or distal direction effects a pivoting of the anvil head 640 about the first location "L1" in a counter-clockwise or clockwise direction, respectively.

The biasing member 602 of the pivoting assembly 600 is disposed within the anvil center rod 638 and in alignment with the central longitudinal axis "X" of the anvil center rod 638 and the first location "L1." The biasing member 602 defines a bore 614 therethrough that receives the detent 610 of the foot 608 of the linkage arm 604 to support the biasing member 602. The biasing member 602 is interposed between the foot 608 of the linkage arm 604 and the post 656 of the anvil head 640 while being in a compressed state. As such, the compressed biasing member 602 exerts a proximally-oriented force on the foot 608 of the linkage arm 604, which is transferred to the second location "L2" of the post 656 of the anvil head 640. Accordingly, upon unlocking the anvil head 640 from the anvil center rod 638, the biasing member 602 drives or pulls the anvil head 640 toward the second, tilted condition, as will be described.

The anvil assembly 626 may further include a backup member (not shown) and a cut ring (not shown), similar to the backup members and cut rings described above. The backup member is moved within a recess 670 defined in the housing 658 of the anvil head 640 upon application of a force thereto, e.g., during advancement of an annular knife 30 (FIGS. 3 and 6).

In operation, prior to firing of a circular stapling instrument having the surgical anvil assembly 626 of the presently described embodiment, the backup member is in its retracted or proximal position in the recess 670 of the anvil head 640. With the backup member in the proximal position, the backup member is engaged by the spaced arms 642 of the anvil center rod 638, such that the anvil head 640 is retained in the first, operative condition and prevented from pivoting despite the proximally-oriented force exerted by the biasing member 602 on the anvil head 640 via the linkage arm 604.

Upon actuation of the stapling instrument, the annular knife is advanced into engagement with the cut ring, which transfers the distally-oriented force to the backup member, as described in previous embodiments. As the backup member is advanced toward the distal position, the backup member disengages from the arms 642 of the anvil center rod 638, unlocking the anvil head 640 from the anvil center rod 638. With the anvil head 640 unlocked from the anvil center rod 638, e.g., the anvil head 640 is free to pivot, the biasing member 602 of the pivoting assembly 600 drives the linkage arm 604 in a proximal direction, whereby the linkage arm 604 pivots the anvil head 640 relative to the anvil center rod 638 in the counter-clockwise direction, indicated by arrow "B" in FIG. 44. After the anvil head 640 pivots to the second, tilted condition, the anvil head 640 covers the linkage arm 604, preventing the linkage arm 604 from getting caught on tissue during removal of the surgical anvil assembly 626 from a surgical site.

During some operations, the anvil head 640 may be manually pivoted back to the first, operative condition against the spring bias of the biasing member 602. In such instances, as the anvil head 640 is pivoted back to the first, operative condition, the linkage arm 604 is driven or pulled in a distal direction and the biasing member 602 is compressed between the foot 608 of the linkage arm 604 and the post 656 of the anvil head 640, resetting the pivoting assembly 600.

With reference to FIGS. 45-48, another embodiment of a surgical anvil assembly 726 is illustrated, similar to the anvil assemblies described above. Due to the similarities between the anvil assembly 726 of the present embodiment and the anvil assemblies described above, only those elements of the anvil assembly 726 deemed necessary to elucidate the differences from the above anvil assemblies will be described in detail.

The anvil assembly 726 includes an anvil center rod 738 and an anvil head 740 pivotally mounted to the anvil center rod 738. The anvil head 740 is adapted to pivot between a first, operative condition and a second, pivoted or tilted condition. The anvil center rod 738 may include a pair of distal spaced arms 742 for capturing a 756 post of the anvil head 740 therebetween. The distal spaced arms 742 of the anvil center rod 738 defines transverse bores 744 therethrough for receiving a pivot member 766, as will be described.

The anvil head 740 includes a housing 754 defining a recess 770 therein and the post 756 is centrally disposed within the recess 770 and extends proximally therefrom. The post 756 includes a pair of spaced post arms 760 defining a slot 762 dimensioned to capture a cam latch 750 therein. The spaced post arms 760 define transverse bores 764 therethrough dimensioned for receipt of the pivot member 766. The anvil center rod 738 is at least partially positioned about the post 756 and coupled to the anvil head 740 through the pivot member 766 which extends through respective transverse bores 744, 764 of the distal spaced arms 742 of the anvil center rod 738 and the spaced post arms 760 of the post 756 to pivotally couple the anvil head 740 to the anvil center rod 738.

Figure 45:
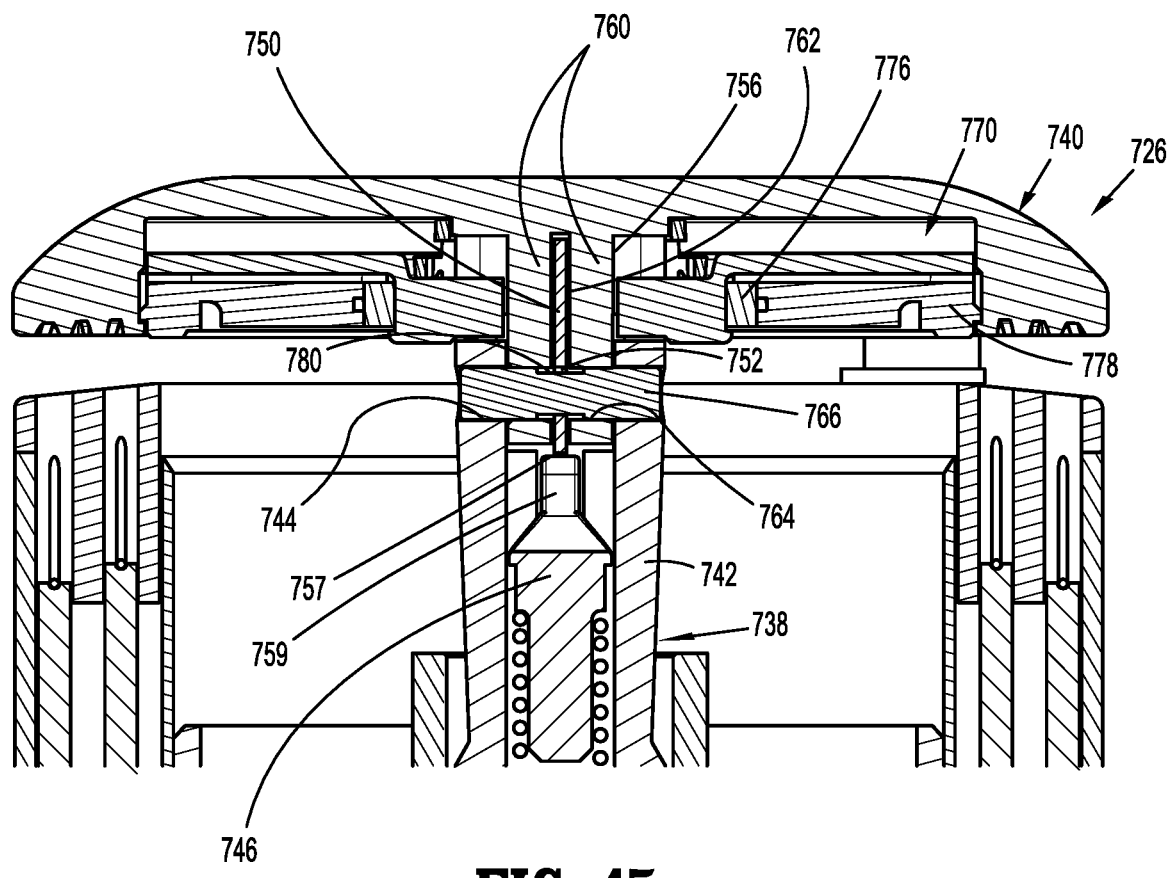
FIG. 45 is a side cross-sectional view of another embodiment of a surgical anvil assembly for incorporation into the circular stapling instrument of FIG. 1.
Figure 46:
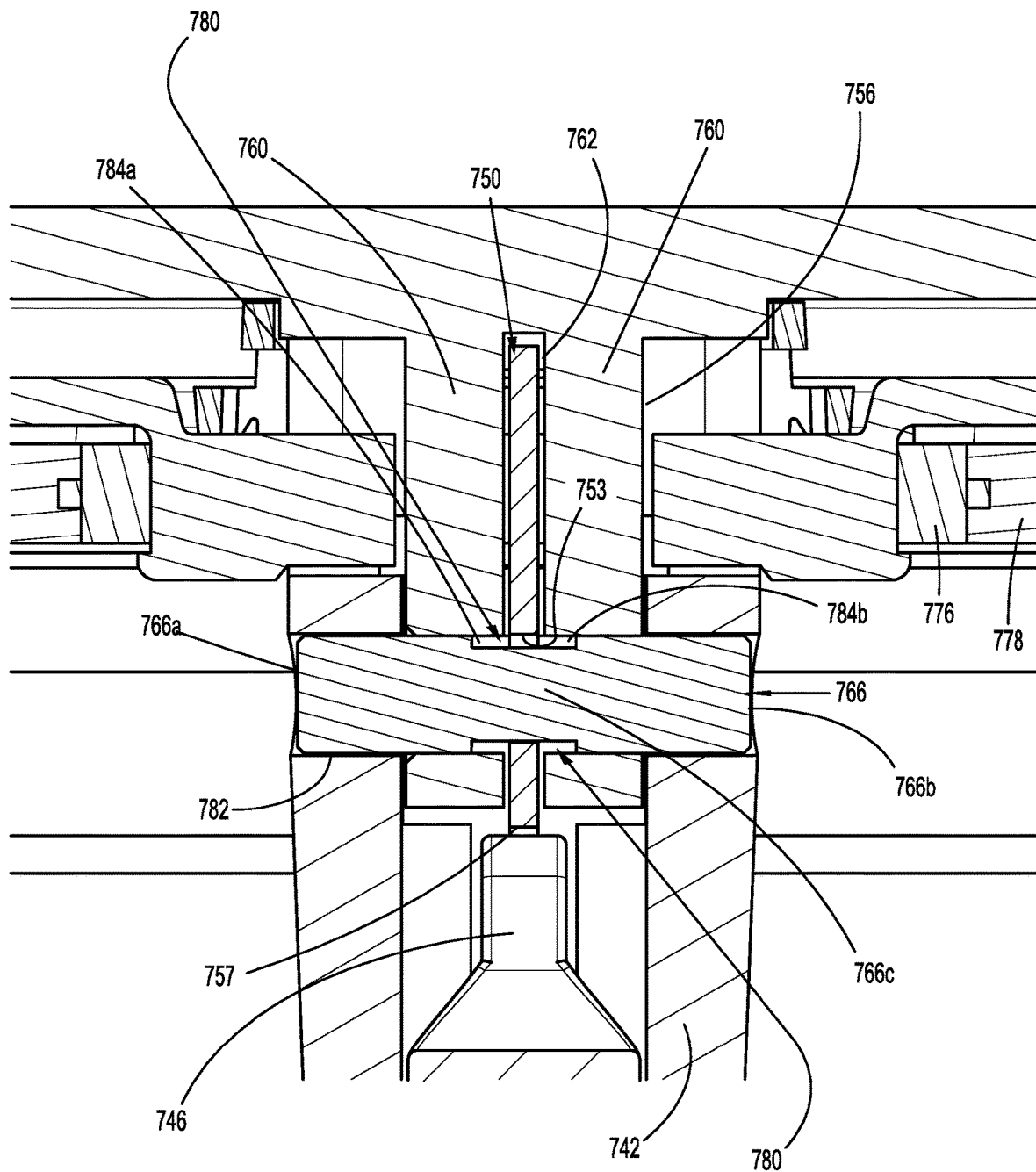
FIG. 46 is an enlarged view of a pivot member of the anvil assembly of FIG. 45.
Figure 47:
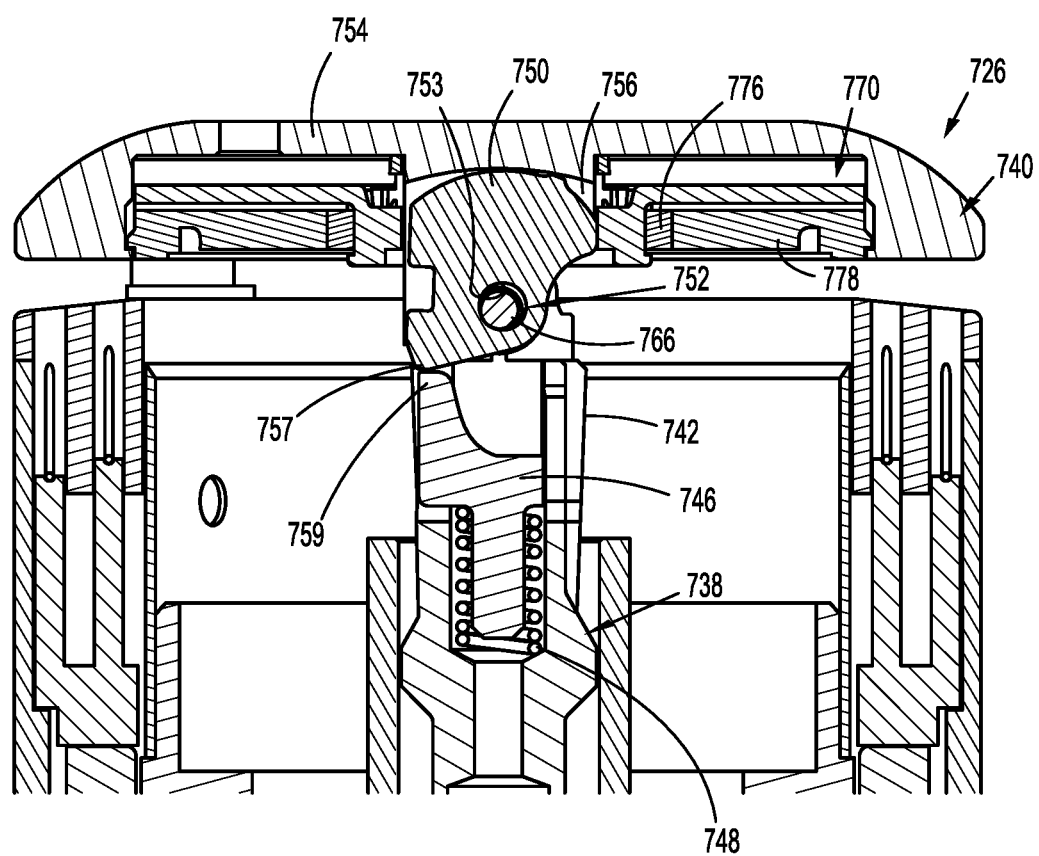
FIG. 47 is another side cross-sectional view of the anvil assembly of FIG. 45.
Figure 48:
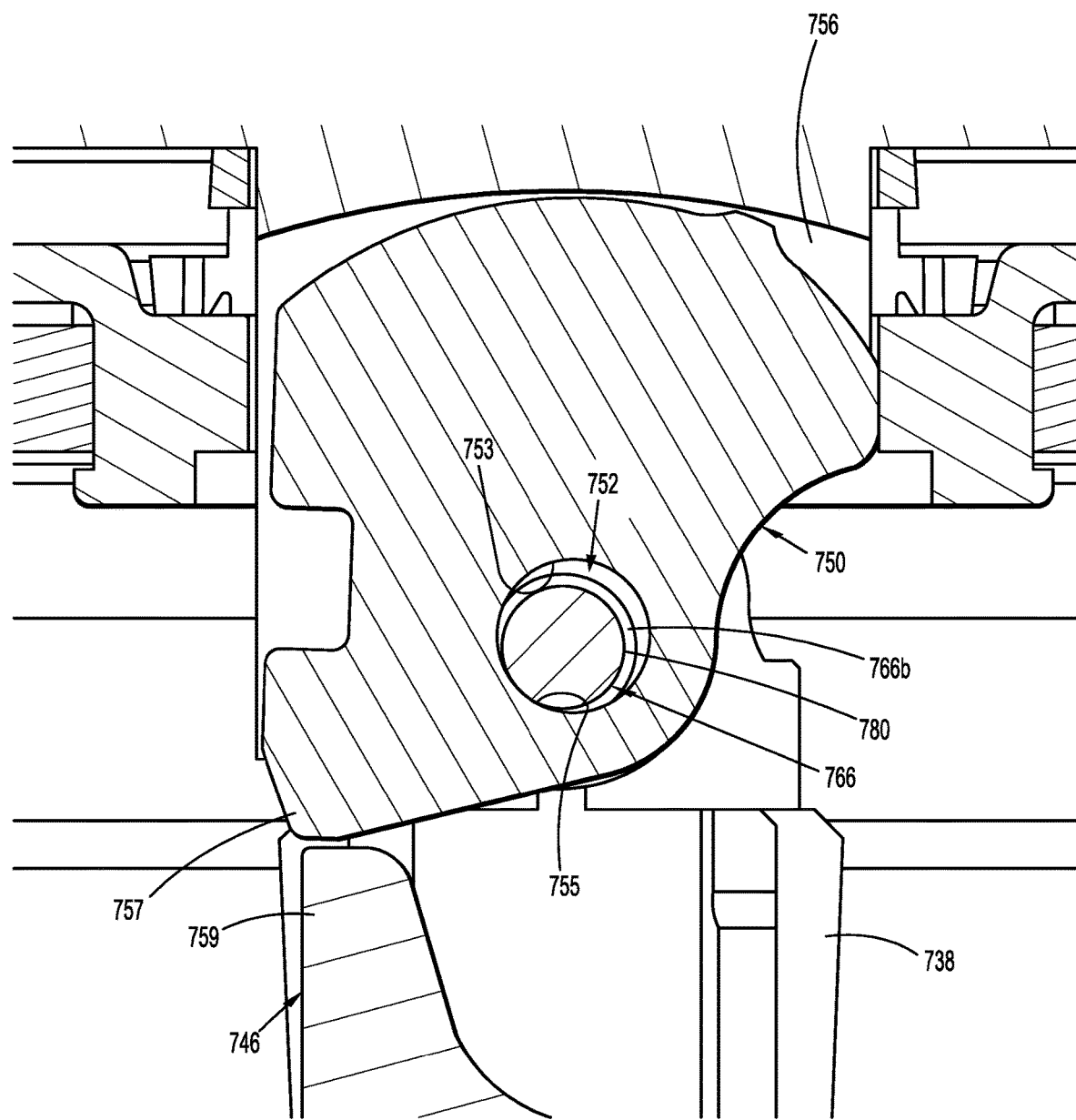
FIG. 48 is an enlarged view of a cam latch of the anvil assembly of FIG. 47.

With reference to FIGS. 45 and 46, the cam latch 750 is received within the slot 762 defined between the spaced post arms 760 of the post 756 and coupled to the anvil center rod 738 and the post 756 via the pivot member 766. The cam latch 750 defines a bore or pin opening 752 through which the pivot member 766 extends. The pin opening 752 in the cam latch 750 is defined by an annular inner surface 753 of the cam latch 750. The cam latch 750 has a proximally-located edge 757 engaged to a plunger 746 for driving a rotation of the cam latch 750. The cam latch 750 is rotationally fixed within the slot 762 of the post 756 of the anvil head 740, such that as the cam latch 750 rotates, due to a spring bias of the plunger 746, the anvil head 740 rotates with the cam latch 750 relative to the anvil center rod 738.

As briefly mentioned above, the pivot member 766 extends through the transverse bores 744 of the distal spaced arms 742 of the anvil center rod 738, the transverse bores 764 of the spaced post arms 760 of the post 756, and the pin opening 752 of the cam latch 750 to allow for pivoting or rotation of the anvil head 740 relative to the anvil center rod 738. The pivot member 766 extends through the bores 744, 764 and the pin opening 752 in a slip fit manner to ease assembly.

The pivot member 766 is an elongated pin-like structure having opposing first and second ends 766a, 766b and an intermediate portion 766c disposed therebetween. It is contemplated that the first and second ends 766a, 766b and the intermediate portion 766c of the pivot member 766 may be monolithically formed. An annular groove 780 is formed in an outer surface 782 of the pivot member 766. The annular groove 780 is disposed along the intermediate portion 766c of the pivot member 766. Accordingly, the first and second ends 766a, 766b of the pivot member 766 have a first diameter, and the intermediate portion 766c of the pivot member 766 has a second diameter, less than the first diameter.

The groove 780 in the pivot member 766 may be cylindrical and extend circumferentially about the intermediate portion 766c of the pivot member 766. As such, the groove 780 has stepped portions 784a, 784b on opposite sides thereof to limit lateral movement of the pivot member 766 within and relative to the pin opening 752 of the cam latch 750. The diameter of the intermediate portion 766c is less than the diameter of the pin opening 752 of the cam latch 750. This allows for a simplified slip fit of the pivot member 766 into the pin opening 752 of the cam latch 750 during assembly.

With reference to FIGS. 45-48, the inner surface 753 of the cam latch 750 has a proximal portion 755 that is received in the groove 780 of the pivot member 766 and which is spring biased into contact with the outer surface 782 of the pivot member 766 via the plunger 746, as will be described. The length of the groove 780 is greater than the thickness of the cam latch 750 to allow for some lateral movement of the pivot member 766 within the pin opening 752 of the cam latch 750.

The anvil assembly 726 further includes the plunger 746 and a plunger spring 748. The plunger 746 is at least partially received within the anvil center rod 738, e.g., between the spaced arms 742, and is spring biased in a distal direction by the plunger spring 748. The plunger 746 includes a plunger finger 759 engaged to the proximal edge 757 of the cam latch 50 to maintain the proximal portion 755 of the inner surface 653 of the cam latch 750 in the groove 780 of the pivot member 766. Due to the spring bias of the plunger 746 on the cam latch 750, the proximal portion 755 of the inner surface 753 of the cam latch 750 is frictionally engaged with the outer surface 782 of the pivot member 766 to retain the pivot member 766 in the pin opening 752 of the cam latch 750.

The anvil assembly 726 further includes a backup member 776 and a cut ring 778, similar to the backup members and cut rings described above. The backup member 776 is moved within the recess 770 of the anvil head 740 upon application of a force thereto, e.g., during advancement of an annular knife 30 (FIGS. 3 and 6). The backup member 776 includes a pair of diametrically opposed fingers (not explicitly shown) extending inwardly. The fingers are engaged by the spaced arms 742 of the anvil center rod 738 to prevent the backup member 776 from moving in a proximal direction and to maintain the anvil head 740 in the operative condition (e.g., untilted). Pivotal movement of the anvil head 740 relative to the anvil assembly 726 is permitted only after the fingers 798 are distally spaced from the arms 742 of the anvil center rod 738, as described in the previous embodiments.

In operation, prior to firing of a circular stapling instrument having the surgical anvil assembly 726 of the presently described embodiment, the backup member 676 is in its retracted or proximal position in the 770 recess of the anvil head 740. With the backup member 776 in the proximal position, the inwardly extending fingers of the backup member 776 are engaged by the spaced arms 742 of the anvil center rod 738, such that the anvil head 740 is retained in the first, operative condition and prevented from pivoting despite the distally-oriented force exerted by the plunger 746 on the anvil head 740 via the cam latch 750.

Upon actuation of the stapling instrument, the annular knife 30 is advanced into engagement with the cut ring 778, which transfers the distally-oriented force to the backup member 776. As the backup member 776 is advanced toward the distal position, the inwardly extending fingers of the backup member 776 disengage from the arms 742 of the anvil center rod 738, unlocking the anvil head 740 from the anvil center rod 738. With the anvil head 740 unlocked from the anvil center rod 738 (e.g., the anvil head 740 is free to pivot), the spring biased plunger 746 drives a rotation of the cam latch 750 about the pivot member 766. Due to the cam latch 750 being rotationally fixed within the anvil head 740, the anvil head 740 is caused to rotate relative to the anvil center rod 738 about the pivot member 766. In embodiments, the pivot member 766 may rotate with the anvil head 740.

With reference to FIGS. 49-52, another embodiment of a surgical anvil assembly 826 is illustrated, similar to the anvil assemblies described above. Due to the similarities between the anvil assembly 826 of the present embodiment and the anvil assemblies described above, only those elements of the anvil assembly 826 deemed necessary to elucidate the differences from the anvil assemblies above will be described in detail.

Figure 49:
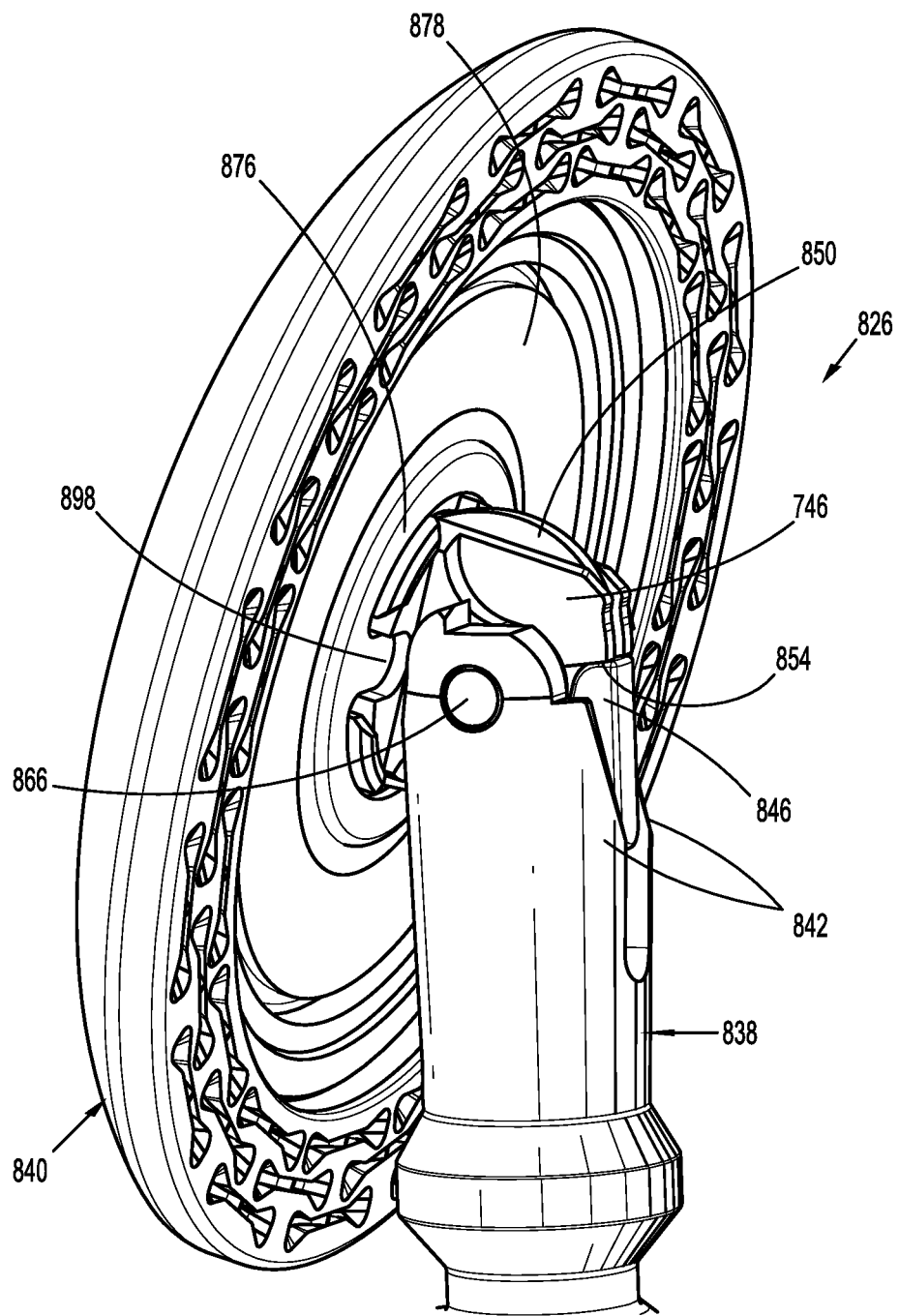
FIG. 49 is a perspective view of another embodiment of a surgical anvil assembly for incorporation into the circular stapling instrument of FIG. 1.
Figure 50:
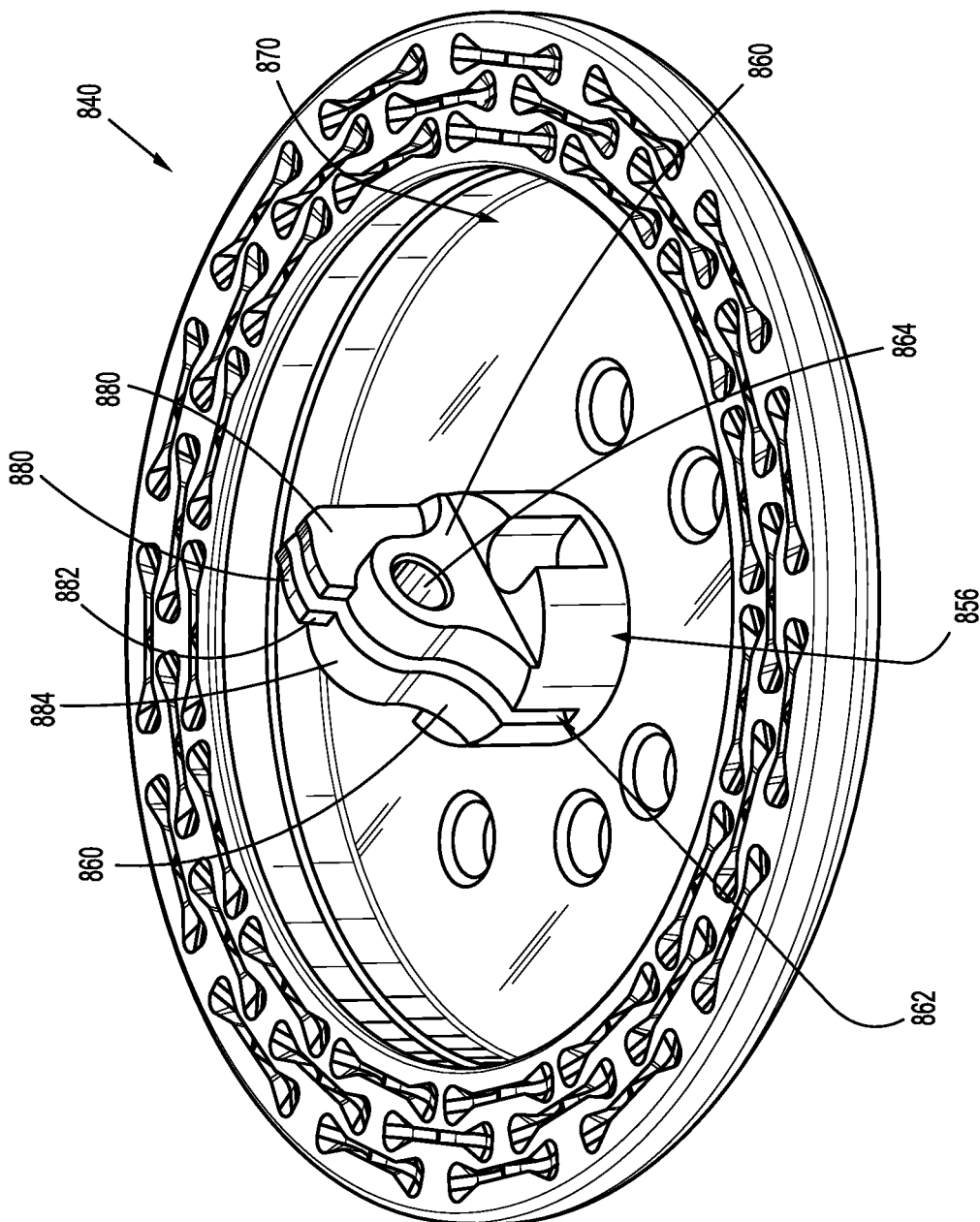
FIG. 50 is a perspective view of a proximal side of an anvil head of the anvil assembly of FIG. 49.
Figure 52:
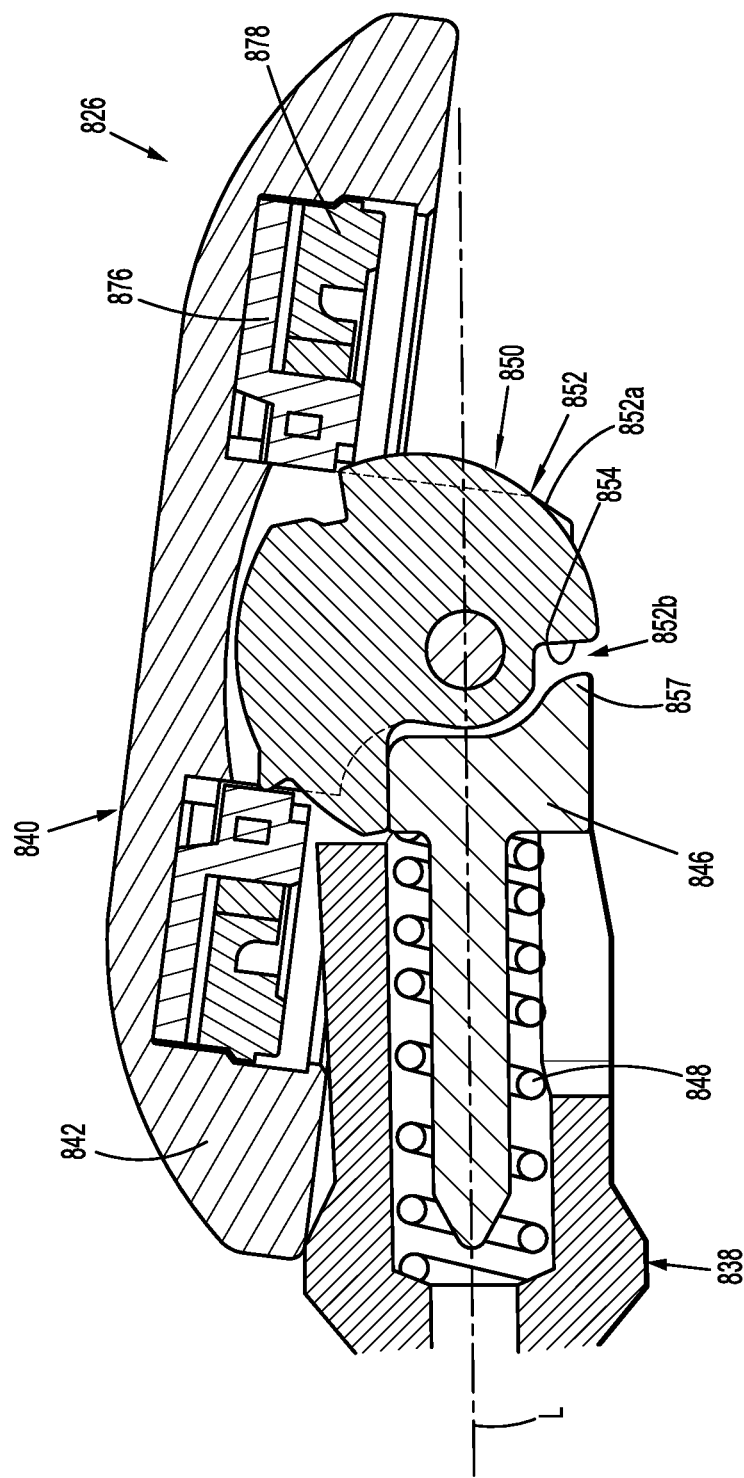
FIG. 52 is a side cross-sectional view of the anvil assembly of FIG. 49 illustrating the anvil head in a tilted condition.

The anvil assembly 826 includes an anvil center rod 838 and an anvil head 840 pivotally mounted to the anvil center rod 838. The anvil head 840 is adapted to pivot between a first, operative condition and a second, pivoted or tilted condition (FIGS. 49 and 52). The anvil center rod 838 may include a pair of distal spaced arms 842 for capturing a post 856 of the anvil head 840 therebetween. The distal spaced arms 842 of the anvil center rod 838 define transverse bores therethrough for receiving a pivot member 866.

The anvil head 840 defines a recess 870 therein. The post 856 is centrally disposed within the recess 870 and extends proximally therefrom. The post 856 includes a pair of spaced post arms 860 defining a slot 862 dimensioned to capture a cam latch 850 therein. The spaced post arms 860 define transverse bores 864 therethrough dimensioned for receipt of the pivot member 866. The anvil center rod 838 is at least partially positioned about the post 856 and coupled to the anvil head 840 through the pivot member 866 which extends through respective transverse bores of the distal spaced arms 842 of the anvil center rod 838 and the spaced post arms 860 of the post 856 to pivotally couple the anvil head 840 to the anvil center rod 838. The post 856 further includes a pair of flanges 880 projecting proximally from the respective pair of post arms 860. The flanges 880 each have a vertical surface 882 projecting perpendicularly from a rounded surface 884 of the respective post arms 860.

Figure 51:
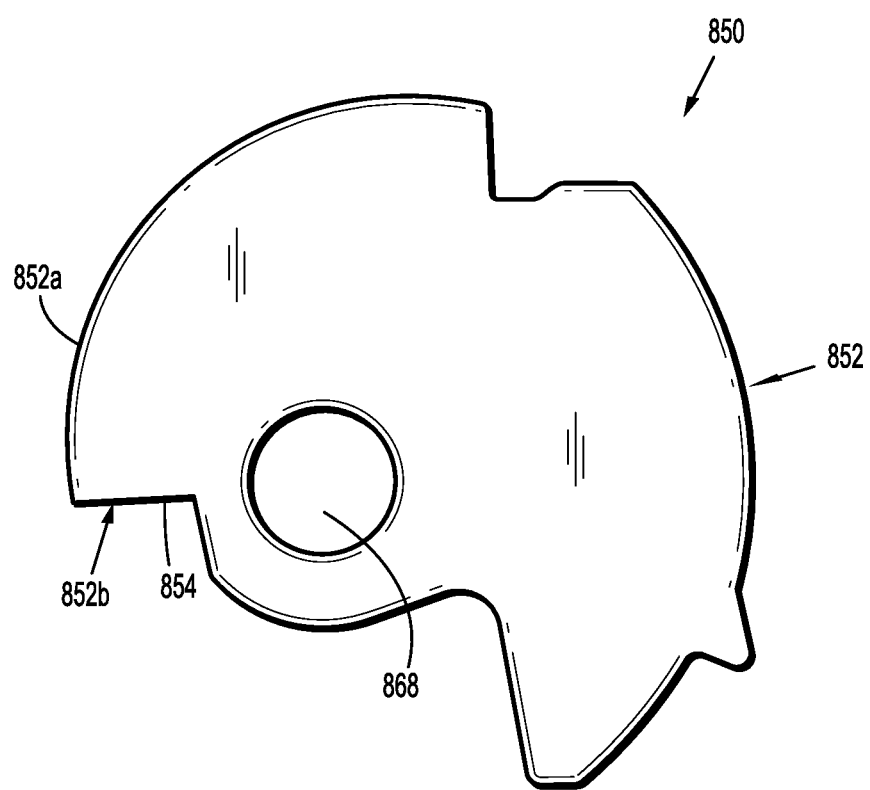
FIG. 51 is a side view of a cam latch of the anvil assembly of FIG. 49.

The cam latch 850 is received between the spaced post arms 860 of the post 856 and between the flanges 880. The cam latch 850 is coupled to the anvil center rod 838 and the post 856 via the pivot member 866 which extends through a bore or pin opening 868 of the cam latch 50. As best shown in FIG. 51, the cam latch 850 has an outer peripheral surface 852 that includes a camming region 852$a$ and a notched region 852$b$ contiguous with the camming region 852$a$. The camming region 852$a$ may have an arcuate shape and is configured to be engaged with a plunger 846 (FIG. 52) that drives a rotation of the cam latch 850.

The notched region 852$b$ of the cam latch 850 has a profile that matches a profile cooperatively defined by the vertical surface 882 of the flanges 880 and the rounded surface 884 of the spaced post arms 860. The notched region 852$b$ includes a stop surface 854 that extends substantially radially inward from an end of the camming region 852$b$. The stop surface 854 is configured to engage a plunger finger 857 of the plunger 846 upon the anvil head 840 entering the second, titled condition, as shown in FIGS. 49 and 52. The cam latch 850 is rotationally fixed within the slot 862 of the post 856 of the anvil head 840, such that as the cam latch 850 rotates, due to a spring bias of the plunger 846, the anvil head 840 rotates with the cam latch 850 relative to the anvil center rod 838.

The anvil assembly 826 further includes the plunger 846 and a plunger spring 848. The plunger 846 is at least partially received within the anvil center rod 838, e.g., between the spaced arms 842, and is spring biased in a distal direction by the plunger spring 848. The plunger spring 848 has a spring constant high enough to prevent a manual compression of the plunger spring 848. As such, manual pivoting of the anvil head 840 from the tilted condition back towards the untilted condition is resisted by the plunger spring 848.

The plunger 846 includes the plunger finger 857 at its distal end, which is engaged to the camming region 852*a* of the cam latch 850 to bias the cam latch 850 and, in turn, the anvil head 840, toward the second, tilted condition. When the anvil head 840 is free to pivot relative to the anvil center rod 838, the plunger finger 857 pushes against the camming region 852*a* of the cam latch 850, whereby the camming region 852*a* of the cam latch 850 rides along the plunger finger 857, rotating the anvil head 840. Upon the anvil head 840 entering the second, tilted condition, the notched region 852*b* of the cam latch 850 passes over the plunger finger 857, whereby the stop surface 854 of the cam latch 850 is positioned in contact with the plunger finger 857. Due to the contact between the stop surface 854 of the cam latch 850 and the plunger finger 857, rotation of the cam latch 850 in the opposite direction (e.g., rotation of the anvil head 840 back toward the first, operative condition) is resisted by the plunger 846 and the plunger spring 848.

The anvil assembly 826 further includes a backup member 876 and a cut ring 878, similar to the backup members and cut rings described above. The backup member 876 is moved within the recess 870 of the anvil head 840 upon application of a force thereto, e.g., during advancement of the annular knife 30 (FIGS. 3 and 6). The backup member 876 includes a pair of diametrically opposed fingers 898 extending inwardly. The fingers 898 are engaged by the spaced arms 842 of the anvil center rod 838 to prevent the backup member 876 from moving in a proximal direction and to maintain the anvil head 840 in the operative condition (e.g., untilted). Pivotal movement of the anvil head 840 relative to the anvil assembly 826 is permitted only after the fingers 898 are distally spaced from the arms 842 of the anvil center rod 838.

In operation, prior to firing of a circular stapling instrument having the surgical anvil assembly 826 of the presently described embodiment, the backup member 876 is in its retracted or proximal position in the recess 870 of the anvil head 840. With the backup member 876 in the proximal position, the inwardly extending fingers 898 of the backup member 876 are engaged by the spaced arms 842 of the anvil center rod 838 such that the anvil head 840 is retained in the first, operative condition and prevented from pivoting despite the distally-oriented force exerted by the plunger 846 on the anvil head 840 via the cam latch 850.

Upon actuation of the stapling instrument, the annular knife 30 is advanced into engagement with the cut ring 878, which transfers the distally-oriented force to the backup member 876. As the backup member 876 is advanced toward the distal position, the inwardly extending fingers 898 of the backup member 876 disengage from the arms 842 of the anvil center rod 838, unlocking the anvil head 840 from the anvil center rod 838, as described in detail above. With the anvil head 840 unlocked from the anvil center rod 838 (e.g., the anvil head 840 is free to pivot), the spring biased plunger 846 drives a rotation of the cam latch 850. Due to the cam latch 850 being rotationally fixed within the anvil head 840, the anvil head 840 is caused to rotate relative to the anvil center rod 838.

Upon the anvil head 840 rotating to the second, tilted condition, the plunger 846 is received in the notched region 852*b* of the cam latch 850, whereby the stop surface 854 of the notched region 852*b* of the cam latch 850 overlaps with the plunger finger 857. As such, an attempt to rotate the anvil head 840 back toward the first, operative condition will be resisted by the distally-oriented force exerted on the notched region 852*b* of the cam latch 850 by the spring biased plunger 846. As noted above, the biasing member 848 has a spring constant high enough to resist a manual attempt at resetting the anvil head 840.

Figure 55:
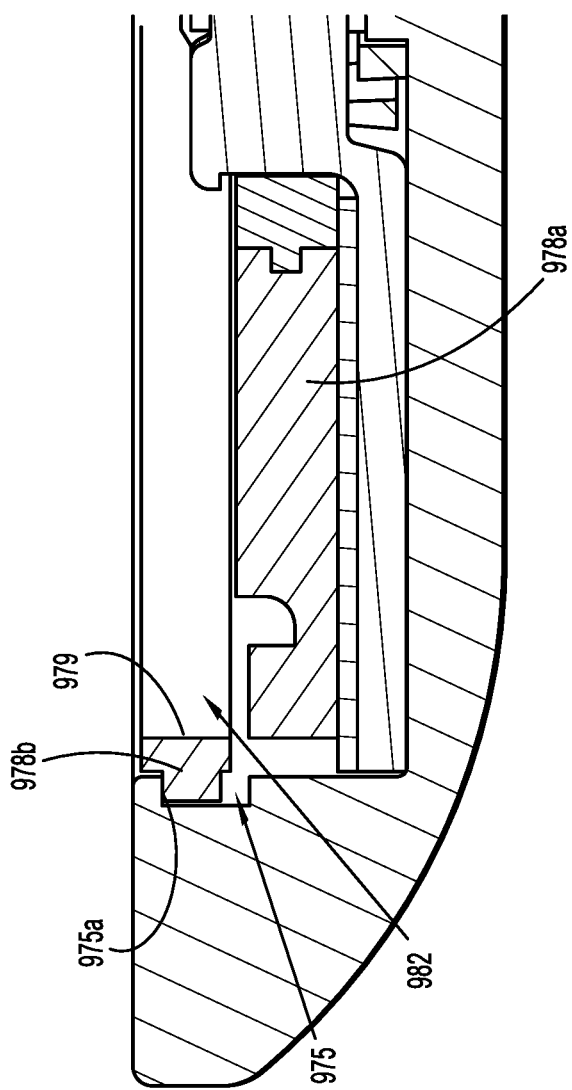
FIG. 55 is a side cross-sectional view of the surgical anvil assembly of FIG. 53 illustrating the ring assembly after a retraction of an annular knife.

With reference to FIGS. 53-55, another embodiment of a surgical anvil assembly 926 is illustrated, similar to the anvil assemblies described above. Due to the similarities between the anvil assembly 926 of the present embodiment and the anvil assemblies described above, only those elements of the anvil assembly 926 deemed necessary to elucidate the differences from anvil assemblies described above will be described in detail.

The anvil assembly 926 generally includes an anvil center rod (not shown), similar to the anvil center rods described above, an anvil head 940 pivotally mounted to the anvil center rod, and a ring assembly 950 configured to selectively unlock the anvil head 940 from the anvil center rod. The anvil head 940 is configured to pivot relative to the anvil center rod between a first operative condition and a second pivoted or tilted condition.

The anvil head 940 includes an inner surface 972 defining a recess 970 therein dimensioned for receipt of the ring assembly 950. The inner surface 972 has an outer periphery 973 that defines an annular groove 975 therein. The groove 975 extends radially outward from the recess 970 and is in communication therewith. The groove 975 is disposed adjacent a tissue contacting surface 958 of the anvil head 940 and extends circumferentially about the outer periphery 973 of the inner surface 972 of the anvil head 940. A height of the groove 975 is defined between a proximal ledge 975*a* and a distal ledge 975*b* thereof.

The ring assembly 940 includes a backup member 976, similar to backup member 476 described above, and a cut ring 978. The backup member 976 is received in the recess 970 of the anvil head 940, and the cut ring 978 is nested in the backup member 976. The cut ring includes an annular inner body portion 978*a* and an annular outer body portion 978*b* integrally formed with, and disposed circumferentially about, the inner body portion 978*a*. The inner and outer body portions 978*a*, 978*b* may be formed from a unitary piece of polytetrafluoroethylene, polypropylene or polyester. Other materials are contemplated. In some embodiments, the outer body portion 978*b* may be a separate piece attached to the inner body portion 978*a*.

The inner body portion 978*a* of the cut ring 978 is supported on the backup member 976 and is disposed in the recess 970 of the anvil head 940, and the outer body portion 978*b* of the cut ring 978 is captured between the proximal and distal ledges 975*a*, 975*b* of the groove 975 of the anvil head 940. The cut ring 978 has a greater diameter than the diameter of the recess 970 of the anvil head 940, such that the cut ring 978 may be press-fit into the recess 970 during assembly. Once assembled, the outer body portion 978*b* of the cut ring 978 extends radially beyond the backup member 976. Due to the outer body portion 978*b* of the cut ring 978 overlapping with the proximal and distal ledges 975*a*, 975*b*, both proximal and distal movement of the outer body portion 978*b* of the cut ring 978 out of the groove 975 is resisted. The outer body portion 978*b* of the cut ring 978 may have a reduced thickness in relation to the inner body portion 978*a* to allow for some play of the outer body portion 978*b* of the cut ring 978 within the groove 975, as will be described. In embodiments, the height of the inner body portion 978a of the cut ring 978 may be substantially similar to or the same as the height of the groove 975.

In operation, prior to firing a circular stapling instrument having the surgical anvil assembly 926 of the presently described embodiment, the ring assembly 950, including the backup member 976 and the cut ring 978, is in its retracted or proximal position. A frangible retainer member (not explicitly shown) is interposed between the backup member 976 and the inner surface 972 of the anvil head 940 to support the ring assembly 950 in the proximal position, as shown in FIG. 53. With the ring assembly 950 in the proximal position, the backup member 976 is engaged by the anvil center rod, such that the anvil head 940 is retained in the first, operative condition.

Upon actuation of the stapling instrument, an annular knife, such as, for example, the annular knife 30 shown in FIG. 6, is advanced into engagement with the cut ring 978 and dissevers or shears off the outer body portion 978b of the cut ring 978 from the inner body portion 978a of the cut ring 978. Upon cutting through the cut ring 978, the annular knife 30 engages the backup member 976, thereby driving the backup member 976 toward the distal position.

Due to the inner body portion 978a of the cut ring 978 being retained with the backup member 976, the inner body portion 978a moves toward the distal position with the backup member 976. The outer body portion 978b of the cut ring 978 is captured between the outer periphery 973 of the inner surface 972 of the anvil head 940 and an outer surface of the annular knife 30. Thus, as shown in FIG. 54, the outer body portion 978b of the cut ring 978 is held in the groove 975 as the inner body portion 978a of the cut ring 978 is distally advanced.

As the ring assembly 950 is advanced toward the distal position, the backup member 976 disengages from the anvil center rod, allowing for the anvil head 940 to pivot relative to the anvil center rod. It is contemplated that the anvil head 940 may be configured to pivot automatically relative to the anvil center rod in any manner described herein. In embodiments, the anvil head 940 may be pivoted via any suitable pivoting mechanism, whether it is automatic or manual.

With reference to FIG. 55, a retraction of the annular knife 30 back to its starting position causes the outer body portion 978b of the cut ring 978 to move proximally within the groove 975 due to the frictional engagement between an outer surface of the annular knife 30 and an inner peripheral surface 979 of the outer body portion 978b of the cut ring 978. The outer body portion 978b of the cut ring 978 is dragged proximally by the retracting annular knife 30 until the outer body portion 978b of the cut ring 978 contacts the proximal ledge 975a. With the outer body portion 978b of the cut ring 978 in contact with the proximal ledge 975a, the outer body portion 975b and the inner body portion 978a are axially spaced from one another, creating a passage 982 through which staples lodged in the cut ring 978 may be removed.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical anvil assembly for use with a circular stapling instrument, comprising:
    an anvil center rod;
    an anvil head pivotally coupled to the anvil center rod and movable between a first, operative condition and a second, tilted condition, the anvil head having an inner surface defining a recess therein, the inner surface having an outer periphery defining a groove extending radially outward from the recess; and
    a ring assembly including:
        a backup member disposed within the recess of the anvil head; and
        a cut ring nested with the backup member and captured in the groove of the anvil head, wherein the ring assembly is movable within the recess from a proximal position preventing pivotal movement of the anvil head from the first, operative condition, to a distal position permitting pivotal movement of the anvil head to the second, tilted condition, the cut ring including:
            an annular inner body portion disposed in the recess of the anvil head; and
            an annular outer body portion received in the groove of the anvil head, wherein the outer body portion is configured to be disconnected from the inner body portion upon an advancement of an annular knife through the cut ring,
        wherein the backup member has an outer peripheral edge disposed adjacent the outer periphery of the inner surface of the anvil head such that the backup member overlaps the inner body portion and the outer body portion of the cut ring.

2. The surgical anvil assembly according to claim 1, wherein the groove is adjacent a tissue-contacting surface of the anvil head, such that the groove maintains the cut ring adjacent the tissue-contacting surface.

3. The surgical anvil assembly according to claim 1, wherein the outer body portion of the cut ring is disposed adjacent a tissue-contacting surface of the anvil head when the ring assembly is in the proximal position and the distal position.

4. The surgical anvil assembly according to claim 1, wherein the outer periphery of the inner surface has a proximal ledge and a distal ledge, the outer body portion of the cut ring being captured between the proximal and distal ledges.

5. The surgical anvil assembly according to claim 4, wherein the distal ledge is configured to maintain the outer body portion of the cut ring in the groove as the ring assembly moves toward the distal position.

6. The surgical anvil assembly according to claim 4, wherein the proximal ledge is configured to resist proximal movement of the outer body portion of the cut ring out of the groove.

7. The surgical anvil assembly according to claim 4, wherein the outer body portion of the cut ring is axially movable within the groove between the proximal and distal ledges.

* * * * *